(12) United States Patent
Deisseroth et al.

(10) Patent No.: US 10,568,307 B2
(45) Date of Patent: Feb. 25, 2020

(54) STABILIZED STEP FUNCTION OPSIN PROTEINS AND METHODS OF USING THE SAME

(75) Inventors: Karl Deisseroth, Stanford, CA (US); Ofer Yizhar, Palo Alto, CA (US); Lief Fenno, San Francisco, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 438 days.

(21) Appl. No.: 13/882,666

(22) PCT Filed: Nov. 4, 2011

(86) PCT No.: PCT/US2011/059390
§ 371 (c)(1),
(2), (4) Date: Sep. 17, 2013

(87) PCT Pub. No.: WO2012/061744
PCT Pub. Date: May 10, 2012

(65) Prior Publication Data
US 2013/0347137 A1    Dec. 26, 2013

Related U.S. Application Data

(60) Provisional application No. 61/511,905, filed on Jul. 26, 2011, provisional application No. 61/410,711, filed on Nov. 5, 2010, provisional application No. 61/410,704, filed on Nov. 5, 2010.

(51) Int. Cl.
| | | |
|---|---|---|
| G01N 33/50 | (2006.01) | |
| A01K 67/027 | (2006.01) | |
| C07K 14/405 | (2006.01) | |
| C12N 5/0793 | (2010.01) | |

(52) U.S. Cl.
CPC ........ *A01K 67/0275* (2013.01); *C07K 14/405* (2013.01); *C12N 5/0619* (2013.01); *G01N 33/5088* (2013.01); *G01N 33/5091* (2013.01); *A01K 2217/206* (2013.01); *A01K 2227/105* (2013.01); *A01K 2267/0393* (2013.01)

(58) Field of Classification Search
CPC .......... A01K 67/0275; A01K 2217/206; A01K 2227/105; A01K 2267/03; A01K 2267/0393; C07K 14/405; C12N 5/0619; C12N 2740/16043; C12N 2750/14143; G01N 33/5088; G01N 33/5091
See application file for complete search history.

(56) References Cited

U.S. PATENT DOCUMENTS

| | | |
|---|---|---|
| 2,968,302 A | 1/1961 | Fry et al. |
| 3,131,690 A | 5/1964 | Innis et al. |
| 3,499,437 A | 3/1970 | Balamuth et al. |
| 3,567,847 A | 3/1971 | Price |
| 4,343,301 A | 8/1982 | Indech |
| 4,559,951 A | 12/1985 | Dahl et al. |
| 4,616,231 A | 10/1986 | Autrey et al. |
| 4,865,042 A | 9/1989 | Umemura et al. |
| 4,879,284 A | 11/1989 | Lang et al. |
| 5,032,123 A | 7/1991 | Katz et al. |
| 5,041,224 A | 8/1991 | Ohyama et al. |
| 5,082,670 A | 1/1992 | Gage et al. |
| 5,249,575 A | 10/1993 | Di Mino et al. |
| 5,267,152 A | 11/1993 | Yang et al. |
| 5,290,280 A | 3/1994 | Daikuzono et al. |
| 5,330,515 A | 7/1994 | Rutecki et al. |
| 5,382,516 A | 1/1995 | Bush |
| 5,411,540 A | 5/1995 | Edell et al. |
| 5,445,608 A | 8/1995 | Chen et al. |
| 5,460,950 A | 10/1995 | Barr et al. |
| 5,460,954 A | 10/1995 | Lee et al. |
| 5,470,307 A | 11/1995 | Lindall |
| 5,495,541 A | 2/1996 | Murray et al. |
| 5,520,188 A | 5/1996 | Hennige et al. |
| 5,527,695 A | 6/1996 | Hodges et al. |
| 5,550,316 A | 8/1996 | Mintz |
| 5,641,650 A | 6/1997 | Turner et al. |
| 5,703,985 A | 12/1997 | Owyang et al. |
| 5,722,426 A | 3/1998 | Kolff |
| 5,738,625 A | 4/1998 | Gluck |
| 5,739,273 A | 4/1998 | Engelman et al. |
| 5,741,316 A | 4/1998 | Chen et al. |
| 5,755,750 A | 5/1998 | Petruska et al. |
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,816,256 A | 10/1998 | Kissinger et al. |
| 5,836,941 A | 11/1998 | Yoshihara et al. |
| 5,898,058 A | 4/1999 | Nichols |
| 5,939,320 A | 8/1999 | Littman et al. |
| 6,056,738 A | 5/2000 | Marchitto et al. |
| 6,057,114 A | 5/2000 | Akong |
| 6,108,081 A | 8/2000 | Holtom et al. |
| 6,134,474 A | 10/2000 | Fischell et al. |
| 6,161,045 A | 12/2000 | Fischell et al. |

(Continued)

FOREIGN PATENT DOCUMENTS

| | | |
|---|---|---|
| CN | 1079464 A | 12/1993 |
| CN | 1558222 A | 12/2004 |

(Continued)

OTHER PUBLICATIONS

Clark et al. "A future for transgenic livestock." Nat Rev Genet. Oct. 2003;4(10):825-33.*

(Continued)

*Primary Examiner* — Titilayo Moloye
(74) *Attorney, Agent, or Firm* — Rudy J. Ng; Paula A. Borden; Bozicevic, Field & Francis LLP

(57) ABSTRACT

Provided herein are compositions comprising non-human animals comprising neurons expressing stabilized step function opsin proteins on neural plasma membranes and methods of using the same to selectively depolarize neurons residing in microcircuits of the pre-frontal cortex to affect one or more social behaviors, communications, and/or conditioned behaviors in the non-human animal.

10 Claims, 18 Drawing Sheets

Specification includes a Sequence Listing.

(56) References Cited

U.S. PATENT DOCUMENTS

| | | |
|---|---|---|
| 6,180,613 B1 | 1/2001 | Kaplitt et al. |
| 6,253,109 B1 | 6/2001 | Gielen |
| 6,289,229 B1 | 9/2001 | Crowley |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,346,101 B1 | 2/2002 | Alfano et al. |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,615,080 B1 | 9/2003 | Unsworth et al. |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,808,873 B2 | 10/2004 | Murphy et al. |
| 6,810,285 B2 | 10/2004 | Pless et al. |
| 6,889,085 B2 | 5/2005 | Dawson |
| 6,918,872 B2 | 7/2005 | Yokoi |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et al. |
| 7,220,240 B2 | 5/2007 | Struys et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,824,869 B2 | 11/2010 | Hegemann et al. |
| 7,883,536 B1 | 2/2011 | Bendett |
| 7,988,688 B2 | 8/2011 | Webb et al. |
| 8,386,312 B2 | 2/2013 | Pradeep et al. |
| 8,398,692 B2 | 3/2013 | Deisseroth et al. |
| 8,401,609 B2 | 3/2013 | Deisseroth et al. |
| 8,696,722 B2 | 4/2014 | Deisseroth et al. |
| 8,716,447 B2 | 5/2014 | Deisseroth et al. |
| 8,815,582 B2 | 8/2014 | Deisseroth et al. |
| 8,906,360 B2 | 12/2014 | Deisseroth et al. |
| 8,926,959 B2 | 1/2015 | Deisseroth et al. |
| 8,932,562 B2 | 1/2015 | Deisseroth et al. |
| 9,057,734 B2 | 6/2015 | Cohen |
| 9,079,940 B2 | 7/2015 | Deisseroth et al. |
| 9,175,095 B2 | 11/2015 | Deisseroth et al. |
| 9,249,234 B2 | 2/2016 | Deisseroth et al. |
| 9,309,296 B2 | 4/2016 | Deisseroth et al. |
| 9,340,589 B2 | 5/2016 | Deisseroth et al. |
| 9,359,449 B2 | 6/2016 | Deisseroth et al. |
| 9,421,258 B2 | 8/2016 | Deisseroth et al. |
| 9,458,208 B2 | 10/2016 | Deisseroth et al. |
| 9,522,288 B2 | 12/2016 | Deisseroth et al. |
| 9,604,073 B2 | 3/2017 | Deisseroth et al. |
| 9,636,380 B2 | 5/2017 | Deisseroth et al. |
| 9,850,290 B2 | 12/2017 | Deisseroth et al. |
| 9,968,652 B2 | 5/2018 | Deisseroth et al. |
| 10,064,912 B2 | 9/2018 | Deisseroth et al. |
| 10,071,132 B2 | 9/2018 | Deisseroth et al. |
| 2001/0023346 A1 | 9/2001 | Loeb |
| 2002/0094516 A1 | 7/2002 | Calos et al. |
| 2002/0155173 A1 | 10/2002 | Chopp et al. |
| 2002/0164577 A1 | 11/2002 | Tsien et al. |
| 2002/0190922 A1 | 12/2002 | Tsao |
| 2002/0193327 A1 | 12/2002 | Nemerow et al. |
| 2003/0009103 A1 | 1/2003 | Yuste et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0082809 A1 | 5/2003 | Quail et al. |
| 2003/0088060 A1 | 5/2003 | Benjamin et al. |
| 2003/0097122 A1 | 5/2003 | Ganz et al. |
| 2003/0103949 A1 | 6/2003 | Carpenter et al. |
| 2003/0104512 A1 | 6/2003 | Freeman et al. |
| 2003/0125719 A1 | 7/2003 | Furnish |
| 2003/0144650 A1 | 7/2003 | Smith |
| 2003/0204135 A1 | 10/2003 | Bystritsky |
| 2003/0232339 A1 | 12/2003 | Shu et al. |
| 2004/0013645 A1 | 1/2004 | Monahan et al. |
| 2004/0015211 A1 | 1/2004 | Nurmikko et al. |
| 2004/0023203 A1 | 2/2004 | Miesenbock et al. |
| 2004/0034882 A1 | 2/2004 | Vale et al. |
| 2004/0039312 A1 | 2/2004 | Hillstead et al. |
| 2004/0049134 A1 | 3/2004 | Tosaya et al. |
| 2004/0068202 A1 | 4/2004 | Hansson et al. |
| 2004/0073278 A1 | 4/2004 | Pachys |
| 2004/0076613 A1 | 4/2004 | Mazarkis et al. |
| 2004/0122475 A1 | 6/2004 | Myrick et al. |
| 2004/0203152 A1 | 10/2004 | Calos |
| 2004/0216177 A1 | 10/2004 | Jordan et al. |
| 2004/0260367 A1 | 12/2004 | Taboada et al. |
| 2004/0267118 A1 | 12/2004 | Dawson |
| 2005/0020945 A1 | 1/2005 | Tosaya et al. |
| 2005/0027284 A1 | 2/2005 | Lozano et al. |
| 2005/0058987 A1 | 3/2005 | Shi et al. |
| 2005/0088177 A1 | 4/2005 | Schreck et al. |
| 2005/0102708 A1 | 5/2005 | Lecanu et al. |
| 2005/0107753 A1 | 5/2005 | Rezai et al. |
| 2005/0112759 A1 | 5/2005 | Radisic et al. |
| 2005/0119315 A1 | 6/2005 | Fedida et al. |
| 2005/0124897 A1 | 6/2005 | Chopra |
| 2005/0143295 A1 | 6/2005 | Walker et al. |
| 2005/0143790 A1 | 6/2005 | Kipke et al. |
| 2005/0153885 A1 | 7/2005 | Yun et al. |
| 2005/0197679 A1 | 9/2005 | Dawson |
| 2005/0202398 A1 | 9/2005 | Hegemann et al. |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2005/0279354 A1 | 12/2005 | Deutsch et al. |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0057614 A1 | 3/2006 | Heintz |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0129126 A1 | 6/2006 | Kaplitt et al. |
| 2006/0155348 A1 | 7/2006 | deCharms |
| 2006/0161227 A1 | 7/2006 | Walsh et al. |
| 2006/0167500 A1 | 7/2006 | Towe et al. |
| 2006/0179501 A1 | 8/2006 | Chan et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0027443 A1 | 2/2007 | Rose et al. |

(56) References Cited

U.S. PATENT DOCUMENTS

| | | |
|---|---|---|
| 2007/0031924 A1 | 2/2007 | Li et al. |
| 2007/0053996 A1 | 3/2007 | Boyden et al. |
| 2007/0054319 A1 | 3/2007 | Boyden et al. |
| 2007/0060915 A1 | 3/2007 | Kucklick |
| 2007/0060984 A1 | 3/2007 | Webb et al. |
| 2007/0135875 A1 | 6/2007 | Demarais et al. |
| 2007/0156180 A1 | 7/2007 | Jaax et al. |
| 2007/0191906 A1 | 8/2007 | Lyer et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand |
| 2007/0260295 A1 | 11/2007 | Chen et al. |
| 2007/0261127 A1 | 11/2007 | Boyden et al. |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0033569 A1 | 2/2008 | Ferren et al. |
| 2008/0046053 A1 | 2/2008 | Wagner et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1 | 4/2008 | Schneider et al. |
| 2008/0088258 A1 | 4/2008 | Ng |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0176076 A1 | 7/2008 | Van Veggel et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |
| 2008/0290318 A1 | 11/2008 | Van Veggel et al. |
| 2009/0030930 A1 | 1/2009 | Pradeep et al. |
| 2009/0054954 A1 | 2/2009 | Foley et al. |
| 2009/0069261 A1 | 3/2009 | Dodge et al. |
| 2009/0088680 A1 | 4/2009 | Aravanis et al. |
| 2009/0093403 A1 | 4/2009 | Zhang et al. |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0148861 A1 | 6/2009 | Pegan et al. |
| 2009/0157145 A1 | 6/2009 | Cauller |
| 2009/0131837 A1 | 10/2009 | Zhang et al. |
| 2009/0254134 A1 | 10/2009 | Nikolov et al. |
| 2009/0268511 A1 | 10/2009 | Birge et al. |
| 2009/0306474 A1 | 12/2009 | Wilson |
| 2009/0319008 A1 | 12/2009 | Mayer |
| 2009/0326603 A1 | 12/2009 | Boggs |
| 2010/0009444 A1 | 1/2010 | Herlitze et al. |
| 2010/0016783 A1 | 1/2010 | Bourke et al. |
| 2010/0021982 A1 | 1/2010 | Herlitze |
| 2010/0145418 A1 | 6/2010 | Zhang et al. |
| 2010/0146645 A1 | 6/2010 | Vasar et al. |
| 2010/0190229 A1 | 7/2010 | Deisseroth et al. |
| 2010/0209352 A1 | 8/2010 | Hultman et al. |
| 2010/0234273 A1 | 9/2010 | Deisseroth et al. |
| 2011/0021270 A1 | 1/2011 | Vo-Dinh et al. |
| 2011/0092800 A1 | 4/2011 | Yoo et al. |
| 2011/0105998 A1 | 5/2011 | Zhang et al. |
| 2011/0112179 A1 | 5/2011 | Deisseroth et al. |
| 2011/0112463 A1 | 5/2011 | Silver et al. |
| 2011/0125077 A1 | 5/2011 | Denison et al. |
| 2011/0125078 A1 | 5/2011 | Denison et al. |
| 2011/0159562 A1 | 6/2011 | Deisseroth et al. |
| 2011/0165681 A1 | 7/2011 | Boyden et al. |
| 2011/0166632 A1 | 7/2011 | Deisseroth et al. |
| 2011/0172653 A1 | 7/2011 | Deisseroth et al. |
| 2011/0224095 A1 | 9/2011 | Zoller et al. |
| 2011/0233046 A1 | 9/2011 | Nikolenko et al. |
| 2011/0301529 A1 | 12/2011 | Deisseroth et al. |
| 2011/0311489 A1 | 12/2011 | Deisseroth et al. |
| 2012/0093772 A1 | 4/2012 | Horsager et al. |
| 2012/0121542 A1 | 5/2012 | Chuong et al. |
| 2012/0165904 A1 | 6/2012 | Deisseroth et al. |
| 2012/0190629 A1 | 7/2012 | Tomita et al. |
| 2012/0253261 A1 | 10/2012 | Poletto et al. |
| 2013/0019325 A1 | 1/2013 | Deisseroth et al. |
| 2013/0030275 A1 | 1/2013 | Seymour et al. |
| 2013/0066402 A1 | 3/2013 | Lin et al. |
| 2013/0144359 A1 | 6/2013 | Kishawi et al. |
| 2013/0286181 A1 | 10/2013 | Betzig et al. |
| 2015/0112411 A1 | 4/2015 | Beckman et al. |

FOREIGN PATENT DOCUMENTS

| | | |
|---|---|---|
| CN | 101288768 A | 10/2008 |
| CN | 102076866 A | 5/2011 |
| CN | 103313752 A | 9/2013 |
| CN | 103476456 A | 12/2013 |
| EP | 1197144 | 4/2002 |
| EP | 1 334 748 | 8/2003 |
| EP | 1444889 | 8/2004 |
| EP | 1873566 | 1/2008 |
| JP | 2006-295350 | 10/1994 |
| JP | H 09505771 A | 6/1997 |
| JP | 2004534508 | 11/2004 |
| JP | 2005034073 A | 2/2005 |
| JP | 2006217866 | 8/2006 |
| JP | 2007530027 A | 11/2007 |
| JP | 2008010422 A | 1/2008 |
| JP | 2010227537 A | 10/2010 |
| JP | 2012508581 | 4/2012 |
| WO | WO 1995/005214 | 2/1995 |
| WO | WO 1996/032076 | 10/1996 |
| WO | WO 2000/027293 | 5/2000 |
| WO | WO 2001-025466 | 4/2001 |
| WO | WO 03/106486 A2 | 2/2003 |
| WO | WO 2013/016486 | 2/2003 |
| WO | WO 2003-040323 | 5/2003 |
| WO | WO 2003/046141 | 6/2003 |
| WO | WO 2003-084994 | 10/2003 |
| WO | WO 2003-102156 | 12/2003 |
| WO | WO 2004/033647 | 4/2004 |
| WO | WO 2005/093429 | 10/2005 |
| WO | WO 2006/103678 | 10/2006 |
| WO | WO 2007-024391 | 3/2007 |
| WO | WO 2007-131180 | 11/2007 |
| WO | WO 2008/014382 | 1/2008 |
| WO | WO 2008/086470 | 7/2008 |
| WO | WO 2008/106694 | 9/2008 |
| WO | WO 2009/025819 | 2/2009 |
| WO | WO 2009/072123 | 6/2009 |
| WO | WO2009/119782 | 10/2009 |
| WO | WO 2009-131837 | 10/2009 |
| WO | WO 2009/148946 | 12/2009 |
| WO | WO 2010/006049 | 1/2010 |
| WO | WO 2010/011404 A3 | 1/2010 |
| WO | WO 2010/056970 | 5/2010 |
| WO | WO 2010056970 A2 * | 5/2010 |
| WO | WO-2010123993 | 10/2010 |
| WO | WO 2011/005978 | 1/2011 |
| WO | WO 2011/066320 A3 | 6/2011 |
| WO | WO 2011/106783 | 9/2011 |
| WO | WO 2011/127088 A3 | 10/2011 |
| WO | WO 2012/032103 | 3/2012 |
| WO | WO 2012/061676 | 5/2012 |
| WO | WO2012/061681 | 5/2012 |
| WO | WO2012/061684 | 5/2012 |
| WO | WO2012/061688 | 5/2012 |
| WO | WO2012/061690 | 5/2012 |
| WO | WO 2012/061741 | 5/2012 |
| WO | WO 2012/061744 | 5/2012 |
| WO | 2012/106407 | 8/2012 |

(56) References Cited

FOREIGN PATENT DOCUMENTS

| WO | WO 2012/134704 A2 | 10/2012 |
|---|---|---|
| WO | WO 2013/003557 | 1/2013 |
| WO | WO 2013/090356 | 6/2013 |
| WO | WO 2013/126521 | 8/2013 |
| WO | WO 2013/126762 | 8/2013 |
| WO | WO 2013/142196 | 9/2013 |
| WO | WO 2014/081449 | 5/2014 |
| WO | WO 2014/117079 | 7/2014 |
| WO | WO 2015/148974 | 10/2015 |
| WO | WO 2016/019075 | 2/2016 |
| WO | WO 2016/090172 | 6/2016 |
| WO | WO 2017/087542 | 5/2017 |

OTHER PUBLICATIONS

Gradinaru et al. "eNpHR: a Natronomonas halorhodopsin enhanced for optogenetic applications" Brain Cell Biol. Aug. 2008;36(1-4): 129-139.*

Ristevski. S. "Making better transgenic models: conditional, temporal, and spatial approaches." Mol Biotechnol. Feb. 2005;29(2):153-63.*

Sigmund. CD. "Viewpoint: are studies in genetically altered mice out of control?" Arterioscler Thromb Vasc Biol. Jun. 2000;20(6):1425-9.*

Ramalho et al. "Mouse genetic corneal disease resulting from transgenic insertional mutagenesis." Br J Ophthalmol. Mar. 2004;88(3):428-32.*

Do Carmo et al. "Modeling Alzheimer's disease in transgenic rats." Mol Neurodegener. Oct. 25, 2013;8:37. doi: 10.1186/1750-1326-8-37.*

Gerits et al. "Optogenetically induced behavioral and functional network changes in primates." Curr Biol. Sep. 25, 2012;22(18):1722-6. (Year: 2012).*

Rein and Deussing "The optogenetic (r)evolution." Mol Genet Genomics. Feb. 2012; 287(2): 95-109. (Year: 2012).*

Han X. "Optogenetics in the nonhuman primate." Prog Brain Res. 2012; 196: 215-233. (Year: 2012).*

Blömer et al. "Applications of gene therapy to the CNS." Hum Mol Genet. 1996;5 Spec No. 1397-404. (Year: 1996).*

Xiong et al., "Interregional connectivity to primary motor cortex revealed using MRI resting state images", Hum Brain Mapp, 1999, 8(2-3):151-156.

Arenkiel, et al. "In vivo light-induced activation of neural circuitry in transgenic mice expressing Channelrhodopsin-2", Neuron, 2007, 54:205-218.

Milella et al. "Opposite roles of dopamine and orexin in quinpirole-induced excessive drinking: a rat model of psychotic polydipsia" Psychopharmacology, 2010, 211:355-366.

Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.

Barchet, et al.; "Challenges and opportunities in CNS delivery of therapeutics for neurodegenerative diseases"; Expert Opinion on Drug Delivery; vol. 6, No. 3, pp. 211-225 (Mar. 16, 2009).

Bowers, et al.; "Genetic therapy for the nervous system"; Human Molecular Genetics; vol. 20, No. 1, pp. R28-R41 (2011).

Castagne, et al.; "Rodent Models of Depression: Forced Swim and Tail Suspension Behavioral Despair Tests in Rats and Mice"; Current Protocols in Pharmacology; Supp. 49, Unit 5.8.1-5.8.14 (Jun. 2010).

Friedman, et al.; "Programmed Acute Electrical Stimulation of Ventral Tegmental Area Alleviates Depressive-Like Behavior"; Neuropsychopharmacology; vol. 34, pp. 1057-1066 (2009).

GenBank Accession No. AC096118.6; Rattus norvegicus clone CH230-11 B15, 1-4, 24-25, Working Draft Sequence, 3 unordered pieces. May 10, 2003.

GenBank Accession No. U79717.1; Rattus norvegicus dopamine 02 receptor 1-4, 24-25 gene, promoter region and exon 1. Jan. 31, 1997.

Haim, et al.; "Gene Therapy to the Nervous System"; Stem Cell and Gene-Based Therapy; Section 2, pp. 133-154 (2006).

Pandya, et al.; "Where in the Brain Is Depression?"; Curr. Psychiatry Rep.; vol. 14, pp. 634-642 (2012).

Stonehouse, et al.; "Caffeine Regulates Neuronal Expression of the Dopamine 2 Receptor Gene"; Molecular Pharmacology; vol. 64, No. 6, pp. 1463-1473 (2003).

Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.

Axoclamp-28 Microelectrode claim theory and operation. Accessed from https://physics.ucsd.edu/neurophysics/Manuals/Axon%20Instruments/Axoclamp-2B_Manual.pdf on Dec. 12, 2014.

Cowan et al., "Targeting gene expression to endothelium in transgenic animals: a comparison of the human ICAM-2, PECAM-1, and endoglin promoters", Xenotransplantation, 2003, vol. 10, pp. 223-231.

Definition of Psychosis (2015).

Ebert et al., "A Moloney MLV-rat somatotropin fusion gene produces biologically active somatotropin in a transgenic pig", Mol. Endocrinology, 1988, vol. 2, pp. 277-283.

Hammer et al., "Spontaneous inflammatory disease in transgenic rats expressing HLA-B27 and Human $\beta_2$m: an animal model of HLA-B27-associated human disorders", Cell, 1990, vol. 63, pp. 1099-1112.

Karra, et al. "Transfection Techniques for Neuronal Cells", The Journal of Neuroscience, 2010, vol. 30, No. 18, pp. 6171-6177.

Kelder et al., "Glycoconjugates in human and transgenic animal milk", Advances in Exp. Med. and Biol., 2001, vol. 501, pp. 269-278.

Mullins et al., "Fulminant hypertension in transgenic rats harbouring the mouse Ren-2 gene", Nature, 1990, vol. 344, pp. 541-544.

Mullins et al., "Expression of the DBA/2J Ren-2 gene in the adrenal gland of transgenic mice", EMBO, 1989, vol. 8, pp. 4065-4072.

Taurog et al., "HLA-B27 in inbred and non-inbred transgenic mice", J. Immunol., 1988, vol. 141, pp. 4020-4023.

Wall, "Transgenic livestock: Progress and prospects for the future", Theriogenology, 1996, vol. 45, pp. 57-68.

Wang, et al., "High-speed mapping of synaptic connectivity using photostimulation in Channelrhodopsin-2 transgenic mice", Proceedings of the National Academy of Sciences, 2007, vol. 104, No. 19, pp. 8143-8148.

Written opinion of PCT Application No. PCT/US2011/059383 (dated May 9, 2012).

Shibasaki et al., "Effects of body temperature on neural activity in the hippocampus: Regulation of resting membrane potentials by transient receptor potential vanilloid 4," The Journal of Neuroscience, 2007, 27(7):1566-1575.

Hikida et al., "Increased sensitivity to cocaine by cholinergic cell ablation in nucleus accumbens", PNAS, Nov. 2001, 98(23): 13351-13354.

Hikida et al., "Acetylcholine enhancement in the nucleus accumbens prevents addictive behaviors of cocaine and morphine", PNAS, May 2003, 100(10):6169-6173.

Kitabatake et al., "Impairment of reward-related learning by cholinergic cell ablation in the striatum", PNAS, Jun. 2003, 100(13):7965-7970.

Tamai, "Progress in Pathogenesis and Therapeutic Research in Retinitis Pigmentosa and Age Related Macular Degeneration", Nippon Ganka Gakkai Zasshi, vol. 108, No. 12, Dec. 2004 (Dec. 2004), pp. 750-769.

Fiala et al., "Optogenetic approaches in neuroscience", Current Biology, Oct. 2010, 20(20):R897-R903.

Gradinaru et al., "Optical deconstruction of parkinsonian neural circuitry", Science, Apr. 2009, 324(5925):354-359.

Liu et al., "Optogenetics 3.0", Cell, Apr. 2010, 141(1):22-24.

Malin et al., "Involvement of the rostral anterior cingulate cortex in consolidation of inhibitory avoidance memory: Interaction with the basolateral amygdala", Neurobiol Learning Mem, 2007, 87(2):295-302.

Mayford et al., "Control of memory formation through regulated expression of CAMKII Transgene", Science, Dec. 1996, 274:1678-1683.

(56) References Cited

OTHER PUBLICATIONS

Schroll et al., "Light-induced activation of distinct modulatory neurons triggers appetitive or aversive learning in *Drosophila larvae*", Current Biology, Sep. 2006, 16(17):1741-1747.
Fox et al., "A gene neuron expression fingerprint of C. elegans embryonic motor neurons", BMC Genomics, 2005, 6(42):1-23.
Nonet, "Visualization of synaptic specializations in live C. elegans with synaptic vesicle protein-GFP fusions", J. Neurosci. Methods, 1999, 89:33-40.
Synapse, Chapter 13, http://michaeldmann.net/mann13.html, downloaded Apr. 2014.
Cazillis et al., "VIP and PACAP induce selective neuronal differentiation of mouse embryonic stem cells", Eur J Neurosci, 2004, 19(4):798-808.
Morelli et al., "Neuronal and glial cell type-specific promoters within adenovirus recombinants restrict the expression of the apoptosis-inducing molecule Fas ligand to predetermined brain cell types, and abolish peripheral liver toxicity", Journal of General Virology, 1999, 80:571-583.
Aebischer, et al. "Long-Term Cross-Species Brain Transplantation of a Polymer-Encapsulated Dopamine-Secreting Cell Line", Experimental Neurology, 1991, vol. 111, pp. 269-275.
Ahmad, et al. "The *Drosophila rhodopsin* cytoplasmic tail domain is required for maintenance of rhabdomere structure." The FASEB Journal, 2007, vol. 21, p. 449-455.
Airan, et al., "Temporally Precise in vivo Control of Intracellular Signaling", 2009, Nature, vol. 458, No. 7241, pp. 1025-1029.
Akirav, et al. "The role of the medial prefrontal cortex-amygdala circuit in stress effects on the extinction of fear", Neural Plasticity, 2007: vol. 2007 Article ID:30873, pp. 1-11.
Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.
Araki, et al. "Site-Directed Integration of the cre Gene Mediated by Cre Recombinase Using a Combination of Mutant lox Sites", Nucleic Acids Research, 2002, vol. 30, No. 19, pp. 1-8.
Aravanis, et al. "An optical neural interface: in vivo control of rodent motor cortex with integrated fiberoptic and optogenetic technology," J. Neural. Eng., 2007, vol. 4(3):S143-S156.
Argos, et al. "The integrase family of site-specific recombinases: regional similarities and global diversity", The EMBO Journal, 1986, vol. 5, No. 2, pp. 433-440.
Bamberg et al. "Light-driven proton or chloride pumping by halorhodopsin." Proc. Natl. Academy Science USA, 1993, vol. 90, No. 2, p. 639-643.
Banghart, et al. "Light-activated ion channels for remote control of neuronal firing". Nature Neuroscience, 2004, vol. 7, No. 12 pp. 1381-1386.
Basil et al. "Is There Evidence for Effectiveness of Transcranial Magnetic Stimulation in the Treatment of Psychiatric Disorders?" Psychiatry, 2005, pp. 64-69.
Bebbington et al., "The use of vectors based on gene amplification for the expression of cloned genes in mammalian cells in DNA cloning" vol. 3, Academic Press, New York, 1987.
Benabid "Future strategies to restore brain functions," Conference proceedings from Medicine Meets Millennium: World Congress of Medicine and Health, 2000, 6 pages.
Benoist et al. "In vivo sequence requirements of the SV40 early promotor region" Nature (London), 1981, vol. 290(5804): pp. 304-310.
Berges et al., "Transduction of Brain by Herpes Simplex Virus Vectors", Molecular Therapy, 2007, vol. 15, No. 1: pp. 20-29.
Berridge et al., "The Versatility and Universality of Calcium Signaling", Nature Reviews: Molecular Cell Biology, 2000, vol. 1: pp. 11-21.
Bocquet et al. "A prokaryotic proton-gated ion channel from the nicotinic acetylcholine receptor family." Nature Letters, 2007, vol. 445, p. 116-119.
Boyden, et al. "Millisecond-timescale, genetically targeted optical control of neural activity" Nature Neuroscience, 2005, vol. 8, No. 9: pp. 1263-1268.
Bi, et al. "Ectopic Expression of a Microbial-Type Rhodopsin Restores Visual Responses in Mice with Photoreceptor Degeneration", Neuron, 2006, vol. 50, No. 1: pp. 23-33.
Bi, et al. "Synaptic Modifications in Cultured Hippocampal Neurons: Dependence on Spike Timing, Synaptic Strength, and Postsynaptic Cell Type", Journal of Neuroscience, 1998, vol. 18, No. 24: pp. 10464-10472.
Blomer et al., "Highly Efficient and Sustained Gene Transfer in Adult Neurons with Lentivirus Vector", Journal of Virology, 1997, vol. 71, No. 9: pp. 6641-6649.
Braun, "Two Light-activated Conductances in the Eye of the Green Alga Volvox carteri", 1999, Biophys J., vol. 76, No. 3, pp. 1668-1678.
Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-17.
Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.
Brown, et al. "Long-term potentiation induced by θ frequency stimulation is regulated by a protein phosphate-operated gate." The Journal of Neuroscience, 2000, vol. 20, No. 21, pp. 7880-7887.
Callaway, et al. "Photostimulation using caged glutamate reveals functional circuitry in living brain slices", Proc. Natl. Acad. Sci. USA., 1993, vol. 90: pp. 7661-7665.
Campagnola et al. "Fiber-coupled light-emitting diode for localized photostimulation of neurons expressing channelrhodopsin-2." Journal of Neuroscience Methods, 2008, vol. 169, Issue 1. Abstract only.
Cardin, et al. "Driving Fast spiking Cells Induces Gamma Rhythm and Controls Sensory Responses", 2009, Nature, vol. 459, vol. 7247, pp. 663-667.
Cenatiempo "Prokaryotic gene expression in vitro: transcription-translation coupled systems", Biochimie, 1986, vol. 68(4): pp. 505-515.
Claudio et al. "Nucleotide and deduced amino acid sequences of Torpedo californica acetylcholine receptor gamma subunit." PNAS USA, 1983, vol. 80, p. 1111-1115.
Collingridge et al. "Inhibitory post-synaptic currents in rat hippocampal CA1 neurones." J. Physiol., 1984, vol. 356, pp. 551-564.
Covington, et al. "Antidepressant Effect of Optogenetic Stimulation of the Medial Prefrontal Cortex." Journal of Neuroscience, 2010, vol. 30(48), pp. 16082-16090.
Crouse, et al. "Expression and amplification of engineered mouse dihydrofolate reductase minigenes" Mol. Cell. Biol. , 1983, vol. 3(2): pp. 257-266.
Cucchiaro et al., "Phaseolus vulgaris leucoagglutinin (PHA-L): a neuroanatomical tracer for electron microscopic analysis of synaptic circuitry in the cat's dorsal lateral geniculate nucleus" J. Electron. Microsc. Tech., 1990, 15(4):352-368.
Cucchiaro et al., "Electron-Microsoft Analysis of Synaptic Input from the Perigeniculate Nucleus to A-Lamine of the Lateral Geniculate Nucleus in Cats", The Journal of Comparative Neurology, 1991, vol. 310, pp. 316-336.
Cui, et al., "Electrochemical deposition and characterization of conducting polymer polypyrrole/PSS on multichannel neural probes," Sensors and Actuators, 2001, vol. 93(1): pp. 8-18.
Date, et al. "Grafting of Encapsulated Dopamine-Secreting Cells in Parkinson's Disease: Long-Term Primate Study", Cell Transplant, 2000, vol. 9, pp. 705-709.
Dalva, et al. "Rearrangements of Synaptic Connections in Visual Cortex Revealed by Laser Photostimulation", Science, 1994, vol. 265, pp. 255-258.
Dederen, et al. "Retrograde neuronal tracing with cholera toxin B subunit: comparison of three different visualization methods", Histochemical Journal, 1994, vol. 26, pp. 856-862.

(56) References Cited

OTHER PUBLICATIONS

De Foubert et al. "Fluoxetine-Induced Change in Rat Brain Expression of Brain-Derived Neurotrophic Factor Varies Depending on Length of Treatment," Neuroscience, 2004, vol. 128, pp. 597-604.
Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.
Deisseroth et al., "Translocation of Calmodulin to the Nucleus Supports CREB Phosphorylation in Hippocampal Neurons", Nature, 1998, vol. 392, pp. 198-202.
Deisseroth et al., "Signaling from Synapse to Nucleus: the logic Behind the Mechanisms", Currrent Opinion in Neurobiology, 2003, vol. 13, pp. 354-365.
Deisseroth et al., "Excitation-neurogenesis Coupling in Adult Neural Stem/Progenitor Cells", 2004, Neuron, vol. 42, pp. 535-552.
Deisseroth "Next-generation optical technologies for illuminating genetically targeted brain circuits," The Journal of Neuroscience, 2006, vol. 26, No. 41, pp. 10380-10386.
Denk, W., et al. "Anatomical and functional imaging of neurons using 2-photon laser scanning microscopy", Journal of Neuroscience Methods, 1994, vol. 54, pp. 151-162.
Ditterich, et al. "Microstimulation of visual cortex affects the speed of perceptual decisions", 2003, Nature Neuroscience, vol. 6, No. 8, pp. 891-898.
Dittgen, et al. "Lentivirus-based genetic manipulations of cortical neurons and their optical and electrophysiological monitoring in vivo", PNAS, 2004, vol. 10I, No. 52, pp. 18206-18211.
Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.
Ensell, et al. "Silicon-based microelectrodes for neurophysiology, micromachined from silicon-on-insulator wafers," Med. Biol. Eng. Comput., 2000, vol. 38, pp. 175-179.
Eisen, "Treatment of amyotrophic lateral sclerosis", Drugs Aging, 1999; vol. 14, No. 3, pp. 173-196.
Ernst, et al. "Photoactivation of Channelrhodopsin", 2008, vol. 283, No. 3, pp. 1637-1643.
Evanko "Optical excitation yin and yang" Nature Methods, 2007, 4:384.
Esposito et al. "The integrase family of tyrosine recombinases: evolution of a conserved active site domain" , Nucleic Acids Research, 1997, vol. 25, No. 18, pp. 3605-3614.
Fabian et al. "Transneuronal transport of lectins" Brain Research, 1985, vol. 344, pp. 41-48.
Falconer et al. "High-throughput screening for ion channel modulators," Journal of Biomolecular Screening, 2002, vol. 7, No. 5, pp. 460-465.
Farber, et al. "Identification of Presynaptic Neurons by Laser Photostimulation", Science, 1983, vol. 222, pp. 1025-1027.
Feng, et al. "Imaging Neuronal Subsets in Transgenic Mice Expressing Multiple Spectral Variants of GFP", Neuron, 2000, vol. 28, pp. 41-51.
Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.
Fitzsimons et al., "Promotors and Regulatory Elements that Improve Adeno-Associated Virus Transgene Expression in the Brain", 2002, Methods, vol. 28, pp. 227-236.
Foster, "Bright blue times", Nature, 2005, vol. 433, pp. 698-699.
Genbank Accession No. DQ094781 (Jan. 15, 2008).
Gelvich et al. "Contact flexible microstrip applicators (CFMA) in a range from microwaves up to short waves," IEEE Transactions on Biomedical Engineering, 2002, vol. 49, Issue 9: 1015-1023.
Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from *Bacillus subtilis* DNA" Gene, 1984, vol. 32(1-2): pp. 11-20.

Glick et al. "Factors affecting the expression of foreign proteins in *Escherichia coli*", Journal of Industrial Microbiology, 1987, vol. 1(5): pp. 277-282.
Goekoop, R. et al. "Cholinergic challenge in Alzheimer patients and mild cognitive impairment differentially affects hippocampal activation—a pharmacological fMRI study." Brain, 2006, vol. 129, pp. 141-157.
Gold, et al. "Representation of a perceptual decision in developing oculomotor commands", Nature, 2000, vol. 404, pp. 390-394.
Gonzalez, et al. "Cell-Based Assays and Instrumentation for Screening Ion-Channel Targets", DDT, 1999, vol. 4, No. 9, pp. 431439.
Gordon, et al. "Regulation of Thy-1 Gene Expression in Transgenic Mice", Cell, 1987, vol. 50, pp. 445-452.
Gorelova et al., "The course of neural projection from the prefrontal cortex to the nucleus accumbens in the rat ", Neuroscience, 1997, vol. 76, No. 3, pp. 689-706.
Gottesman et al."Bacterial regulation: global regulatory networks," Ann. Rev. Genet. , 1984, vol. 18, pp. 415-441.
Gradinaru, et al. "ENpHR: a Natronomonas Halorhodopsin Enhanced for Optogenetic Applications", 2008, Brain Cell Biol., vol. 36 (1-4), pp. 129-139.
Greenberg, et al. "Three-year outcomes in deep brain stimulation for highly resistant obsessive-compulsive disorder," Neuropsychopharmacology, 2006, vol. 31, pp. 2384-2393.
Gregory, et al. "Integration site for *Streptomyces* phage φBT1 and development of site-specific integrating vectors", Journal of Bacteriology, 2003, vol. 185, No. 17, pp. 5320-5323.
Groth et al. "Phage integrases: biology and applications," Journal of Molecular Biology, 2004, vol. 335, pp. 667-678.
Groth, et al. "A phage integrase directs efficient site-specific integration in human cells", PNAS, 2000, vol. 97, No. 11, pp. 5995-6000.
Guatteo, et al. "Temperature sensitivity of dopaminergic neurons of the substantia nigra pars compacta: Involvement of transient receptor potential channels," Journal of Neurophysiol. , 2005, vol. 94, pp. 3069-3080.
Gulick, et al. "Transfection using DEAE-Dextran" Supplement 40, Current Protocols in Molecular Biology, 1997, Supplement 40, 9.2.1-9.2.10.
Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.
Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.
Hamer, et al. "Regulation In Vivo of a cloned mammalian gene: cadmium induces the transcription of a mouse metallothionein gene in SV40 vectors," Journal of Molecular Applied Genetics, 1982, vol. 1, No. 4, pp. 273-288.
Hausser, et al. "Tonic Synaptic Inhibition Modulates Neuronal Output Pattern and Spatiotemporal Synaptic Integration", Neuron, 1997, vol. 19, pp. 665-678.
Hegemann et al., "All-trans Retinal Constitutes the Functional Chromophore in Chlamydomonas rhodopsin", Biophys. J. , 1991, vol. 60, pp. 1477-1489.
Herlitze, et al., "New Optical Tools for Controlling Neuronal Activity", 2007, Curr Opin Neurobiol, vol. 17, No. 1, pp. 87-94.
Herry, et al. "Switching on and off fear by distinct neuronal circuits," Nature, 2008, vol. 454, pp. 600-606.
Hildebrandt et al, "Bacteriorhodopsin expressed in *Schizosaccharomyces pombe* pumps protons through the plasma membrane," PNAS, 1993, vol. 90, pp. 3578-3582.
Hirase, et al. "Multiphoton stimulation of neurons", J Neurobiol, 2002, vol. 5I, No. 3: pp. 237-247.
Hodaie, et al., "Chronic Anterior Thalamus Stimulation for Intractable Epilepsy," Epilepsia, 2002, vol. 43, pp. 603-608.
Hoffman et al., "K+ Channel Regulation of Signal Propagation in Dendrites of Hippocampal Pyramidal Neurons", 1997, Nature, vol. 387: pp. 869-874.

(56) References Cited

OTHER PUBLICATIONS

Hosokawa, T. et al. "Imaging spatio-temporal patterns of long-term potentiation in mouse hippocampus." Philos. Trans. R. Soc. Lond. B., 2003, vol. 358, pp. 689-693.
Hynynen, et al. "Clinical applications of focused ultrasound—The brain." Int. J. Hyperthermia, 2007, vol. 23, No. 2: pp. 193-202.
International Search Report for International Application No. PCT/US2009/053474, dated Oct. 8, 2009.
Isenberg et al. "Cloning of a Putative Neuronal Nicotinic Aceylcholine Receptor Subunit," Journal of Neurochemistry, 1989, pp. 988-991.
Jekely, "Evolution of Phototaxis", 2009, Phil. Trans. R. Soc. B, vol. 364, pp. 2795-2808.
Johansen, et al., "Optical Activation of Lateral Amygdala Pyramidal Cells Instructs Associative Fear Learning", 2010, PNAS, vol. 107, No. 28, pp. 12692-12697.
Johnston et al. "Isolation of the yeast regulatory gene GAL4 and analysis of its dosage effects on the galactose/melibiose regulon," PNAS, 1982, vol. 79, pp. 6971-6975.
Kandel, E.R., et al. "Electrophysiology of Hippocampal Neurons: I. Sequential Invasion and Synaptic Organization," J Neurophysiol, 1961, vol. 24, pp. 225-242.
Kandel, E.R., et al. "Electrophysiology of Hippocampal Neurons: II. After-Potentials and Repetitive Firing", J Neurophysiol., 1961, vol. 24, pp. 243-259.
Karreman et al. "On the use of double FLP recognition targets (FRTs) in the LTR of retroviruses for the construction of high producer cell lines", Nucleic Acids Research, 1996, vol. 24, No. 9: pp. 1616-1624.
Kato et al. "Present and future status of noninvasive selective deep heating using RF in hyperthermia." Med & Biol. Eng. & Comput 31 Supp: S2-11, 1993. Abstract. p. S2 only.
Katz, et al. "Scanning laser photostimulation: a new approach for analyzing brain circuits," Journal of Neuroscience Methods, 1994, vol. 54, pp. 205-218.
Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.
Khosravani et al., "Voltage-Gated Calcium Channels and Idiopathic Generalized Epilepsies", Physiol. Rev., 2006, vol. 86: pp. 941-966.
Kianianmomeni, et al. "Channelrhodopsins of Volvox carteri are Photochromic Proteins that are Specifically Expressed in Somatic Cells under Control of Light, Temperature, and the Sex Inducer", 2009, Plant Physiology, vol. 151, No. 1, pp. 347-366.
Kim et al., "Light-Driven Activation of β2-Adrenergic Receptor Signaling by a Chimeric Rhodopsin Containing the β2-Adrenergic Receptor Cytoplasmic Loops," Biochemistry, 2005, vol. 44, No. 7, pp. 2284-2292.
Kingston et al. "Transfection of DNA into Eukaryotic Cells," Supplement 63, Current Protocols in Molecular Biology, 1996, 9.1.1-9.1.11, 11 pages.
Kingston et al. "Transfection and Expression of Cloned DNA," Supplement 31, Current Protocols in Immunology, 1999, 10.13.1-10.13.9.
Kita, H. et al. "Effects of dopamine agonists and antagonists on optical responses evoked in rat frontal cortex slices after stimulation of the subcortical white matter," Exp. Brain Research, 1999, vol. 125, pp. 383-388.
Kitayama, et al. "Regulation of neuronal differentiation by N-methyl-D-aspartate receptors expressed in neural progenitor cells isolated from adult mouse hippocampus," Journal of Neurosci Research, 2004, vol. 76, No. 5: pp. 599-612.
Klausberger, et al. "Brain-state- and cell-type-specific firing of hippocampal interneurons in vivo", Nature, 2003, vol. 421: pp. 844-848.
Kocsis et al. "Regenerating Mammalian Nerve Fibres: Changes in Action Potential Wavefrom and Firing Characteristics Following Blockage of Potassium Conductance", 1982, Proc. R. Soc. Lond., vol. B 217: pp. 77-87.

Knopfel, et al. "Optical Probin of Neuronal Circuit Dynamics: Gentically Encoded Versus Classical Fluorescent Sensors", 2006, Trends Neurosci, vol. 29, No. 3, pp. 160-166.
Kuhlman et al. (2008) "High-Resolution Labeling and Functional Manipulation of Specific Neuron Types in Mouse Brain by Cre-Activated Viral Gene Expression" PLoS One, 2005, vol. 3, No. 4, pp. 1-11.
Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.
Landy, A. "Mechanistic and structural complexity in the site-specific recombination pathways of Int and FLP", Current Opinion in Genetics and Development, 1993, vol. 3, pp. 699-707.
Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.
Lee et al., "Potassium Channel Gone Therapy Can Prevent Neuron Deatch Resulting from Necrotic and Apoptotic Insults", Journal of Neurochemistry, 2003, vol. 85: pp. 1079-1088.
Levitan et al. "Surface Expression of Kv1 Voltage-Gated K+ Channels Is Governed by a C-terminal Motif," Trends Cardiovasc. Med., 2000, vol. 10, No. 7, pp. 317-320.
Li et al. "Fast noninvasive activation and inhibition of neural and network activity by vertebrate rhodopsin and green algae channelrhodopsin." PNAS, 2005, vol. 102, No. 49, p. 17816-17821.
Lim et al., "A Novel Targeting Signal for Proximal Clustering of the Kv2.1K+ Channel in Hippocampal Neurons", Neuron, 2000, vol. 25: pp. 385-397.
Lima, et al. "Remote Control of Behavior through Genetically Targeted Photostimulation of Neurons", Cell, 2005, vol. 121: pp. 141-152.
Liman, et al. "Subunit Stoichiometry of a Mammalian K+ Channel Determined by Construction of Multimeric cDNAs," Neuron, 1992, vol. 9, pp. 861-871.
Louis et al. "Cloning and sequencing of the cellular-viral junctions from the human adenovirus type 5 transformed 293 cell line," Virology, 1997, vol. 233, pp. 423-429.
Luecke, et al. "Structural Changes in Bacteriorhodopsin During Ion Transport at 2 Angstrom Resolution," Science, 1999, vol. 286, pp. 255-260.
Lyznik, et al. "FLP-mediated recombination of FRT sites in the maize genome," Nucleic Acids Research, 1996, vol. 24, No. 19: pp. 3784-3789.
Ma et al. "Role of ER Export Signals in Controlling Surface Potassium Channel Numbers," Science, 2001, vol. 291, pp. 316-319.
Mann et at. "Perisomatic Feedback Inhibition Underlies Cholinergically Induced Fast Network Oscillations in the Rat Hippocampus in Vitro," Neuron, 2005, vol. 45, 2005, pp. 105-117.
Mattson, "Apoptosis in Neurodegenerative Disorders", Nature Reviews, 2000, vol. 1: pp. 120-129.
Mayberg et al. "Deep Brain Stimulation for Treatment-Resistant Depression," Focus, 2008, vol. VI, No. 1, pp. 143-154.
McAllister, "Cellular and Molecular Mechanisms of Dendrite Growth", 2000, Cereb Cortex, vol. 10, No. 10, pp. 963-973.
McKnight "Functional relationships between transcriptional control signals of the thymidine kinase gene of herpes simplex virus", Cell, 1982, vol. 31 pp. 355-365.
Melyan, Z., et al. "Addition of human melanopsin renders mammalian cells Photoresponsive", Nature, 2005, vol. 433: pp. 741-745.
Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.
Meyer, et al. "High density interconnects and flexible hybrid assemblies for active biomedical implants," IEEE Transactions on Advanced Packaging, 2001, vol. 24, No. 3, pp. 366-372.
Monje et al., "Irradiation Induces Neural Precursor-Cell Dysfunction", Natural Medicine, 2002, vol. 8, No. 9, pp. 955-962.

(56) References Cited

OTHER PUBLICATIONS

Mortensen et al. "Selection of Transfected Mammalian Cells," Supplement 86, Current Protocols in Molecular Biology, 1997, 9.5.1-09.5.19.
Nacher, et al. "NMDA receptor antagonist treatment increases the production of newneurons in the aged rat hippocampus", Neurobiology of Aging, 2003,vol. 24, No. 2: pp. 273-284.
Nagel et al. "Functional Expression of Bacteriorhodopsin in Oocytes Allows Direct Measurement of Voltage Dependence of Light Induced H+ Pumping," FEBS Letters, 1995, vol. 377, pp. 263-266.
Nagel, et al. "Channelrhodopsin-I: a light-gated proton channel in green algae", Science, 2002, vol. 296: pp. 2395-2398.
Nagel, et al. "Channelrhodopsin-2, a directly light-gated cation-selective membrane channel", PNAS, 2003, vol. 100, No. 24: pp. 13940-13945.
Nakagami, et al. "Optical Recording of Trisynaptic Pathway in Rat Hippocampal Slices with a Voltage-Sensitive Dye" Neuroscience, 1997, vol. 81, No. 1, pp. 1-8.
Naqvi, et al. "Damage to the insula disrupts addiction to cigarette smoking," Science; 2007, vol. 315 pp. 531-534.
Natochin, et al. "Probing rhodopsin-transducin interaction using *Drosophila* Rh1-bovine rhodopsin chimeras," Vision Res., 2006, vol. 46, No. 27: pp. 4575-4581.
Nirenberg, et al. "The Light Response of Retinal Ganglion Cells is Truncated by a Displaced Amacrine Circuit", Neuron, 1997, vol. 18: pp. 637-650.
Nunes-Duby, et al. "Similarities and differences among 105 members of the Int family of site-specific recombinases", Nucleic Acids Research, 1998, vol. 26, No. 2: pp. 391-406.
O'Gorman et al. "Recombinase-mediated gene activation and site-specific integration in mammalian cells", Science, 1991, 251(4999): pp. 1351-1355.
Olivares (2001) "Phage R4 integrase mediates site-specific integration in human cells", Gene, 2001, vol. 278, pp. 167-176.
Ory, et al. "A stable human-derived packaging cell line for production of high titer retrovirus/vesicular stomatitis virus G pseudotypes," PNAS, 1996, vol. 93: pp. 11400-11406.
Palmer et al., "The Adult Rat Hippocampus Contains Primordial Neural Stem Cells", Molecular and Cellular Neuroscience, 1997, vol. 8, pp. 389-404.
Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.
Pan et al. "Functional Expression of a Directly Light-Gated Membrane Channel in Mammalian Retinal Neurons: A Potential Strategy for Restoring Light Sensitivity to the Retina After Photoreceptor Degeneration," Investigative Opthalmology & Visual Science, 2005, 46 E-Abstract 4631. Abstract only.
Panda, et al. "Illumination of the Melanopsin Signaling Pathway", Science, 2005, vol. 307: pp. 600-604.
Pape, et al., "Plastic Synaptic Networks of the Amygdala for the Acquisition, Expression, and Extinction of Conditioned Fear", 2010, Physiol Rev, vol. 90, pp. 419-463.
Paulhe et al. "Specific Endoplasmic Reticulum Export Signal Drives Transport of Stem Cell Factor (Kitl) to the Cell Surface," The Journal of Biological Chemistry, 2004, vol. 279, No. 53, p. 55545-55555.
Pear "Transient Transfection Methods for Preparation of High-Titer Retroviral Supernatants" Supplement 68, Current Protocols in Molecular Biology, 1996, 9.1 1 .I-9.1 1 .I 8.
Peterlin, et al. "Optical probing of neuronal circuits with calcium indicators," PNAS, 2000, vol. 97, No. 7: pp. 3619-3624.
Petersen et al. "Spatiotemporal Dynamics of Sensory Responses in Layer 2/3 of Rat Barrel Cortex Measured In Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.
Petrecca, et al. "Localization and Enhanced Current Density of the Kv4.2 Potassium Channel by Interaction with the Actin-Binding Protein Filamin," The Journal of Neuroscience, 2000, vol. 20, No. 23, pp. 8736-8744.
Pettit, et al. "Local Excitatory Circuits in the Intermediate Gray Layer of the Superior Colliculus", J Neurophysiol., 1999, vol. 81, No. 3: pp. 1424-1427.
Potter, "Transfection by Electroporation." Supplement 62, Current Protocols in Molecular Biology, 1996, 9.3.1-9.3.6.
Pouille, et al. "Routing of spike series by dynamic circuits in the hippocampus", Nature, 2004, vol. 429: pp. 717-723.
Qiu et al. "Induction of photosensitivity by heterologous expression of melanopsin", Nature, 2005, vol. 433: pp. 745-749.
Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.
Randic, et al. "Long-term Potentiation and Long-term Depression of Primary Afferent Neurotransmission in the Rat Spinal Cord", 1993, Journal of Neuroscience, vol. 13, No. 12, pp. 5228-5241.
Rathnasingham et al., "Characterization of implantable microfabricated fluid delivery devices," IEEE Transactions on Biomedical Engineering, 2004, vol. 51, No. 1: pp. 138-145.
Ritter, et al., "Monitoring Light-induced Structural Changes of Channelrhodopsin-2 by UV-Visible and Fourier Transform Infared Spectroscopy", 2008, The Journal of Biological Chemistry, vol. 283, No. 50, pp. 35033-35041.
Rivera et al., "BDNF-Induced TrkB Activation Down-Regulates the K+-Cl-cotransporter KCC2 and Impairs Neuronal Cl-Extrusion", The Journal of Cell Biology, 2002, vol. 159: pp. 747-752.
Rosenkranz, et al. "The prefrontal cortex regulates lateral amygdala neuronal plasticity and responses to previously conditioned stimuli", J. Neurosci., 2003, vol. 23, No. 35: pp. 11054-11064.
Rousche, et al., "Flexible polyimide-based intracortical electrode arrays with bioactive capability," IEEE Transactions on Biomedical Engineering, 2001, vol. 48, No. 3, pp. 361-371.
Rubinson et at. "A lentivirus-based system to functionally silence genes in primary mammalian cells, stem cells and transgenic mice by RNA interference," Nature Genetics, 2003, vol. 33, p. 401-406.
Rudiger et at. "Specific arginine and threonine residues control anion binding and transport in the light-driven chloride pump halorhodopsin," The EMBO Journal, 1997, vol. 16, No. 13, pp. 3813-3821.
Salzman, et al. "Cortical microstimulation influences perceptual judgements of motion direction", Nature, 1990, vol. 346, pp. 174-177.
Sajdyk, et al., "Excitatory Amino Acid Receptors in the Basolateral Amygdala Regulate Anxiety Responses in the Social Interaction Test", Brain Research, 1997, vol. 764, pp. 262-264.
Sato et al. "Role of Anion-binding Sites in cytoplasmic and extracellular channels of *Natronomonas pharaonis* halorhodopsin," Biochemistry, 2005. vol. 44, pp. 4775-4784.
Sauer "Site-specific recombination: developments and applications," Current Opinion in Biotechnology, 1994, vol. 5, No. 5: pp. 521-527.
Schiff, et al. "Behavioral improvements with thalamic stimulation after severe traumatic brain injury," Nature, 2007, vol. 448, pp. 600-604.
Schlaepfer et al. "Deep Brain stimulation to Reward Circuitry Alleviates Anhedonia in Refractory Major Depresion," Neuropsychopharmacology, 2008, vol. 33, pp. 368-377.
Sclimenti, et al. "Directed evolution of a recombinase for improved genomic integration at a native human sequence," Nucleic Acids Research, 2001, vol. 29, No. 24: pp. 5044-5051.
Shepherd, et al. "Circuit Analysis of Experience-Dependent Plasticity in the Developing Rat Barrel Cortex", Neuron, 2003, vol. 38: pp. 277-289.
Shibasaki et al. "Effects of body temperature on neural activity in the hippocampus: Regulation of resting membrane potentials by transient receptor potential vanilloid 4," The Journal of Neuroscience, 2007, vol. 27, No. 7: pp. 1566-1575.

(56) References Cited

OTHER PUBLICATIONS

Silver, et al. "Amino terminus of the yeast GAL4 gene product is sufficient for nuclear localization" PNAS, 1984, vol. 81, No. 19: pp. 5951-5955.
Singer et al. "Elevated Intrasynaptic Dopamine Release in Tourette's Syndrome Measured by PET," American Journal of Psychiatry, 2002, vol. 159: pp. 1329-1336.
Slimko et al., "Selective Electrical Silencing of Mammalian Neurons In Vitro by the use of Invertebrate Ligand-Gated Chloride Channels", The Journal of Neuroscience, 2002, vol. 22, No. 17: pp. 7373-7379.
Smith et al. "Diversity in the serine recombinases", Molecular Microbiology, 2002, vol. 44, No. 2: pp. 299-307.
Song et al. "Differential Effect of TEA on Long-Term Synaptic Modification in Hippocampal CA1 and Dentate Gyrus in vitro." Neurobiology of Learning and Memory, 2001, vol. 76, No. 3, pp. 375-387.
Song, "Genes responsible for native depolarization-activated K+ currents in neurons," Neuroscience Research, 2002, vol. 42, pp. 7-14.
Stark, et al. "Catalysis by site-specific recombinases," Trends Genet., 1992, vol. 8, No. 12: pp. 432-439.
Stockklausner et al. "A sequence motif responsible for ER export and surface expression of Kir2.0 inward rectifier K+ channels," FEBS Letters, 2001, vol. 493, pp. 129-133.
Stoll, et al. "Phage TP901-I site-specific integrase functions in human cells," Journal of Bacteriology, 2002, vol. 184, No. 13: pp. 3657-3663.
Swanson, "Lights, Opsins, Action! Optogenetics Brings Complex Neuronal Circuits into Sharper Focus", 2009, The Dana Foundation, [URL: http://www.dana.org/news/features/detail.aspx?id=24236], PDF File, pp. 1-3.
Swiss-Prot_Q2QCJ4, Opsin 1, Oct. 31, 2006, URL: http://www.ncbi.nlm.nig.gov/protein/Q2QCJ4.
Takahashi, et al."Diversion of the Sign of Phototaxis in a *Chlamydomonas reinhardtii* Mutant Incorporated with Retinal and Its Analogs," FEBS Letters, 1992, vol. 314, No. 3, pp. 275-279.
Tatarkiewicz, et al. "Reversal of Hyperglycemia in Mice After Subcutaneous Transplantation of Macroencapsulated Islets", Transplantation, 1999, vol. 67, No. 5: pp. 665-671.
Tottene et al., "Familial Hemiplegic Migraine Mutations Increase $Ca^{2+}$ Influx Through Single Human $Ca_v2.1$ Current Density in Neurons", PNAS USA, 2002, vol. 99, No. 20: pp. 13284-13289.
Tsau et al. "Distributed Aspects of the Response to Siphon Touch in Aplysia: Spread of Stimulus Information and Cross-Correlation Analysis," The Journal of Neuroscience, 1994, vol. 14, No. 7, pp. 4167-4184.
[No Authors Listed] "Two bright new faces in gene therapy," Nature Biotechnology, 1996, vol. 14: p. 556.
Tye et. al., "Amygdala circuitry mediating reversible and bidirectional control of anxiety", Nature, 2011, vol. 471(7338): pp. 358-362.
Tye et. al., Supplementary Materials: "An optically-resolved microcircuit for bidirectional anxiety control", Nature, 2011, vol. 471(7338): pp. 358-362.
"SubName: Full=Channelrhodopsin-1", retrieved from EBI accession No. UNIPROT: B4Y103. Database accession No. B4Y103. Sep. 23, 2008.
Ulmanen, et al. "Transcription and translation of foreign genes in *Bacillus subtilis* by the aid of a secretion vector," Journal of Bacteriology, 1985, vol. 162, No. 1: pp. 176-182.
Van Der Linden, "Functional brain imaging and pharmacotherapy in social phobia: single photon emission computed tomography before and after Treatment with the selective serotonin reuptake inhibitor citalopram," Prog Neuro-psychopharmacol Biol Psychiatry, 2000, vol. 24, No. 3: pp. 419-438.
Vanin, et al. "Development of high-titer retroviral producer cell lines by using Cre-mediated recombination," Journal of Virology, 1997, vol. 71, No. 10: pp. 7820-7826.

Vetter, et al. "Development of a Microscale Implantable Neural Interface (MINI) Probe System," Proceedings of the 2005 IEEE, Engineering in Medicine and Biology 27th Annual Conference, Shanghai, China, Sep. 1-4, 2005.
Wagner, "Noninvasive Human Brain Stimulation", Annual Rev. Biomed. Eng. 2007. 9:I9.I-19.39.
Ward, et al. "Construction and characterisation of a series of multi-copy promoter-probe plasmid vectors for *Streptomyces* using the aminoglycoside phosphotransferase gene from Tn5 as indicator", 1986, Mol. Gen. Genet., vol. 203: pp. 468-478.
Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.
Wang et al. "Direct-current Nanogenerator Driven by Ultrasonic Waves," Science, 2007, vol. 316, pp. 102-105.
Wang et. al., "High-speed mapping of synaptic connectivity using photostimulation in Channelrhodopsin-2 transgenic mice", PNAS, 2007, vol. 104, No. 19, pp. 8143-8148.
Weick et al. "Interactions with PDZ Proteins Are Required for L-Type Calcium Channels to Activate cAMP Response Element-Binding Protein-Dependent Gene Expression," The Journal of Neuroscience, 2003, vol. 23, No. 8, pp. 3446-3456.
Wells et al. "Application of Infrared light for in vivo neural stimulation," Journal of Biomedical Optics, 2005, vol. 10(6), pp. 064003-1-064003-12.
Witten et. al., Supporting Online Material for: "Cholinergic Interneurons Control Local Circuit Activity and Cocaine Conditioning", Science, 2010, vol. 330: 17 pages.
Witten et. al., "Cholinergic Interneurons Control Local Circuit Activity and Cocaine Conditioning", Science, 2010, vol. 330, No. 6011: pp. 1677-1681.
Yamazoe, et al. "Efficient generation of dopaminergic neurons from mouse embryonic stem cells enclosed in hollow fibers", Biomaterials, 2006, vol. 27, pp. 4871-4880.
Yan et al., "Cloning and Characterization of a Human β, β-Carotene-15, 15'-Dioxygenase that is Highly Expressed in the Retinal Pigment Epithelium", Genomics, 2001, vol. 72: pp. 193-202.
Yizhar et. al., "Neocortical excitation/inhibition balance in information processing and social dysfunction", Nature, 2011, vol. 477, pp. 171-178; and Supplemental Materials; 41 pages.
Yoon, et al., "A micromachined silicon depth probe for multichannel neural recording," IEEE Transactions Biomedical Engineering, 2000, vol. 47, No. 8, pp. 1082-1087.
Yoshimura, et al. "Excitatory cortical neurons form fine-scale functional networks", Nature, 2005, vol. 433: pp. 868-873.
Zacharias et al. "Recent advances in technology for measuring and manipulating cell signals," Current Opinion in Neurobiology, 2000, vol. 10: pp. 416-421.
Zemelman, et al. "Selective Photostimulation of Genetically ChARGed Neurons", Neuron, 2002, vol. 33: pp. 15-22.
Zemelman, et al. "Photochemical gating of heterologous ion channels: Remote control over genetically designated populations of neurons", PNAS, 2003, vol. 100, No. 3: pp. 1352-1357.
Zhang, et al. "Channelrhodopsin-2 and optical control of excitable cells," Nature Methods, 2006, vol. 3, No. 10, pp. 785-792.
Zhang, et al. "Red-Shifted Optogenetic Excitation: a Tool for Fast Neural Control Derived from *Volvox carteri*", Nature Neurosciences, 2008, vol. 11, No. 6, pp. 631-633.
Zhang "Multimodal fast optical interrogation of neural circuitry," Nature, 2007, vol. 446, pp. 633-641.
Zrenner, E., "Will Retinal Implants Restore Vision?" Science, 2002, vol. 295, No. 5557, pp. 1022-1025.
Zufferey, et al. "Self-Inactivating Lentivirus Vector for Safe and Efficient In Vivo Gene Delivery", Journal of Virology, 1998, vol. 72, No. 12, pp. 9873-9880.
Berke, et al. "Addiction, Dopamine, and the Molecular Mechanisms of Memory", Molecular Plasticity, 2000, vol. 25: pp. 515-532.
Goshen et al. "Dynamics of Retrieval Strategies for Remote Memories", Cell, 2011, vol. 147: pp. 678-589.
Jimenez S.A & Maren S. et al/ "Nuclear disconnection within the amygdala reveals a pathway to fear", Learning Memory, 2009, vol. 16: pp. 766-768.

(56) References Cited

OTHER PUBLICATIONS

Ehrlich I. et al. "Amygdala inhibitory circuits and the control of fear memory", Neuron, 2009. Friedrich Meischer Institute, vol. 62: pp. 757-771.
Berndt et al. "Bi-stable neural state switches", Nature Neuroscience, 2009, vol. 12, No. 2: pp. 229-234.
Simmons et al. "Localization and function of NK3 subtype Tachykinin receptors of layer pyramidal neurons of the guinea-pig medial prefrontal cortex", Neuroscience, 2008, vol. 156, No. 4: pp. 987-994.
Davis; "The many faces of epidermal growth factor repeats," The New Biologist; vol. 2, No. 5, pp. 410-419 (1990).
De Palma, et al.; "In Vivo Targeting of Tumor Endothelial Cells by Systemic Delivery of Lentiviral Vectors"; Human Gene Therapy; vol. 14, pp. 1193-1206 (Aug. 10, 2003).
EBI accession No. Uniprot: A7U0Y6; "SubName: Full= Bacteriorhodopsin"; (Aug. 10, 2010).
Ihara, et al.; "Evolution of the Archaeal Rhodopsins: Evolution Rate Changes by Gene Duplication and Functional Differentiation"; J. Mol. Biol.; vol. 285, pp. 163-174 (1999).
Kaiser; "Clinical research. Death prompts a review of gene therapy vector"; Science; 317(5838):580 (Aug. 3, 2007).
Kay; "State-of-the-art gene-based therapies: the road ahead"; Nature Reviews Genetics; vol. 12, pp. 316-328 (May 2011).
Singer; "Light Switch for Bladder Control"; Technology Review; pp. 1-2 (Sep. 14, 2009).
Skolnick, et al.; "From genes to protein structure and function: novel applications of computational approaches in the genomic era"; Trends Biotechnol; vol. 18, No. 1, pp. 34-39 (Jan. 2000).
Soofiyani, et al.; "Gene Therapy, Early Promises, Subsequent Problems, and Recent Breakthroughs"; Advanced Pharmaceutical Bulletin; vol. 3, No. 2, pp. 249-255 (2013).
U.S. Appl. No. 13/555,981, filed Jul. 23, 2012, Deisseroth, et al.
U.S. Appl. No. 13/622,809, filed Sep. 19, 2012, Deisseroth, et al.
U.S. Appl. No. 13/623,612, filed Sep. 20, 2012, Deisseroth, et al.
U.S. Appl. No. 13/718,243, filed Dec. 18, 2012, Deisseroth, et al.
U.S. Appl. No. 13/763,119, filed Feb. 8, 2013, Deisseroth, et al.
U.S. Appl. No. 13/763,132, filed Feb. 8, 2013, Deisseroth, et al.
U.S. Appl. No. 13/772,732, filed Feb. 21, 2013, Deisseroth, et al.
U.S. Appl. No. 13/847,653, filed Mar. 20, 2013, Deisseroth, et al.
U.S. Appl. No. 13/847,785, filed Mar. 20, 2013, Deisseroth, et al.
U.S. Appl. No. 13/849,913, filed Mar. 25, 2013, Deisseroth, et al.
U.S. Appl. No. 13/850,426, filed Mar. 26, 2013, Deisseroth, et al.
U.S. Appl. No. 13/850,428, filed Mar. 26, 2013, Deisseroth, et al.
U.S. Appl. No. 13/850,436, filed Mar. 26, 2013, Deisseroth, et al.
U.S. Appl. No. 13/850,709, filed Mar. 26, 2013, Deisseroth, et al.
U.S. Appl. No. 13/854,750, filed Apr. 1, 2013, Deisseroth, et al.
U.S. Appl. No. 13/854,754, filed Apr. 1, 2013, Deisseroth, et al.
U.S. Appl. No. 13/855,413, filed Apr. 2, 2013, Deisseroth, et al.
U.S. Appl. No. 13/875,966, filed May 2, 2013, Deisseroth, et al.
U.S. Appl. No. 13/882,566, filed Nov. 4, 2011, Deisseroth, et al.
U.S. Appl. No. 13/882,670, filed Nov. 4, 2011, Deisseroth, et al.
U.S. Appl. No. 13/882,703, filed Nov. 4, 2011, Deisseroth, et al.
U.S. Appl. No. 13/882,705, filed Nov. 4, 2011, Deisseroth, et al.
U.S. Appl. No. 13/882,719, filed Nov. 4, 2011, Deisseroth, et al.
Tam, B. et al., "Identification of an Outer Segment Targeting Signal in the COOH Terminus of Rhodopsin Using Transgenic Xenopus laevis", The Journal of Cell Biology, 2000, vol. 151, No. 7, pp. 1369-1380.
Brewin; "The Nature and Significance of Memory Disturbance in Posttraumatic Stress Disorder"; Ann. Rev. Clin. Psychol.; vol. 7, pp. 203-227 (2011).
Raper, et al.; "Fatal systemic inflammatory response syndrome in a ornithine transcarbamylase deficient patient following adenoviral gene transfer." Mol. Genet. Metab.; vol. 80, No. 1-2, pp. 148-158 (Sep.-Oct. 2003).
Samuelson; "Post-traumatic stress disorder and declarative memory functioning: a review"; Dialogues in Clinical Neuroscience; vol. 13, No. 3, pp. 346-351 (2011).

Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.
Han, et al., "Multiple-Color Optical Activation, Silencing, and Desynchronization of Neural Activity with Single-Spike Temporal Resolution", PLoS One, 2007, vol. 2, No. 3, pp. 1-12.
Kinoshita, et al., "Optogenetically Induced Supression of Neural Activity in the Macaque Motor Cortex", Poster Sessions Somatomotor System, Others,2010, pp. 141-154.
Rein, et al., "The Optogenetic (r)evolution", Mol. Genet. Genomics, 2012, vol. 287, No. 2, pp. 95-109.
Remy, et al., "Depression in Parkinson's Disease: Loss of Dopamine and Noradrenaline Innervation in the Limbic System", Brain, 2005, vol. 128 (Pt 6), pp. 1314-1322.
Tsai, et al., "Phasic Firing in Dopaminergic Neurons in Sufficient for Behavioral Conditioning", Science, 2009, vol. 324, pp. 1080-1084.
Zhao, et al., "Improved Expression of Halorhodopsin for Light-Induced Silencing of Neuronal Activity", Brain Cell Biology, 2008, vol. 36 (1-4), pp. 141-154.
Lanyi et al. "The primary structure of a Halorhodopsin from *Natronobacterium Pharaonis*" Journal of Biological Chemistry, 1990, vol. 265, No. 3, p. 1253-1260.
Hofherr et al. "Selective Golgi export of Kir2.1 controls the stoichiometry of functional Kir2.x channel heteromers" Journal of Cell Science, 2005, vol. 118, p. 1935-1943.
Loetterle, et al., "Cerebellar Stimulation: Pacing the Brain", American Journal of Nursing, 1975, vol. 75, No. 6, pp. 958-960.
Takahashi, et al., "Induction of Pluripotent Stem Cells from Mouse Embryonic and Adult Fibroblast Cultures by Defined Factors", 2006, Cell, vol. 126, pp. 663-676.
Balint, et al., "The Nitrate Transporting Photochemical Reaction Cycle of the Pharaonis Halorhodopsin", Biophysical Journal, 2004, vol. 86, pp. 1655-1663.
Gradinaru, et al., Molecular and Cellular Approaches for Diversifying and Extending Optogenetics, Cell, 2010, vol. 141, No. 1, pp. 154-165.
RecName: Full=Halorhodopsin; Short=HR; Alt Name: Full=NpHR; XP002704922, retrieved from EBI accession No. Uniprot: P15647. Database accession No. P15647. Apr. 1, 1990.
"N. pharaonis halorhodopsin (hop) gene, complete cds.", XP002704883, retrieved from EBI accession No. EMBL: J05199. Database accession No. J05199. Nov. 22, 1990.
"Subname: Fluu= Bacteriorhodopsin"; XP002704863, retrieved from EBI accession No. UNIPROT: B0R5N9. Database accession No. B0R5N9. Apr. 8, 2008.
Zhang, et al., "The Microbial Opsin Family of Optogenetic Tools", Cell, 2011, vol. 147, No. 7, pp. 1146-1457.
Ali; "Gene and stem cell therapy for retinal disorders"; vision-research.en—The Gateway to European Vision Research; accessed from http://www.vision-research.eu/index.php?id=696, 10 pages (accessed Jul. 24, 2015).
Asano, et al.; "Optically Controlled Contraction of Photosensitive Skeletal Muscle Cells"; Biotechnology & Bioengineering; vol. 109, No. 1, pp. 199-204 (Jan. 2012).
Bruegmann, et al.; "Optogenetic control of heart muscle in vitro and in vivo"; Nature Methods; vol. 7, No. 11, pp. 897-900(Nov. 2010).
Bruegmann, et al.; "Optogenetics in cardiovascular research: a new tool for light-induced depolarization of cardiomyocytes and vascular smooth muscle cells in vitro and in vivo"; European Heart Journal; vol. 32, No. Suppl . 1, p. 997 (Aug. 2011).
Genbank Accession No. AAG01180.1; Idnurm, et al.; pp. 1 (Mar. 21, 2001).
Genbank Accession No. ABT17417.1; Sharma, et al.; pp. 1 (Aug. 15, 2007).
Genbank Accession No. BAA09452.1; Mukohata et al.; pp. 1 (Feb. 10, 1999).
Kessler, et al.; "Gene delivery to skeletal muscle results in sustained expression and systemic delivery of a therapeutic protein"; Proc. Natl. Acad. Sci. USA; vol. 93, pp. 14082-14087 (Nov. 1996).
Mueller, et al.; "Clinical Gene Therapy Using Recombinant Adeno-Associated Virus Vectors"; Gene Therapy; vol. 15, pp. 858-863 (2008).

(56) References Cited

OTHER PUBLICATIONS

Wang, et al.; "Laser-evoked synaptic transmission in cultured hippocampal neurons expressing channelrhodopsin-2 delivered by adeno-associated virus"; Journal of Neuroscience Methods; vol. 183, pp. 165-175 (2009).
Gradinaru et al., "Targeting and readout strategies for fast optical neural control in vitro and in vivo", J Neuroscience, 2007, 27(52):14231-14238.
Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.
Han, et al., "Millisecond-Timescale Optical Control of Neural Dynamics in the Nonhuman Primate Brain"; Neuron; vol. 62, pp. 191-198 (Apr. 30, 2009).
Han, et a.; "Virogenetic and optogenetic mechanisms to define potential therapeutic targets in psychiatric disorders"; Neuropharmacology; vol. 62, pp. 89-100 (2012).
Zhang, et al.; "Optogenetic interrogation of neural circuits: Technology for probing mammalian brain structures"; Nature Protocols; vol. 5, No. 3, pp. 439-456 (Mar. 1, 2010).
Delaney et al., "Evidence for a long-lived 13-cis-containing intermediate in the photocycle of the leu 93→ala bacteriorhodopsin mutant", J. Physical Chemistry B, 1997, vol. 101, No. 29, pp. 5619-5621.
Fenno et al., "The development and application of optogenetics", Annual Review of Neuroscience, 2011, vol. 34, No. 1, pp. 389-412.
Gunaydin et al., "Ultrafast optogenetic control", Nature Neuroscience, 2010, vol. 13, No. 3, pp. 387-392.
Hira et al., "Transcranial optogenetic stimulation for functional mapping of the motor cortex", J Neurosci Methods, 2009, vol. 179, pp. 258-263.
Lalumiere, R., "A new technique for controlling the brain: optogenetics and its potential for use in research and the clinic", Brain Stimulation, 2011, vol. 4, pp. 1-6.
Lin, "A user's guide to channelrhodopsin variants: features, limitations and future developments", Exp Physiol, 2010, vol. 96, No. 1, pp. 19-25.
Mancuso et al., "Optogenetic probing of functional brain circuitry", Experimental Physiology, 2010, vol. 96.1, pp. 26-33.
Peralvarez-Marin et al., "Inter-helical hydrogen bonds are essential elements for intra-protein signal transduction: The role of Asp115 in bacteriorhodopsin transport function", J. Mol. Biol., 2007, vol. 368, pp. 666-676.
Pinkham et al., "Neural bases for impaired social cognition in schizophrenia and autism spectrum disorders", Schizophrenia Research, 2008, vol. 99, pp. 164-175.
Sohal et al., "Parvalbumin neurons and gamma rhythms enhance cortical circuit performance", Nature, 2009, vol. 459, No. 7247, pp. 698-702.
Yizhar et al., "Optogenetics in neural systems", Neuron Primer, 2011, vol. 71, No. 1, pp. 9-34.
Li et al., "Surface Expression of Kv1 Channels is Governed by a C-Terminal Motif", J. Bioi. Chem. (2000), 275(16):11597-11602.
Lonnerberg et al. "Regulatory Region in Choline Acetyltransferase Gene Directs Developmental and Tissue-Specific Expression in Transgenic mice", Proc. Natl. Acad. Sci. USA (1995), 92(9):4046-4050.
Varo et al.," Light-Driven Chloride Ion Transport by Halorhodopsin from Natronobacterium pharaonis. 2. Chloride Release and Uptake, Protein Conformation Change, and Thermodynamics", Biochemistry (1995), 34(44):14500-14507.
Deisseroth, et al., "Controlling the Brain with Light", Scientific American, 2010, vol. 303, pp. 48-55.
Douglass, et al., "Escape Behavior Elicited by Single, Channelrhodopsin-2-evoked Spikes in Zebrafish Somatosensory Neurons", Curr Biol., 2008, vol. 18, No. 15, pp. 1133-1137.
Sineshchekov et al., "Two Rhodopsins Mediate Phototaxis to Low and High Intensity Light in Chlamydomas Reinhardtii", PNAS, 2002, vol. 99, No. 13, pp. 8689-8694.
Tønnese, et al., "Optogenetic Control of Epileptiform Activity", PNAS, 2009, vol. 106, No. 29, pp. 12162-12167.
Ibbini, et al.; "A Field Conjugation Method for Direct Synthesis of Hyperthermia Phased-Array Heating Patterns"; IEEE Transactions on Ultrasonics, Ferroelectrics, and Frequency Control; vol. 36, No. 1, pp. 3-9 (Jan. 1989).
Berndt et al., "Structure-Guided Transformation of Channelrhodopsin into a Light-Activated Chloride Channel", Science (Apr. 2014), 344(6182):420-424.
Chow et al., "Optogenetics and Translational Medicine", Science Translational Medicine (Mar. 2013), 5(177):177ps5.
Eijkelkamp, et al. "Neurological perspectives on voltage-gated sodium channels", Brain (Sep. 2012), 135(Pt 9):2585-2612.
Garrido et al., "A targeting motif involved in sodium channel clustering at the axonal initial segment", Science (Jun. 2003), 300(5628):2091-4.
Han; et al., "Two-color, bi-directional optical voltage control of genetically-targeted neurons", CoSyne (2007), Abstract Presentation, Poster III-67, p. 269, Presented Feb. 24, 2007.
Hustler; et al., "Acetylcholinesterase staining in human auditory and language cortices: regional variation of structural features", Cereb Cortex (Mar.-Apr. 1996), 6(2):260-70.
Iyer et al., "Virally mediated optogenetic excitation and inhibition of pain in freely moving nontransgenic mice", Nat Biotechnol., (Mar. 2014), 32(3):274-8.
Ji et al., "Light-evoked Somatosensory Perception of Transgenic Rats that Express Channelrhodopsin-2 in Dorsal Root Ganglion Cells", PLoS One (2012), 7(3):e32699.
Jennings et al., "Distinct extended amygdala circuits for divergent motivational states," Nature (Apr. 2013), 496(7444):224-8.
Kim et al., "PDZ domain proteins of synapses", Nature Reviews Neuroscience, (Oct. 2004), 5(10):771-81.
Kim et al., "Diverging neural pathways assemble a behavioural state from separable features in anxiety" Nature (Apr. 2013), 496(7444):219-23.
Kokel et al., "Photochemical activation of TRPA1 channels in neurons and animals", Nat Chem Biol (Apr. 2013), 9(4):257-63.
Lammel et al., "Input-specific control of reward and aversion in the ventral tegmental area", Nature (Nov. 2012), 491(7423): 212-7.
Liske et al., "Optical inhibition of motor nerve and muscle activity in vivo", Muscle Nerve (Jun. 2013), 47(6):916-21.
Llewellyn et al., "Orderly recruitment of motor units under optical control in vivo", Nature Medicine, (Oct. 2010), 16(10):1161-5.
Mattis et al., "Principles for applying optogenetic tools derived from direct comparative analysis of microbial opsins", Methods (Dec. 2011), 9(2):159-72.
Mourot et al., "Rapid Optical Control of Nociception with an Ion Channel Photoswitch", Nat Methods (Feb. 2012), 9(4):396-402.
Nieh et al., "Optogenetic dissection of neural circuits underlying emotional valence and motivated behaviors", Brain Research, (May 2012), 1511:73-92.
Slamovits et al., "A bacterial proteorhodopsin proton pump in marie eukaryotes", Nature Communications (Feb. 2011), 2:183.
Towne et al., "Efficient transduction of non-human primate motor neurons after intramuscular delivery of recombinant AAV serotype 6", Gene Ther. (Jan. 2010), 17(1):141-6.
Towne et al., "Optogenetic control of targeted peripheral axons in freely moving animals", PLoS One (Aug. 2013), 8(8):e72691.
Towne et al., "Recombinant adeno-associated virus serotype 6 (rAAV2/6)-mediated gene transfer to nociceptive through different routes of delivery", Mol Pain (Sep. 2009), 5:52.
Wang et al., "Mrgprd-Expressing Polymodal Nociceptive Neurons Innervate Most Known Classes of Substantia Gelatinosa Neurons", J Neurosci (Oct. 2009), 29(42):13202-13209.
Williams et al., "From optogenetic technologies to neuromodulation therapies", Sci Transl Med. (Mar. 2013), 5(177):177ps6.
Berlanga, et a.; "Cholinergic Interneurons of the Nucleus Accumbens and Dorsal Striatum are Activated by the Self-Administration of Cocaine"; Neuroscience; vol. 120, pp. 1149-1156 (2003).
Day, et al.; "The Nucleus Accumbens and Pavlovian Reward Learning"; Neuroscientist; vol. 13, No. 2, pp. 148-159 (Apr. 2007).
Knopfel, et al.; "A comprehensive concept of optogenetics"; Progress in Brain Research; vol. 196, pp. 1-28 (2012).

(56) References Cited

OTHER PUBLICATIONS

Packer, et al.; "Targeting Neurons and Photons for Optogenetics"; Nature Neuroscience; vol. 16, No. 7, pp. 805-815 (Jul. 2013).
Babin et al., "Zebrafish Models of Human Motor Neuron Diseases: Advantages and Limitations", Progress in Neurobiology (2014), 118:36-58.
Santana et al., "Can Zebrafish Be Used as Animal Model to Study Alzheimer's Disease?" Am. J. Neurodegener. Dis. (2012), 1(1):32-48.
Sheikh et al., "Neurodegenerative Diseases: Multifactorial Conformational Diseases and Their Therapeutic Interventions", Journal of Neurodegenerative Diseases (2013), Article ID 563481:1-8.
Suzuki et al., "Stable Transgene Expression from HSV Amplicon Vectors in the Brain: Potential Involvement of Immunoregulatory Signals", Molecular Therapy (2008), 16(10):1727-1736.
Thomas et al., "Progress and Problems with the Use of Viral Vectors for Gene", Nat. Rev. Genet. (2003), 4(5):346-358.
Cardin, et al.; "Targeted optogenetic stimulation and recording of neurons in vivo using cell-type-specific expression of Channelrhodopsin-2"; Nat Protoc. Feb. 2010; 5(2): 247-254.
Ginn, et al.; "Gene therapy clinical trials worldwide to 2012—an update"; J Gene Med 2013; 15: 65-77.
Jones, et al.; "Animal Models of Schizophrenia"; British Journal of Pharmacology; vol. 164, pp. 1162-1194 (2011).
McCarty, et al.; "Self-complementary recombinant adeno-associated virus (scAAV) vectors promote efficient transduction independently of DNA synthesis"; Gene Therapy (2001) 8, 1248-1254.
Oka, et al.; "Liver-directed Gene Therapy for Dyslipidemia and Diabetes"; Curr Atheroscler Rep. May 2004; 6(3): 203-209.
Petreanu, et al.; "The subcellular organization of neocortical excitatory connections"; Nature. Feb. 26, 2009; 457(7233): 1142-1145.
Yajima, et al., "Effects of bromazepam on responses of mucosal blood flow of the gastrointestinal tract and the gastric motility to stimulation of the amygdala and hypothalamus in conscious cats"; Folia Pharmacol. Japon; vol. 83, No. 3, pp. 237-248 (Mar. 1984). [English abstract translation].
Yamada, Shigeto; "Neurobiological Aspects of Anxiety Disorders"; The Japanese Journal of Psychiatry; vol. 8, No. 6, pp. 525-535 (Nov. 25, 2003). [English translation of introduction and summary].
Chow, et al.; "High-performance genetically targetable optical neural silencing by light-driven proton pumps"; Nature; vol. 463, pp. 98-102 (Jan. 7, 2010).
Gong, et al.; "Enhanced Archaerhodopsin Fluorescent Protein Voltage Indicators"; PLOS One; vol. 8, Issue 6, 10 pages. (Jun. 2013).
Han, et al.; "A high-light sensitivity optical neural silencer: development and application to optogenetic control of non-human primate cortex"; Frontiers in Systems Neuroscience; vol. 5, Article 18, pp. 1-8 (Apr. 2011).
Airan, et al.; "Integration of light-controlled neuronal firing and fast circuit imaging"; Current Opinion in Neurobiology; vol. 17, pp. 587-592 (2007).
Cannon, et al.; "Endophenotypes in the Genetic Analyses of Mental Disorders"; Annu. Rev. Clin. Psychol.; vol. 2, pp. 267-290 (2006).
Chamanzar, et al.; "Deep Tissue Targeted Near-infrared Optogenetic Stimulation using Fully Implantable Upconverting Light Bulbs"; 2015 37th Annual International Conference of the IEEE Engineering in Medicine and Biology Society (EMBC), IEEE; doi: 10.1109/EMBC.2015.7318488, pp. 821-824 (Aug. 25, 2015).
Chinta, et al.; "Dopaminergic neurons"; The International Journal of Biochemistry & Cell Biology; vol. 37, pp. 942-946 (2005).
Deonarain; "Ligand-targeted receptor-mediated vectors for gene delivery"; Exp. Opin. Ther. Patents; vol. 8, No. 1, pp. 53-69 (1998).
Edelstein, et al.; "Gene therapy clinical trials worldwide 1989-2004—an overview"; The Journal of Gene Medicine; vol. 6, pp. 597-602 (2004).
Grady, et al.; "Age-Related Reductions in Human Recognition Memory Due to Impaired Encoding"; Science; vol. 269, No. 5221, pp. 218-221 (Jul. 14, 1995).
Hososhima, et al.; "Near-infrared (NIR) up-conversion optogenetics"; Optical Techniques in Neurosurgery, Neurophotonics, and Optogenetics II; vol. 9305, doi: 10.1117/12.2078875, 4 pages (2015).
Johnson-Saliba, et al.; "Gene Therapy: Optimising DNA Delivery to the Nucleus"; Current Drug Targets; vol. 2, pp. 371-399 (2001).
Palu, et al.; "In pursuit of new developments for gene therapy of human diseases"; Journal of Biotechnology; vol. 68, pp. 1-13 (1999).
Petersen, et al.; "Functionally Independent Columns of Rat Somatosensory Barrel Cortex Revealed with Voltage-Sensitive Dye Imaging"; J. of Neuroscience; vol. 21, No. 21, pp. 8435-8446 (Nov. 1, 2011).
Pfeifer, et al.; "Gene Therapy: Promises and Problems"; Annu. Rev. Genomics Hum. Genet.; vol. 2, pp. 177-211 (2001).
Powell, et al.; "Schizophrenia-Relevant Behavioral Testing in Rodent Models: A Uniquely Human Disorder?"; Biol. Psychiatry; vol. 59, pp. 1198-1207 (2006).
Shoji, et al.; "Current Status of Delivery Systems to Improve Target Efficacy of Oligonucleotides"; Current Pharmaceutical Design; vol. 10, pp. 785-796 (2004).
Verma, et al.; "Gene therapy—promises, problems and prospects"; Nature; vol. 389, pp. 239-242 (Sep. 1997).
Wang, et al.; "Simultaneous phase and size control of upconversion nanocrystals through lanthanide doping"; Nature; vol. 463, No. 7284, pp. 1061-1065 (Feb. 25, 2010).
Davidson, et al.; "Viral Vectors for Gene Delivery to the Nervous System"; Nature Reviews Neuroscience; vol. 4, pp. 353-364 (May 2003).
Fanselow, et al.; "Why We Think Plasticity Underlying Pavlovian Fear Conditioning Occurs in the Basolateral Amygdala"; Neuron; vol. 23, pp. 229-232 (Jun. 1999).
Rogers, et al.; "Effects of ventral and dorsal CA1 subregional lesions on trace fear conditioning"; Neurobiology of Learning and Memory; vol. 86, pp. 72-81 (2006).
Clark, et al.; "A future for transgenic livestock"; Nature Reviews Genetics; vol. 4, No. 10, pp. 825-833 (Oct. 2003).
Do Carmo, et al.; "Modeling Alzheimer's disease in transgenic rats"; Molecular Neurodegeneration; vol. 8, No. 37, 11 pages (2013).
Heymann, et al.; "Expression of Bacteriorhodopsin in Sf9 and COS-1 Cells"; Journal of Bioenergetics and Biomembranes; vol. 29, No. 1, pp. 55-59 (1997).
Ramalho, et al.; "Mouse genetic corneal disease resulting from transgenic insertional mutagenesis"; Br. J. Ophthalmol.; vol. 88, No. 3, pp. 428-432 (Mar. 2004).
Ristevski; "Making Better Transgenic Models: Conditional, Temporal, and Spatial Approaches"; Molecular Biotechnology; vol. 29, No. 2, pp. 153-163 (Feb. 2005).
Sigmund; "Viewpoint: Are Studies in Genetically Altered Mice Out of Control?"; Arterioscler Thromb Vasc. Biol.; vol. 20, No, 6, pp. 1425-1429 (Jun. 2000).
Sineshchekov et al.; "Intramolecular Proton Transfer in Channelrhodopsins"; Biophysical Journal; vol. 104, No. 4, pp. 807-807 (Feb. 2013).
Johnson, et al.; "Differential Biodistribution of Adenoviral Vector In Vivo as Monitored by Bioluminescence Imaging and Quantitative Polymerase Chain Reaction"; Human Gene Therapy; vol. 17, pp. 1262-1269 (Dec. 2006).
Schester, et al.; "Biodistribution of adeno-associated virus serotype 9 (AAV9) vector after intrathecal and intravenous delivery in mouse"; Frontiers in Neuroanatomy; vol. 8, Article 42, pp. 1-41 (Jun. 10, 2014).
Definition of Implant; Merriam-Webster Dictionary; retrieved Nov. 7, 2016 (http://www.merriam-webster.com/dictionary/implant).
Ferenczi, et al.; "Optogenetic approaches addressing extracellular modulation of neural excitability"; Scientific Reports; vol. 6, 20 pages (Apr. 5, 2016).
Li, et al.; "A Method for Activation of Endogenous Acid-sensing Ion Channel 1a (ASIC1a) in the Nervous System with High Spatial and Temporal Precision"; The Journal of Biological Chemistry; vol. 289, No. 22, pp. 15441-15448 (May 30, 2014).

(56) References Cited

OTHER PUBLICATIONS

Shimizu, et al.; "NMDA Receptor-Dependent Synaptic Reinforcement as a Crucial Process for Memory Consolidation"; Science; vol. 290, pp. 1170-1174 (Nov. 10, 2000).
Zeng, et al.; "Activation of acid-sensing ion channels by localized proton transient reveals their role in proton signaling"; Scientific Reports; vol. 5, 14 pages (Sep. 15, 2015).
Zeng, et al.; "Proton production, regulation and pathophysiological roles in the mammalian brain"; Neuroscience Bulletin; vol. 28, No. 1, pp. 1-13 (Feb. 1, 2012).
Definition of integral. Merriam-Webster Dictionary, retrieved on Mar. 20 2017; Retrieved from the internet: <http://www.merriam-webster.com/dictionary/integral>.
Abbott, et al.; "Photostimulation of Retrotrapezoid Nucleus Phox2b-Expressing Neurons In Vivo Produces Long-Lasting Activation of Breathing in Rats"; The Journal of Neuroscience; vol. 29, No. 18, pp. 5806-5819 (May 6, 2009).
Alilain, et al.; "Light-Induced Rescue of Breathing after Spinal Cord Injury"; The Journal of Neuroscience; vol. 28, No. 46, pp. 11862-11870 (Nov. 12, 2008).
Cardin, et al.; "Targeted optogenetic stimulation and recording of neurons in vivo using cell-type-specific expression of Channelrhodopsin-2"; Nature Protocols; vol. 5, No. 2, pp. 247-254 (2010).
Caro, et al.; "Engineering of an Artificial Light-Modulated Potassium Channel"; PLoS One; vol. 7, Issue 8, e43766 (Aug. 2012).
Coleman, et al.; "Assessing Anxiety in Nonhuman Primates"; Ilar Journal; vol. 55, No. 2, pp. 333-346 (2014).
Hagglund, et al.; "Activation of groups of excitatory neurons in the mammalian spinal cord or hindbrain evokes locomotion"; Nature Neuroscience; vol. 13, No. 2, 8 pages (Feb. 2010).
Kleinlogel, et al.; "A gene-fusion strategy for stoichiometric and co-localized expression of light-gated membrane proteins"; Nature Methods; vol. 8, No. 12, pp. 1083-1091 (Dec. 2011).
Kravitz, et al.; "Regulation of parkinsonian motor behaviours by optogenetic control of basal ganglia circuitry"; Nature; vol. 466, No. 622, 8 pages (Jul. 29, 2010).
Luo, et al.; "Synthetic DNA delivery systems"; Nature Biotechnology; vol. 18, pp. 33-37 (Jan. 2000).
Maestripieri, et al.; "A modest proposal: displacement activities as an indicator of emotions in primates"; Anim. Behav.; vol. 44, pp. 967-979 (1992).
Nelson, et al.; "Non-Human Primates: Model Animals for Developmental Psychopathology"; Neuropsychopharmacology; vol. 34, No. 1, pp. 90-105 (Jan. 2009).
Tomita, et al.; "Visual Properties of Transgenic Rats Harboring the Channelrhodopsin-2 Gene Regulated by the Thy-1.2 Promoter"; PLoS One; vol. 4, No. 11, 13 pages (Nov. 2009).
Uniprot Accession No. P02945, integrated into the database on Jul. 21, 1986.
Azizgolshani, et al.; "Reconstituted plant viral capsids can release genes to mammalian cells"; Virology; vol. 441, No. 1, pp. 12-17 (2013).
Racaniello; "How many viruses on Earth?"; Virology Blog; 6 pages; http://www.virology.ws/2013/09/06/how-many-viruses-on-earth/ (Sep. 6, 2013).
Gritton, et al.; "Optogenetically-evoked cortical cholinergic transients in mice expressing channelrhodopsin-2 (ChR2) in cholinergic neurons"; Society for Neuroscience Abstract Viewer and Itinery Planner & 40th Annual Meeting of the Society-for-Neuroscience; vol. 40, 2 pages (2010).
Sofuoglu, et al.; "Cholinergic Functioning in Stimulant Addiction: Implications for Medications Development"; CNS Drugs; vol. 23, No. 11, pp. 939-952 (Nov. 1, 2009).
Witten, et al.; "Cholinergic interneurons of the nucleus accumbens control local circuit activity and reward behavior"; Society for Neuroscience Abstract Viewer and Itinerary Planner & 40th Annual Meeting of the Society-for-Neuroscience; vol. 40, 2 pages (2010).
Bibel, et al.; "Differentiation of mouse embryonic stem cells into a defined neuronal lineage"; Nature Neuroscience; vol. 7, No. 9, pp. 1033-1009 (Sep. 2004).
Daniel, et al.; "Stress Modulation of Opposing Circuits in the Bed Nucleus of the Stria Terminalis"; Neuropsychopharmacology Reviews; vol. 41, pp. 103-125 (2016).
Hammack, et al.; "The response of neurons in the bed nucleus of the stria terminalis to serotonin Implications for anxiety"; Progress in Neuro-Psychopharmacology & Biological Psychiatry; vol. 33, pp. 1309-1320 (2009).
Knopfel, et al.; "Remote control of cells"; Nature Nanotechnology; vol. 5, pp. 560-561 (Aug. 2010).
Steimer; "The biology of fear- and anxiety-related behaviors"; Dialogues in Clinical Neuroscience; vol. 4, No. 3, pp. 231-249 (Sep. 2002).
Stuber; "Dissecting the neural circuitry of addiction and psychiatric disease with optogenetics"; Neuropsychopharmacology; vol. 35, No. 1, pp. 341-342 (2010).
Lin, et al.; "Study of the Circuitry of Nucleus Accumbens and its Effect on Addiction by Optogenetic Methods: 964"; Neurosurgery; vol. 67, No. 2, pp. 557 (Aug. 2010).
Tsuchida; "Nervous Control of Micturition"; The Japanese Journal of Urology; vol. 80, No. 9, pp. 1257-1277 (1989).
Kugler, et al.; "Neuron-Specific Expression of Therapeutic Proteins: Evaluation of Different Cellular Promoters in Recombinant Adenoviral Vectors"; Molecular and Cellular Neuroscience; vol. 17, pp. 78-96 (2001).
Masaki, et al.; "β-Adrenergic Receptor Regulation of the Cardiac L-Type Ca2+ Channel Coexpressed in a Fibroblast Cell Line"; Receptor; vol. 5, pp. 219-231 (1996).
Smith, et al.; "Proton binding sites involved in the activation of acid-sensing ion channel ASIC2a"; Neuroscience Letters; vol. 426, pp. 12-17 (2007).
Friedman, et al.; "VTA Dopamine Neuron Bursting is Altered in an Animal Model of Depression and Corrected by Desipramine"; J. Mol. Neurosci.; vol. 34, pp. 201-209 (2008).
Hackmann, et al.; "Static and time-resolved step-scan Fourier transform infrared investigations of the photoreaction of halorhodopsin from Natronobacterium pharaonis: consequences for models of the anion translocation mechanism"; Biophysical Journal; vol. 81, pp. 394-406 (Jul. 2001).
Weiss, et al.; "Galanin: A Significant Role in Depression?"; Annals New York Academy of Sciences; vol. 863, No. 1, pp. 364-382 (1998).
Winter, et al.; "Lesions of dopaminergic neurons in the substantia nigra pars compacta and in the ventral tegmental area enhance depressive-like behavior in rats"; Behavioural Brain Research; vol. 184, pp. 133-141 (2007).
Boyden, et al.; "A history of optogenetics: the development of tools for controlling brain circuits with light"; F1000 Biology Reports; vol. 3, No. 11, 12 pages (May 3, 2011).
Knox, et al.; "Heterologous Expression of *Limulus* Rhodopsin"; The Journal of Biological Chemistry; vol. 278, No. 42, pp. 40493-40502 (Oct. 17, 2003).
Lin, et al.; "Characterization of Engineered Channelrhodopsin Variants with Improved Properties and Kinetics"; Biophysical Journal; vol. 96, No. 5, pp. 1803-1814 (Mar. 2009).
Gerits, et al.; "Optogenetically Induced Behavioral and Functional Network Changes in Primates"; Current Biology; vol. 22, pp. 1722-1726 (Sep. 25, 2012).
Han, et al.; "Optogenetics in the nonhuman primate"; Prog. Brain Res.; vol. 196, pp. 215-233 (2012).
Nargeot et al.; Molecular basis of the diversity of calcium channels in cardiovascular tissues European Heart Journal, 1997, Supplemental A, A15-A26.
Erbguth et al. "Bimodal Activation of Different Neuron Classes with Spectrally Red-Shifted Channelrhodopsin Chimera C1V1 in Caenorhabditis elegans," PLOS One, 2012, vol. 7 No. 10, pp. e46827/1-e46827/9.
Li et al.; "Role of a Helix B Lysine Residue in the Photoactive Site in Channelrhodopsins," Biophysical Journal, 2014, vol. 106, pp. 1607-1617.
Prigge et al.: "Functional Studies of Volvox Channelrhodopsin Chimeras," Biophysical Journal, 2010, vol. 98, No. 3, Suppl. 1, 3694 Poster, 1 page.

(56) References Cited

OTHER PUBLICATIONS

Prigge et al.; Color-tuned Channelrhodopsins for Multiwavelength Optogenetics, J. Biol. Chem. 2012, vol. 287, No. 38, pp. 31804-31812.
Tsunoda & Hegemann "Glu 87 of Channelrhodopsin-1 Causes pH-dependent Color Tuning and Fast Photocurrent Inactivation," Photochemistry and Photobiology, 2009, vol. 85, No. 2, pp. 564-569.
Duvarci, et al., "The bed Nucleus of the Stria Terminalis Mediates inter-individual variations in anxiety and fear", J. Neurosci., 29(33) 10357-10361 (2009).
Matsuda "Bed nucleus of stria terminalis (BNST)" Benshi Seishin Igaku (Molecular Psychiatric Medicine), 2009, vol. 9 No. 3, p. 46-49.
Neuropsychopharmacology, 2011, vol. 36 No. Suppl.1, p. S110 (Abstract No. 67).
Neuropsychopharmacology, 2012, vol. 38 No. Suppl.1, p. S48 (Abstract No. 37.2).
Walker et al. "Selective Participation of the Bed Nucleus of the Stria Terminalis and CRF in Sustained Anxiety-like versus Phasic Fear-Like Responses," Prog Neuropsychopharmacol Bio Psychiatry, 13: 33(8) 1291-1308 (2009).
Ahmad, et al. "Heterplogous expression of bovine rhodopsin in *Drosophila* photoreceptor cells" Invest Ophthalmol Vis Sci. 2006, 3722-3728.
Clare "Targeting Ion Channels for Drug Discovery" Discov Med. 2010 vol. 9 No. 46 pp. 1-6.
Clare "Functional Expression of Ion Channels in Mammalian Systems" Protein Science Encyclopedia A.R. Fersht (Ed.) 2008 pp. 79-109.
Reeves et al., "Structure and function in rhodosin: A tetracycline-inducible system in stable mammalian cell lines for high-level expression of opsin mutants" PNAS, 2002 vol. 99 No. 21 pp. 13413-13418.
Belzung et al., "Optogenetics to study the circuits of fear- and depresssion-like behaviors: A critical analysis," Pharmacology, Biochemistry and Behavior, 2014, 122: 144-157.
Bernstein & Boyden "Optogenetic tools for analyzing the neural circuits of behavior," Trends Cogn Sci., 2011 15(12): 592-600.
U.S. Appl. No. 11/459,636, filed Jul. 24, 2006, published as US 2007-0261127.
U.S. Appl. No. 11/459,638, filed Jul. 24, 2006, published as US 2007-0054319.
U.S. Appl. No. 11/651,422, filed Jan. 9, 2007, published as US 2008-0085265.
U.S. Appl. No. 12/031,651, filed Feb. 14, 2008, issued as U.S. Pat. No. 8,401,609 on Mar. 19, 2013.
U.S. Appl. No. 12/185,624, filed Aug. 4, 2008, published as US 2009-0088680.
U.S. Appl. No. 12/187,927, filed Aug. 7, 2008, published as US 2009-0099038.
U.S. Appl. No. 12/263,026, filed Oct. 31, 2008, published as US 2009-0112133.
U.S. Appl. No. 12/263,044, filed Oct. 31, 2008, published as US 2009-0118800.
U.S. Appl. No. 12/522,520, filed Jan. 8, 2010, issued as U.S. Pat. No. 8,398,692 on Mar. 19, 2013.
U.S. Appl. No. 12/522,528, filed Apr. 6, 2010, published as US 2010-0190229.
U.S. Appl. No. 12/715,259, filed Mar. 1, 2010, published as US 2010-0234273.
U.S. Appl. No. 12/988,567, filed Dec. 7, 2010, published as US 2011-0105998.
U.S. Appl. No. 12/993,605, filed Jan. 20, 2011, published as US 2011-0112179.
U.S. Appl. No. 12/996,753, filed Mar. 10, 2011, published as US 2011-0166632.
U.S. Appl. No. 12/997,140, filed Feb. 7, 2011, published as US 2011-0159562.
U.S. Appl. No. 12/997,158, filed Feb. 7, 2011, published as US 2011-0172653.
U.S. Appl. No. 13/128,979, filed Jul. 28, 2011, published as US 2011-0311489.
U.S. Appl. No. 13/208,419, filed Aug. 12, 2011, published as US 2011-0301529.
U.S. Appl. No. 13/299,727, filed Nov. 18, 2011, published as US 2012-0165904.
U.S. Appl. No. 13/555,981, filed Jul. 23, 2013.
U.S. Appl. No. 13/577,565, filed Sep. 14, 2012, published as US 2013-0019325.
U.S. Appl. No. 13/622,809, filed Sep. 18, 2012.
U.S. Appl. No. 13/623,612, filed Sep. 20, 2013.
U.S. Appl. No. 13/718,243, filed Dec. 18, 2012.
U.S. Appl. No. 13/763,119, filed Feb. 8, 2013.
U.S. Appl. No. 13/763,132, filed Feb. 8, 2013.
U.S. Appl. No. 13/772,732, filed Feb. 21, 2013.
U.S. Appl. No. 13/847,653, filed Mar. 20, 2013.
U.S. Appl. No. 13/847,785, filed Mar. 20, 2013.
U.S. Appl. No. 13/849,913, filed Mar. 25, 2013.
U.S. Appl. No. 13/850,426, filed Mar. 26, 2013.
U.S. Appl. No. 13/850,428, filed Mar. 26, 2013.
U.S. Appl. No. 13/850,436, filed Mar. 26, 2013.
U.S. Appl. No. 13/850,709, filed Mar. 26, 2013.
U.S. Appl. No. 13/854,750, filed Apr. 1, 2013.
U.S. Appl. No. 13/854,754, filed Apr. 1, 2013.
U.S. Appl. No. 13/855,413, filed Apr. 2, 2013.
U.S. Appl. No. 13/882,566, filed Nov. 4, 2011.
U.S. Appl. No. 13/882,670, filed Nov. 4, 2011.
U.S. Appl. No. 13/822,703, filed Nov. 4, 2011.
U.S. Appl. No. 13/875,966, filed May 2, 2013.
U.S. Appl. No. 13/882,705, filed Nov. 4, 2011.
U.S. Appl. No. 13/882,719, filed Nov. 4, 2011.

\* cited by examiner

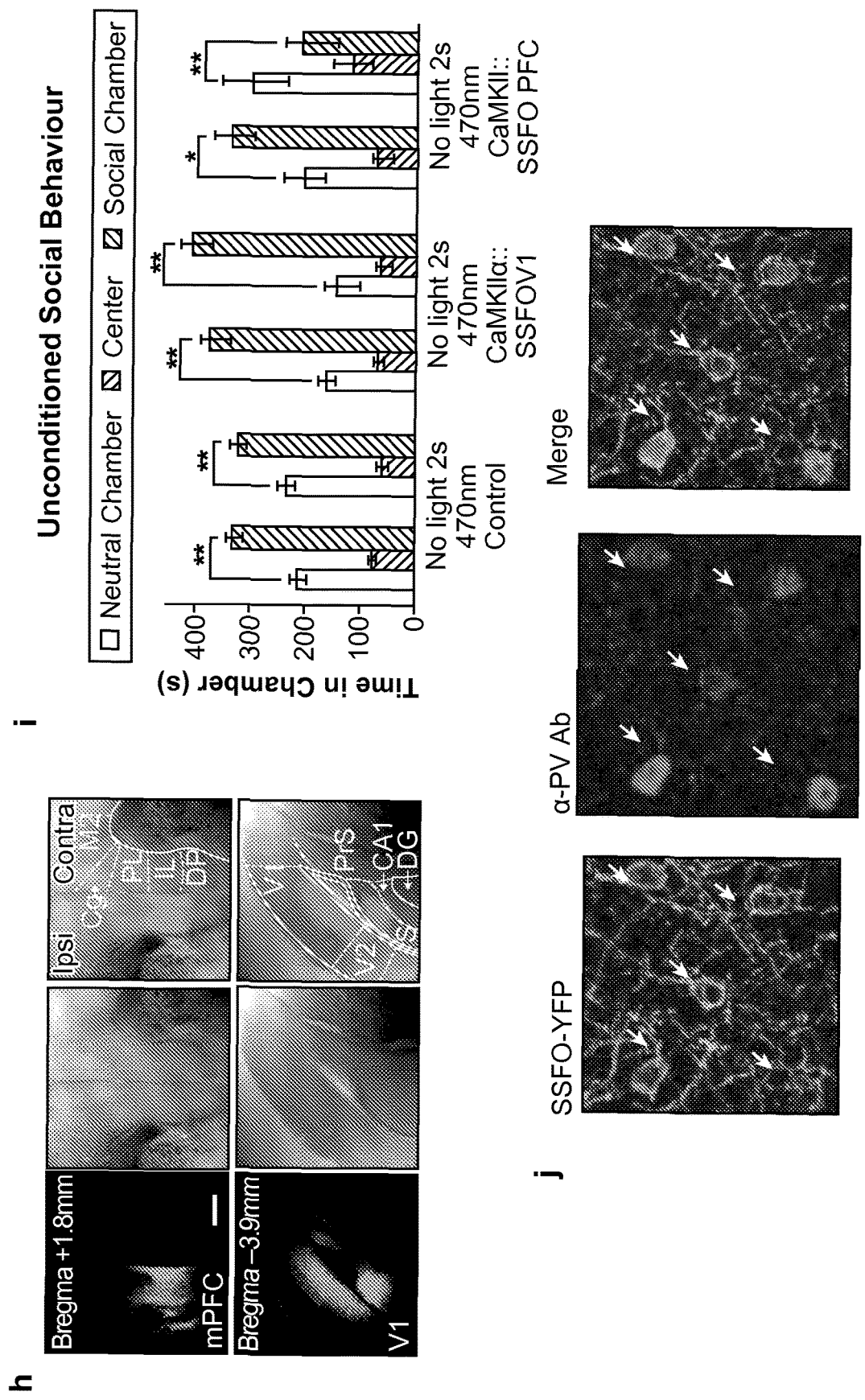
FIG. 3 (Cont. 1)

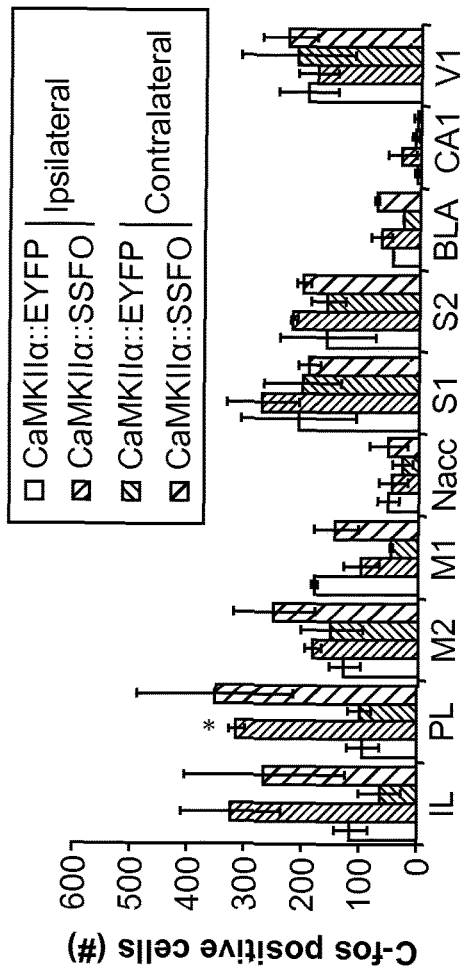
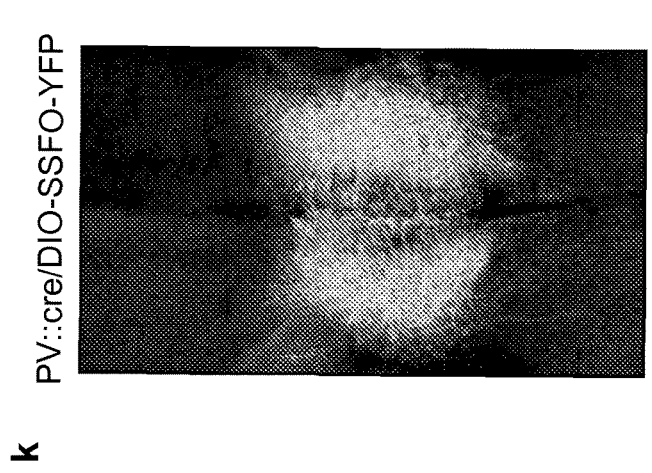
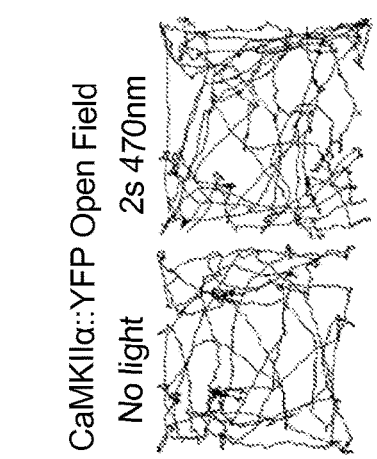
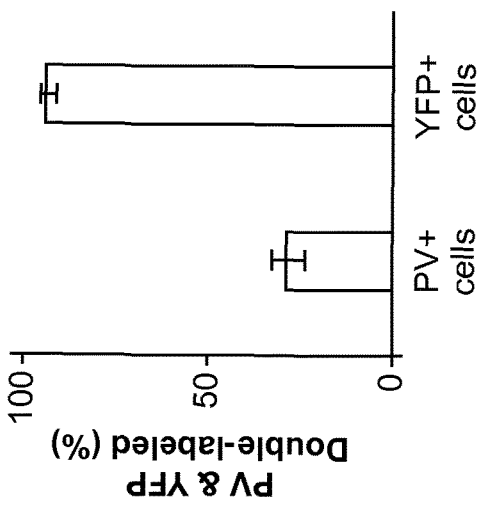
FIG. 3 (Cont. 2)

STABILIZED STEP FUNCTION OPSIN PROTEINS AND METHODS OF USING THE SAME

CROSS REFERENCE TO RELATED APPLICATIONS

This application claims priority to U.S. Provisional Patent Application No. 61/410,704 filed on Nov. 5, 2010, U.S. Provisional Patent Application No. 61/410,711 filed on Nov. 5, 2010, and U.S. Provisional Patent Application No. 61/511,905 filed on Jul. 26, 2011, the disclosures of each of which are incorporated by reference herein in their entireties.

TECHNICAL FIELD

This application pertains to compositions comprising non-human animal cells expressing stabilized step function opsin (SSFO) proteins on their plasma membranes and methods of using the same to selectively depolarize neurons residing in microcircuits of the pre-frontal cortex to affect one or more social behaviors, communications, and/or conditioned behaviors in the non-human animal.

BACKGROUND

Optogenetics is the combination of genetic and optical methods used to control specific events in targeted cells of living tissue, even within freely moving mammals and other animals, with the temporal precision (millisecond-timescale) needed to keep pace with functioning intact biological systems. The hallmark of optogenetics is the introduction of fast light-activated channel proteins to the plasma membranes of target neuronal cells that allow temporally precise manipulation of neuronal membrane potential while maintaining cell-type resolution through the use of specific targeting mechanisms. Among the microbial opsins which can be used to investigate the function of neural systems are the channelrhodopsins (ChR2, ChR1, VChR1, and SFOs) used to promote depolarization in response to light. In just a few short years, the field of optogenetics has furthered the fundamental scientific understanding of how specific cell types contribute to the function of biological tissues such as neural circuits in vivo. Moreover, on the clinical side, optogenetics-driven research has led to insights into Parkinson's disease and other neurological and psychiatric disorders.

However, in spite of these advances, the neurophysiological substrates of most psychiatric disorders remain poorly understood, despite rapidly emerging information on genetic factors that are associated with complex behavioral phenotypes such as those observed in autism and schizophrenia (Cichon et al., *The American Journal of Psychiatry* 166(5): 540 (2009); O'Donovan et al., *Human Genetics* 126(1): 3 (2009)). One remarkable emerging principle is that a very broad range of seemingly unrelated genetic abnormalities can give rise to the same class of psychiatric phenotype (such as social behavior dysfunction; Folstein & Rosen-Sheidley, *Nature Reviews* 2(12):943 (2001)). This surprising pattern has pointed to the need to identify simplifying circuit-level insights that could unify diverse genetic factors under a common pathophysiological principle.

One such circuit-level hypothesis is that elevation in the ratio of cortical cellular excitation and inhibition (cellular E/I balance) could give rise to the social and cognitive deficits of autism (Rubenstein, *Current Opinion in Neurology* 23(2):118; Rubenstein & Merzenich, *Genes, Brain, and Behavior* 2(5):255 (2003)). This hypothesis could potentially unify diverse streams of pathophysiological evidence, including the observation that many autism-related genes are linked to gain-of-function phenotypes in ion channels and synaptic proteins (Bourgeron, *Current Opinion in Neurobiology* 19 (2), 231 (2009)) and that ~30% of autistic patients also show clinically apparent seizures (Gillberg & Billstedt, *Acta Psychiatrica Scandinavica*, 102(5):321 (2000)). However, it has not been clear if such an imbalance (to be relevant to disease symptoms) would be operative on the chronic (e.g. during development) or the acute timescale. Furthermore, this hypothesis is by no means universally accepted, in part because it has not yet been susceptible to direct testing. Pharmacological and electrical interventions lack the necessary specificity to selectively favor activity (in a manner fundamentally distinct from receptor modulation) of neocortical excitatory cells over inhibitory cells, whether in the clinical setting or in freely behaving experimental mammals during social and cognitive tasks. It is perhaps related to challenges such as this that the social and cognitive deficits of autism and schizophrenia have proven largely unresponsive to conventional psychopharmacology treatments in the clinic.

Existing optogenetic methods are also inadequate for this purpose; driving coordinated spikes selectively in excitatory or inhibitory cells with a channelrhodopsin is feasible, but not well suited to the sparse coding and asynchronous firing patterns of neocortical pyramidal cells. Moreover, the continuous presence of an optical fiber and other hardware poses challenges for prolonged behavioral tests with fast and spatially complex movements typical of social behavior and cognitive measures (for example in contextual conditioning). Instead, selectively favoring excitation of one population over another with a bistable step-function opsin (SFO) gene product could partially address these challenges, since the targeted population would not be driven with coordinated spikes, but merely sensitized to native inputs that can be sparse and asynchronous. Use of SFOs also has the potential to address the hardware challenge, since the orders-of-magnitude greater light sensitivity characteristic of SFOs could in theory allow non-brain penetrating light delivery, and the persistent action of the bistable SFOs after light-off could allow hardware-free behavioral testing. However, the known SFOs (C128A,S,T and D156A) are not stable enough to produce constant photocurrent after a single light flash over the many minutes required for complex behavioral testing.

What is needed, therefore, is an optogenetic tool which would permit direct testing of the E/I balance hypothesis in the prefrontal cortex both in vitro and in vivo in freely-moving mice. Such a light-activated protein could permit investigation of the effect of bi-directional modulation of prefrontal cellular E/I balance on both conditioned and innate behaviors relevant for cognitive and social dysfunction, as well as probe the resulting effects on circuit physiology and quantitative transmission of information.

BRIEF SUMMARY OF THE INVENTION

Provided herein are animal cells, non-human animals, brain slices comprising cells expressing stabilized step function opsin proteins on their plasma membranes and methods of using the same to selectively depolarize neurons residing in microcircuits of the pre-frontal cortex.

Accordingly, provided herein are non-human animals comprising a first light-activated cation channel protein expressed in neurons of the pre-frontal cortex of the animal, wherein the protein is capable of inducing depolarizing current in the neurons by light and exhibits rapid step-like activation in response to a single pulse of light having a first wavelength and deactivation in response to a pulse of light having a second wavelength, wherein the depolarizing current in the neurons is maintained for at least about ten minutes; and wherein the activation of the protein in the pre-frontal cortex neurons induces changes in social behaviors, communications, and/or conditioned behaviors in the animal.

In some aspects, there is provided a brain slice comprising neurons of the pre-frontal cortex, wherein a light-activated protein is expressed in the neurons of the pre-frontal cortex, wherein the protein is capable of inducing depolarizing current in the neurons by light and exhibits rapid step-like activation in response to a single pulse of light having a first wavelength and deactivation in response to a pulse of light having a second wavelength; wherein the depolarizing current in the neurons is maintained for at least about ten minutes.

In another aspect, there is provided a method for identifying a chemical compound that inhibits the depolarization of excitatory or inhibitory neurons in the prefrontal cortex of a non-human animal, the method comprising: (a) depolarizing excitatory or inhibitory neurons in the prefrontal cortex of a non-human animal comprising a first light-activated protein cation channel protein expressed on the cell membrane of the neurons of the pre-frontal cortex of the animal, wherein the protein is capable of mediating a depolarizing current in the neurons when the neurons are illuminated with light, wherein the protein exhibits rapid step-like activation in response to a single pulse of light having a first wavelength and deactivation in response to a pulse of light having a second wavelength; wherein the depolarizing current in the neurons is maintained for at least about ten minutes; wherein the protein comprises the amino acid sequence of ChR2, ChR1, VChR1, or VChR2 with amino acid substitutions at amino acid residues corresponding to C128 and D156 of the amino acid sequence of ChR2; wherein the activation of the protein in the pre-frontal cortex neurons induces changes in social behaviors, communications, and/or conditioned behaviors in the animal; (b) measuring an excitatory post synaptic potential (EPSP) or an inhibitory post synaptic current (IPSC) in response to selectively depolarizing the excitatory neurons comprising the light-activated protein; (c) contacting the excitatory or inhibitory neurons with a chemical compound; and (d) measuring the excitatory post synaptic potential (EPSP) or the inhibitory post synaptic current (IPSC) to determine if contacting the excitatory neurons with the chemical compound inhibits the depolarization of the neurons.

In another aspect, there is provided a method for identifying a chemical compound that restores a social behavior, communication, and/or conditioned behavior in a non-human animal, the method comprising: (a) depolarizing excitatory neurons in the prefrontal cortex of a non-human animal comprising a light-activated protein cation channel protein expressed on the cell membrane of the neurons, wherein the protein is capable of inducing a depolarizing current in the neurons when the neurons are illuminated with light, wherein the protein exhibits rapid step-like activation in response to a single pulse of light having a first wavelength and deactivation in response to a pulse of light having a second wavelength; wherein the depolarizing current in the neurons is maintained for at least about ten minutes; and wherein the protein comprises the amino acid sequence of ChR2, ChR1, VChR1, or VChR2 with amino acid substitutions at amino acid residues corresponding to C128 and D156 of the amino acid sequence of ChR2, wherein depolarizing the excitatory neuron inhibits one or more social behaviors, communications, and/or conditioned behaviors in the non-human animal; (c) administering a chemical compound to the non-human animal; and (d) determining if the administration of the chemical compound to the non-human animal restores said one or more social behaviors, communications, and/or conditioned behaviors in the non-human animal.

The present disclosure relates to optical control over nervous system disorders (such as disorders associated with social dysfunction), as described herein. While the present disclosure is not necessarily limited in these contexts, various aspects of the disclosure may be appreciated through a discussion of examples using these and other contexts.

Various embodiments of the present disclosure relate to an optogenetic system or method that correlates temporal, spatio and/or cell-type control over a neural circuit with measurable metrics. For instance, various metrics or symptoms might be associated with a neurological disorder (such as a neurological disorder exhibiting various symptoms of social dysfunction). The optogenetic system targets a neural circuit within a subject/patient for selective control thereof. The optogenetic system involves monitoring the subject/patient for the metrics or symptoms associated with the neurological disorder. In this manner, the optogenetic system can provide detailed information about the neural circuit, its function and/or the neurological disorder.

Consistent with the embodiments discussed herein, particular embodiments relate to studying and probing disorders. Other embodiments relate to the identification and/or study of phenotypes and endophenotypes. Still other embodiments relate to the identification of treatment targets.

Aspects of the present disclosure are directed toward the artificial inducement of disorder/disease states on a fast-temporal time scale. These aspects allow for study of disease states in otherwise healthy animals. This can be particularly useful for diseases that are poorly understood and otherwise difficult to accurately model in live animals. For instance, it can be difficult to test and/or study disease states due to the lack of available animals exhibiting the disease state. Moreover, certain embodiments allow for reversible disease states, which can be particularly useful for establishing baseline/control points for testing and/or for testing the effects of a treatment on the same animal when exhibiting the disease state and when not exhibiting the disease state. Various other possibilities exist, some of which are discussed in more detail herein.

Aspects of the present disclosure are directed to using an artificially induced disorder/disease state for the study of disease states in otherwise healthy animals. This can be particularly useful for diseases that are poorly understood and otherwise difficult to accurately model in living animals. For instance, it can be difficult to test and/or study disease states due to the lack of available animals exhibiting the disease state. Moreover, certain embodiments allow for reversible disease states, which can be particularly useful in establishing baseline/control points for testing and/or for testing the effects of a treatment on the same animal when exhibiting the disease state and when not exhibiting the disease state.

Certain aspects of the present disclosure are directed to a method that includes modifying (e.g., elevating or lowering) an excitation/inhibition (E/I) balance in a targeted neural circuit in a prefrontal cortex of a subject/patient. For instance, the E/I balance is changed to a level that preserves the responsiveness of the targeted neural circuit to intrinsic electrical activity while symptoms of a disorder are temporally increased. While the E/I balance is changed, a stimulus is introduce to the subject/patient and the symptoms of the disorder are monitored. The subject can be a test animal that is healthy, or an animal model of a disorder. The result of the manipulation is either a transient recapitulation of disease symptoms (in an otherwise healthy animal) or alleviation of symptoms (in an animal model of a neurological disorder). In certain more specific embodiments, the monitoring of the symptoms also includes assessing the efficacy of the stimulus in mitigating the symptoms of the disorder. Various other possibilities exist, some of which are discussed in more detail herein.

BRIEF DESCRIPTION OF THE DRAWINGS

Various example embodiments may be more completely understood in consideration of the following description and the accompanying drawing, in which.

Figure 1:
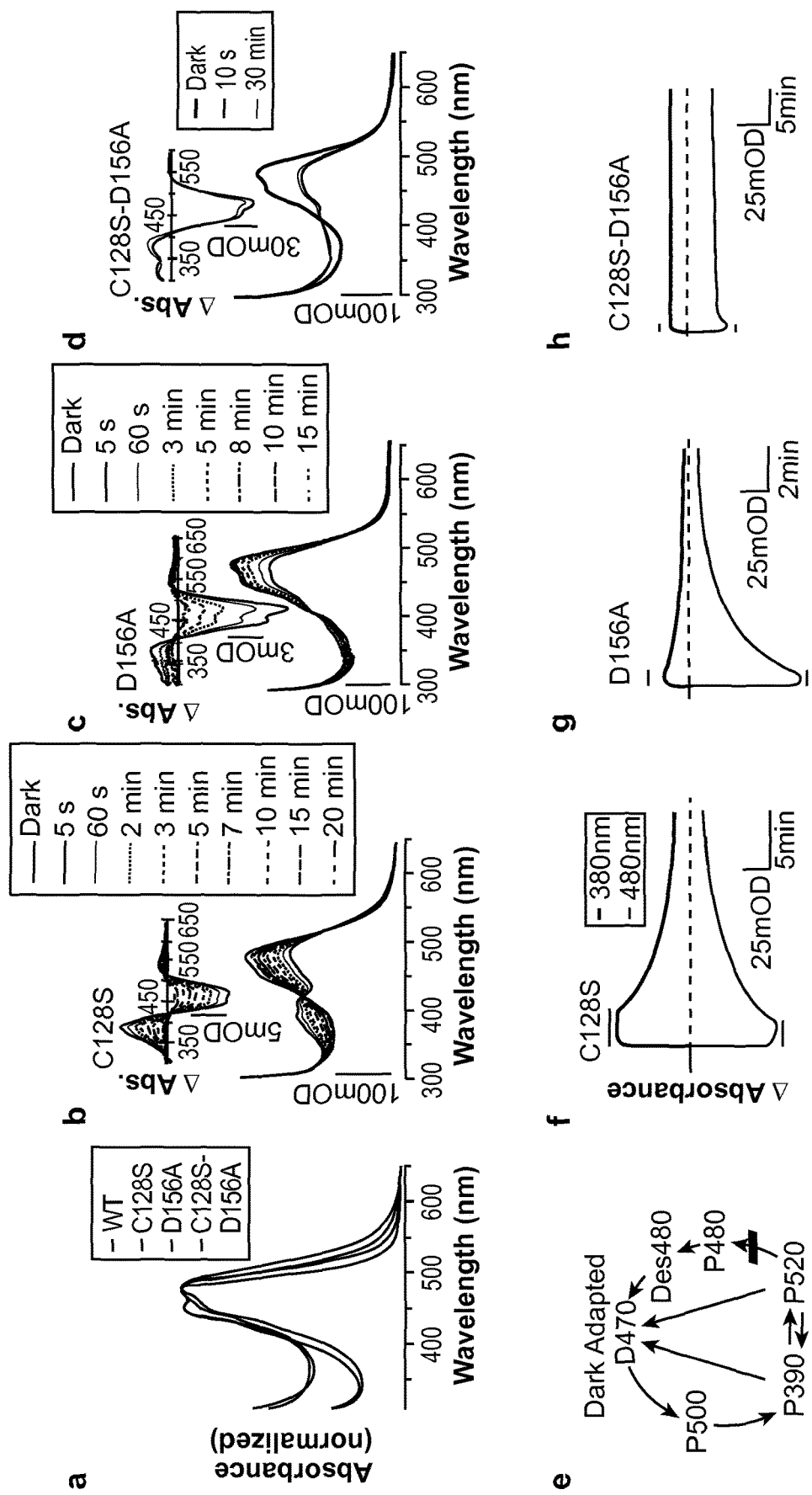
FIG. 1: Kinetic and absorbance properties of a fully stabilized SFO. (a) Normalized absorbance spectra of dark-adapted wild type ChR2, ChR2-C128S, ChR2-D156A and ChR2-C128S/D156A (SSFO). (b-d) Absorption spectra recorded after illumination with 450 nm light for 30 seconds. Absorption difference spectra taken from the corresponding absorption spectra are shown in the insets. Spectra were collected at the indicated times after the end of illumination; note prominent recovery after 3 min in the single mutants, in contrast to the double mutant. (e) Simplified photocycle scheme; in C128/D156 mutants the transition P520 to P480 is likely slowed down or blocked, avoiding the desensitized state Des470 which cannot be reactivated with 470 nm light. (f-h) Monochromatic absorption changes recorded at the indicated wavelength before, during and after illumination with 450 nm light for all three variants, highlighting the distinct stability of the double mutant.

While the present disclosure is amenable to various modifications and alternative forms, specifics thereof have been shown by way of example in the drawing and will be described in detail. It should be understood, however, that the intention is not to limit the present disclosure to the particular embodiments described. On the contrary, the intention is to cover all modifications, equivalents, and alternative falling within the scope of the present disclosure including aspects defined in the claims.

DETAILED DESCRIPTION

This invention provides, inter alia, animal cells, non-human animals, and brain slices comprising cells expressing stabilized step function opsin proteins on their plasma membranes, and methods of using the stabilized step function opsin proteins to selectively depolarize excitatory or inhibitory neurons residing in the same microcircuit in the pre-frontal cortex. The step function opsins, or SFOs, are ChR2 light-activated cation channel proteins that can induce prolonged stable excitable states in neurons upon exposure to blue light and then be reversed upon exposure to green or yellow light. The SFOs were developed to implement bistable changes in excitability of targeted populations operating on timescales up to 4 orders of magnitude longer than that of wild type (wt) ChR2 for more stable state modulation (SFOs: up to 10-100 seconds). While these opsin genes delivered a new kind of optogenetic control complementary to that of conventional channelrhodopsins designed to control individual action potentials, the timescale was still not suitable for evaluating prolonged and complex mammalian behaviors over many minutes.

Subsequent work by the inventors has further developed the initial SFO concept, with mutation of the C128 proton networking partner D156 for additional extension of the photocycle and lifetime of the open state. This "stabilized step function opsin" (SSFO) protein possesses unique physiochemical properties which permit experimental manipulation of cortical E/I elevations and the ability to monitor gamma oscillations in cortical slices. This new tool, known as a stabilized step function opsin (SSFO), enables stable circuit modulation for time periods that are sufficient for temporally precise and complex behavioral experiments over many minutes in the absence of ongoing light activation, external fiber optic attachments, and even without any optical hardware brain penetration at all. Additionally, due to the phenomena of photon integration—a property that renders neurons expressing the SSFO extremely light sensitive—cells expressing these proteins on their plasma membranes are able to be activated with light pulses that can have a light power density in the low $\mu W/mm^{-2}$ range and at least 3 mm deep into brain tissue from the light source. These unique light-sensitive step function opsin proteins can be expressed in either excitatory or inhibitory neural circuits, such as in the prefrontal cortex of nonhuman animals, which can then be depolarized in response to light having particular wavelengths, thus permitting experimental manipulation of cortical E/I balances. Furthermore, brain slices from non-human animals containing cortical excitatory or inhibitory neurons expressing the stabilized step function opsin proteins disclosed herein can be used to search for chemical compounds which can selectively inhibit the depolarization of either excitatory or inhibitory neurons residing within a neural circuit. These cortical neurons may be responsible for or involved with the social and cognitive behavioral defects associated with neurological disorders such as schizophrenia and/or autism spectrum disorder.

General Techniques

The practice of the present invention will employ, unless otherwise indicated, conventional techniques of molecular biology, microbiology, cell biology, biochemistry, nucleic acid chemistry, and immunology, which are well known to those skilled in the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994); Harlow and Lane (1988) *Antibodies, A Laboratory Manual*, Cold Spring Harbor Publications, New York; Harlow and Lane (1999) *Using Antibodies: A Laboratory Manual*, Cold Spring Harbor Laboratory Press, Cold Spring Harbor, N.Y. (jointly referred to herein as "Harlow and Lane"), Beaucage et al. eds., *Current Protocols in Nucleic Acid Chemistry*, John Wiley & Sons, Inc., New York, 2000), *Handbook of Experimental Immunology*, 4th edition (D. M. Weir & C. C. Blackwell, eds., Blackwell Science Inc., 1987); and *Gene Transfer Vectors for Mammalian Cells* (J. M. Miller & M. P. Calos, eds., 1987).

Definitions

As used herein, the singular form "a", "an", and "the" includes plural references unless indicated otherwise.

An "animal" can be a vertebrate, such as any common laboratory model organism, or a mammal. Mammals include, but are not limited to, humans and non-human primates, farm animals, sport animals, pets, mice, rats, and other rodents.

An "amino acid substitution" or "mutation" as used herein means that at least one amino acid component of a defined amino acid sequence is altered or substituted with another amino acid leading to the protein encoded by that amino acid sequence having altered activity or expression levels within a cell.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

SSFO Proteins and Cells Expressing the Same

Previously described SFOs capitalize on slower channel deactivation kinetics, as introduced by mutation of ChR2-C128, which was chosen based on the homology between channelrhodopsin-2 (ChR2) and bacteriorhodopsin (BR), in which similar mutations led to moderate slowing of the photocycle. T90, the BR homolog of ChR2-C128, is hydrogen-bonded to D115 of BR; these two amino acids are thought to work in concert to stabilize the all-trans conformation of the retinal chromophore, and ChR2-D156 is the homolog of BR D115. If C128 and D156 modulate ChR2 closure solely via their presumptive shared hydrogen bond, then a combination mutation of these two residues would not be expected to generate significantly greater effects on channel kinetics than either mutation alone. However, contrary to expectations, neurons expressing the ChR2-C128S/D156A double mutant gave rise to sustained photocurrents that were far more stable than those from cells expressing either single mutant alone.

In some aspects, the invention includes proteins comprising substituted or mutated amino acid sequences, wherein the mutant protein retains the characteristic light-activatable nature of the precursor SFO protein but may also possess altered properties in some specific aspects. For example, the mutant light-activated SFO proteins described herein may exhibit an increased level of expression both within an animal cell or on the animal cell plasma membrane; an increased level of sustained photocurrents in response to a first wavelength of light; a faster but less complete deactivation when exposed to a second wavelength of light; and/or a combination of traits whereby the SFO protein possess the properties of low desensitization, fast deactivation, and/or strong expression in animal cells.

Light-activated SFO proteins comprising amino acid substitutions or mutations include those in which one or more amino acid residues have undergone an amino acid substitution while retaining the ability to respond to light and the ability to control the polarization state of a plasma membrane. For example, light-activated proteins comprising amino acid substitutions or mutations can be made by substituting one or more amino acids into the amino acid sequence corresponding to SEQ ID NO:1, SEQ ID NO:2, SEQ ID NO:3, or SEQ ID NO:4. In some embodiments, the invention includes proteins comprising altered amino acid sequences in comparison with the amino acid sequence in SEQ ID NO: 1, SEQ ID NO:2, SEQ ID NO:3, or SEQ ID NO:4, wherein the altered light-activated stabilized step function opsin protein retains the characteristic light-activated nature and/or the ability to regulate ion flow across plasma membranes of the protein with the amino acid sequence represented in SEQ ID NO:1, SEQ ID NO:2, SEQ ID NO:3, or SEQ ID NO:4 but may have altered properties in some specific aspects.

Amino acid substitutions in a native protein sequence may be conservative or non-conservative and such substituted amino acid residues may or may not be one encoded by the genetic code. The standard twenty amino acid "alphabet" is divided into chemical families based on chemical properties of their side chains. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and side chains having aromatic groups (e.g., tyrosine, phenylalanine, tryptophan, histidine). A "conservative amino acid substitution" is one in which the amino acid residue is replaced with an amino acid residue having a chemically similar side chain (i.e., replacing an amino acid possessing a basic side chain with another amino acid with a basic side chain). A "non-conservative amino acid substitution" is one in which the amino acid residue is replaced with an amino acid residue having a chemically different side chain (i.e., replacing an amino acid having a basic side chain with an amino acid having an aromatic side chain). The amino acid substitutions may be conservative or non-conservative. Additionally, the amino acid substitutions may be located in the SFO retinal binding pocket, in one or more of the SFO intracellular loop domains, and/or in both the retinal binding pocket or the intracellular loop domains.

Provided herein, therefore, are light-activated stabilized step function opsin proteins that may have specific amino acid substitutions at key positions throughout the retinal binding pocket of the protein. For information regarding the retinal binding pocket of light sensitive polypeptides, see Greenhalgh et al., *J. Biol. Chem.*, 268, 20305-20311 (1993), the disclosure of which is hereby incorporated herein in its entirety. In some embodiments, the SFO protein can have a mutation at amino acid residue C128 of SEQ ID NO:1. In some embodiments, the SFO protein can have a mutation at amino acid residue D156 of SEQ ID NO:1. In other embodiments, the SFO protein can have a mutation at both amino acid residues C128 and D156 of SEQ ID NO:1 (SSFO). In some embodiments, each of the disclosed mutant stabilized step function opsin proteins can have specific properties and characteristics for use in depolarizing the membrane of an animal cell in response to light.

Accordingly, in one aspect there is provided a light-activated SSFO protein expressed on a cell plasma membrane capable of mediating a depolarizing current in the cell when the cell is illuminated with light, wherein the protein exhibits rapid step-like activation in response to a single pulse of light having a first wavelength and deactivation in response to a pulse of light having a second wavelength; wherein the depolarizing current in the cell is maintained for up to about five, about ten, about fifteen, or about twenty minutes. In some embodiments, the protein comprises the amino acid sequence of ChR2, ChR1, VChR1, or VChR2 with amino acid substitutions at amino acid residues corresponding to C128 and D156 of the amino acid sequence of ChR2 (See, e.g., FIG. 1B of International Patent Application Publication No. WO 2009/131837, which is incorporated by reference herein, illustrating conservation of amino acid residues corresponding to C128 and D156 of the amino acid sequence of ChR2 between several species of channelrhopsin cation channels; see also Kianianmomeni et al., Plant Physiol., 2009, 151:347-356, which is incorporated by reference herein in its entirety). In other embodiments, the light-activated SSFO protein can comprise an amino acid sequence at least 90%, 91%, 92%, 93%, 94%, 95%, 96%, 97%, 98%, 99%, or 100% identical to the sequence shown in SEQ ID NO:1 without the signal peptide sequence. In other embodiments, the light-activated SSFO protein can comprise an amino acid sequence at least 90%, 91%, 92%, 93%, 94%, 95%, 96%, 97%, 98%, 99%, or 100% identical to the sequence shown in SEQ ID NO:1. In other embodiments, the light-activated SSFO protein can comprise an amino acid sequence at least 90%, 91%, 92%, 93%, 94%, 95%, 96%, 97%, 98%, 99%, or 100% identical to the sequence shown in SEQ ID NO:2. In other embodiments, the light-activated SSFO protein can comprise an amino acid sequence at least 90%, 91%, 92%, 93%, 94%, 95%, 96%, 97%, 98%, 99%, or 100% identical to the sequence shown in SEQ ID NO:3. In another embodiment, the light-activated SSFO protein can comprise an amino acid sequence at least 90%, 91%, 92%, 93%, 94%, 95%, 96%, 97%, 98%, 99%, or 100% identical to the sequence shown in SEQ ID NO:4. In some embodiments, the signal peptide sequence in the SSFO proteins is deleted or substituted with a signal peptide sequence from a different protein. In some embodiments, the substitution at amino acid residues corresponding to C128 and D156 of the amino acid sequence of ChR2 are conservative amino acid substitutions. In other embodiments, the substitution at amino acid residues corresponding to C128 and D156 of the amino acid sequence of ChR2 are non-conservative amino acid substitutions. In some embodiments, the substitution at the amino acid residue corresponding to C128 of the amino acid sequence of ChR2 is a substitution to serine. In other embodiments, the substitution at the amino acid residue corresponding to D156 of the amino acid sequence of ChR2 is a substitution to a non-acidic amino acid. In another embodiment, the substitution at the amino acid residue corresponding to D156 of the amino acid sequence of ChR2 is a substitution to alanine. In some embodiments, the protein can further comprise a C-terminal fluorescent protein. In some specific embodiments, the C-terminal fluorescent protein can be enhanced yellow fluorescent protein (EYFP), green fluorescent protein (GFP), cyan fluorescent protein (CFP), or red fluorescent protein (RFP). In some embodiments, the second light-activated protein can be capable of mediating a hyperpolarizing current in the cell when the cell is illuminated with light. In some embodiments the second light-activated protein can be NpHR, eNpHR2.0, eNpHR3.0, eNpHR3.1, GtR3, or a C1V1 chimeric protein as described in International Patent Application No: PCT/US2011/028893 and U.S. Provisional Patent Application Nos. 61/410,736 and 61/410,744, the disclosure of each of which is incorporated by reference herein in their entirety.

In some embodiments, the C1V1 chimeric protein comprises a light-activated protein expressed on the cell membrane, wherein the protein is a chimeric protein derived from VChR1 from *Volvox carteri* and ChR1 from *Chlamydomonas reinhardti*, wherein the protein comprises the amino acid sequence of VChR1 having at least the first and second transmembrane helices replaced by the first and second transmembrane helices of ChR1; is responsive to light; and is capable of mediating a depolarizing current in the cell when the cell is illuminated with light. In some embodiments wherein the protein further comprises a replacement within the intracellular loop domain located between the second and third transmembrane helices of the chimeric light responsive protein, wherein at least a portion of the intracellular loop domain is replaced by the corresponding portion from the ChR1. In another embodiment, the portion of the intracellular loop domain of the CIV1 chimeric protein is replaced with the corresponding portion from the ChR1 extending to amino acid residue A145 of the ChR1. In other embodiments, the C1V1 chimeric protein further comprises a replacement within the third transmembrane helix of the chimeric light responsive protein, wherein at least a portion of the third transmembrane helix is replaced by the corresponding sequence of ChR1. In another embodiment, the portion of the intracellular loop domain of the C1V1 chimeric protein is replaced with the corresponding portion from the ChR1 extending to amino acid residue W163 of the ChR1.

In some embodiments of the stabilized step function opsin proteins provided herein, the light having a first wavelength can be blue light. In other embodiments, said light having a first wavelength can be about 445 nm. In another embodiment, said light having a second wavelength can be green light or yellow light. In other embodiments, said light having a second wavelength can be about 590 nm. In other embodiments, said light having a second wavelength can be between about 390-400 nm, inclusive, as well as every number within this range. In some embodiments, the light-activated stabilized step function opsin proteins described herein can be activated by light pulses that can have a duration for any of about 1 millisecond (ms), about 2 ms, about 3, ms, about 4, ms, about 5 ms, about 6 ms, about 7 ms, about 8 ms, about 9 ms, about 10 ms, about 15 ms, about 20 ms, about 25 ms, about 30 ms, about 35 ms, about 40 ms, about 45 ms, about 50 ms, about 60 ms, about 70 ms, about 80 ms, about 90 ms, about 100 ms, about 200 ms, about 300 ms, about 400 ms, about 500 ms, about 600 ms, about 700 ms, about 800 ms, about 900 ms, about 1 sec, about 1.25 sec, about 1.5 sec, or about 2 sec, inclusive, including any times in between these numbers. In some embodiments, the light-activated stabilized step function opsin proteins described herein can be activated by light pulses that can have a light power density of any of about 1 $\mu W\ mm^{-2}$, about 2 $\mu W\ mm^{-2}$, about 3 $\mu W\ mm^{-2}$, about 4 $\mu W\ mm^{-2}$, about 5 $\mu W\ mm^{-2}$, about 6 $\mu W\ mm^{-2}$, about 7 $\mu W\ mm^{-2}$, about 8 $\mu W\ mm^{-2}$, about 9 $\mu W\ mm^{-2}$, about 10 $\mu W\ mm^{-2}$, about 11 $\mu W\ mm^{-2}$, about 12 $\mu W\ mm^{-2}$, about 13 $\mu W\ mm^{-2}$, about 14 $\mu W\ mm^{-2}$, about 15 $\mu W\ mm^{-2}$, about 16 $\mu W\ mm^{-2}$, about 17 $\mu W\ mm^{-2}$, about 18 $\mu W\ mm^{-2}$, about 19 $\mu W\ mm^{-2}$, or about 20 $\mu W\ mm^{-2}$, inclusive, including any values between these numbers. In other embodiments, the light-activated proteins can be activated by light pulses that can have a light power density of any of about 1 $mW\ mm^{-2}$, about 2 $mW\ mm^{-2}$, about 3 $mW\ mm^{-2}$, about 4 $mW\ mm^{-2}$, about 5 $mW\ mm^{-2}$, about 6 $mW\ mm^{-2}$, about 7 $mW\ mm^{-2}$, about 8 $mW\ mm^{-2}$, about 9 $mW\ mm^{-2}$, about 10 $mW\ mm^{-2}$, about 11 $mW\ mm^{-2}$, about 12 $mW\ mm^{-2}$, about 13 $mW\ mm^{-2}$, about 14 $mW\ mm^{-2}$, about 15 $mW\ mm^{-2}$, about 16 $mW\ mm^{-2}$, about 17 $mW\ mm^{-2}$, about 18 $mW\ mm^{-2}$, about 19 $mW\ mm^{-2}$, about 20 $mW\ mm^{-2}$, about 21 $mW\ mm^{-2}$, about 22 $mW\ mm^{-2}$, about 23 $mW\ mm^{-2}$, about 24 $mW\ mm^{-2}$, or about 25 $mW\ mm^{-2}$, inclusive, including any values between these numbers.

In some embodiments, the light-activated stabilized step function opsin proteins described herein can maintain a sustained photocurrent for about 20 minutes. In other embodiments, the light-activated stabilized step function opsin proteins described herein can maintain a sustained photocurrent for any of about 10, 11, 12, 13, 14, 15, 16, 17, 18, 19, 20, 21, 22, 23, 24, 25, 26 27, 28, 29, or 30 minutes, inclusive, including for any times in between these numbers. In other embodiments, the photocycle progression of any of the light-activated stabilized step function opsin proteins described herein is completely blocked after the protein is illuminated with said single pulse of light having a first wavelength.

In some aspects of the light-activated stabilized step function opsin proteins described herein, the cell can be an animal cell. In some embodiments, the animal cell can be a neuronal cell, a cardiac cell, or a stem cell. In some embodiments, the animal cell can be a neuronal cell. In other embodiments, the animal cells comprise neurons that effect social behavior when depolarized. In some embodiments, the neuronal cell is a neuron that changes innate social behavior and/or conditioned behavior when depolarized. In other embodiments, the animal cells comprise neurons that give rise to the social and cognitive defects in autism and/or schizophrenia when depolarized. In other embodiments, the neuronal cell can be an excitatory neuron located in the pre-frontal cortex of a non-human animal. In other embodiments, the excitatory neuron can be a pyramidal neuron. In some embodiments the neuronal cell can be an inhibitory neuron located in the pre-frontal cortex of a non-human animal. In still other embodiments, the inhibitory neuron can be a parvalbumin neuron. In some embodiments, the inhibitory and excitatory neurons can be in a living non-human animal.

In other aspects of the light-activated stabilized step function opsin proteins, the cells can be neurons in a living brain slice from a non-human animal. In some embodiments, the brain slices are coronal brain slices. In some embodiments, the brain slices are from the pre-frontal cortex of a non-human animal. In other embodiments, the brain slices comprise neurons that effect social behavior when depolarized. In some embodiments, the brain slices comprise neurons that change innate social behavior and/or conditioned behavior when depolarized. In other embodiments, the brain slices comprise neurons that give rise to the social and cognitive defects in autism and/or schizophrenia when depolarized.

In some aspects, the stabilized step function opsin proteins described herein may be modified by the addition of one or more amino acid sequence motifs which enhance transport to the plasma membranes of mammalian cells. Light-activated opsin proteins are derived from evolutionarily simpler organisms and therefore may not be expressed or tolerated by mammalian cells or may exhibit impaired subcellular localization when expressed at high levels in mammalian cells. Consequently, in some embodiments, the stabilized step function opsin proteins described herein may be fused to one or more amino acid sequence motifs selected from the group consisting of a signal peptide, an endoplasmic reticulum (ER) export signal, a membrane trafficking signal, and an N-terminal golgi export signal. The one or more amino acid sequence motifs which enhance the light-activated stabilized step function opsin proteins transport to the plasma membranes of mammalian cells can be fused to the N-terminus, the C-terminus, or to both the N- and C-terminal ends of the light-activated protein. Optionally, the light-activated protein and the one or more amino acid sequence motifs may be separated by a linker. In some embodiments, the stabilized step function opsin protein is modified by the addition of a trafficking signal (ts) which enhances transport of the protein to the cell plasma membrane. In some embodiments, the trafficking signal is derived from the amino acid sequence of the human inward rectifier potassium channel $K_{ir}2.1$. In some embodiments, the trafficking signal comprises the amino acid sequence KSRITSEGEYIPLDQIDINV. In other embodiments, the light-activated stabilized step function opsin protein is modified by the addition of a signal peptide (e.g., which enhances transport to the plasma membrane). The signal peptide may be fused to the C-terminus of the core amino acid sequence or may be fused to the N-terminus of the core amino acid sequence. In some embodiments, the signal peptide is linked to the core amino acid sequence by a linker. The linker can comprise any of 5, 10, 20, 30, 40, 50, 75, 100, 125, 150, 175, 200, 225, 250, 275, 300, 400, or 500 amino acids in length. In some embodiments, the signal peptide comprises the amino acid sequence MDYGGALSAVGRELLFVTNPV-VVNGSVLVPEDQCYCAGWIESRGTNG. In other embodiments, the light-activated stabilized step function opsin protein is modified by the addition of an endoplasmic reticulum (ER) export signal. The ER export signal may be fused to the C-terminus of the core amino acid sequence or may be fused to the N-terminus of the core amino acid sequence. In some embodiments, the ER export signal is linked to the core amino acid sequence by a linker. The linker can comprise any of 5, 10, 20, 30, 40, 50, 75, 100, 125, 150, 175, 200, 225, 250, 275, 300, 400, or 500 amino acids in length. In some embodiments, the ER export signal comprises the amino acid sequence FXYENE, where X can be any amino acid. In some embodiments, the ER export signal comprises the amino acid sequence VXXSL, where X can be any amino acid. In some embodiments, the ER export signal comprises the amino acid sequence FCYENEV.

Animal Cells, Non-human Animals, and Brain Slices

Provided herein are cells comprising the light activated chimeric proteins disclosed herein. In some embodiments, the cells are animal cells. In some embodiments, the animal cells comprise the protein corresponding to SEQ ID NO: 1. In other embodiments, the animal cells comprise the stabilized step function opsin proteins disclosed herein. In one embodiment, the animal cell can be a neuronal cell. In some embodiments, the animal cells are from the pre-frontal cortex of a non-human animal. In other embodiments, the animal cells comprise neurons that effect social behavior when depolarized. In some embodiments, the neuronal cell is a neuron that changes innate social behavior and/or conditioned behavior when depolarized. In other embodiments, the animal cells comprise neurons that give rise to the social and cognitive defects in autism and/or schizophrenia when depolarized. In some embodiments the neuronal cell can be an excitatory neuron located in the pre-frontal cortex of a non-human animal. In other embodiments, the excitatory neuron can be a pyramidal neuron. In some embodiments the neuronal cell can be an inhibitory neuron located in the pre-frontal cortex of a non-human animal. In still other embodiments, the inhibitory neuron can be a parvalbumin neuron.

Also provided herein are non-human animals comprising the proteins disclosed herein. In some embodiments, the non-human animals comprise the protein corresponding to SEQ ID NO: 1. In some embodiments, the animals comprise the stabilized step function opsin proteins disclosed herein. In some embodiments, the animals comprising the stabilized step function opsin proteins disclosed herein are transgenically expressing said stabilized step function opsin proteins. In other embodiments, the animals comprising the stabilized step function opsin proteins described herein have been virally transfected with a vector carrying the stabilized step function opsin proteins such as, but not limited to, an adenoviral vector. In some embodiments, the animals comprising the stabilized step function opsin proteins disclosed herein exhibit changes in behavior when said stabilized step function opsin proteins are depolarized by activation with light. In other embodiments, the animals comprising the stabilized step function opsin proteins disclosed herein exhibit changes in innate and learned social behaviors when said stabilized step function opsin proteins are depolarized by activation with light. In other embodiments, the animals comprising the stabilized step function opsin proteins disclosed herein exhibit changes in conditioned behaviors when said stabilized step function opsin proteins are depolarized by activation with light.

Provided herein are living brain slices from a non-human animal comprising the stabilized step function opsin proteins described herein. In some embodiments, the brain slices are from non-human animals transgenically expressing the stabilized step function opsin proteins described herein. In other embodiments, the brain slices are from non-human animals that have been virally transfected with a vector carrying said stabilized step function opsin proteins such as, but not limited to, an adenoviral vector. In some embodiments, the brain slices are coronal brain slices. In some embodiments, the brain slices are from the pre-frontal cortex of a non-human animal. In other embodiments, the brain slices comprise neurons that effect social behavior when depolarized. In some embodiments, the brain slices comprise neurons that change innate social behavior and/or conditioned behavior when depolarized. In other embodiments, the brain slices comprise neurons that give rise to the social and cognitive defects in autism and/or schizophrenia when depolarized. In some embodiments, the brain slices are any of about 100 µm, about 150 µm, about 200 µm, about 250 µm, about 300 µm, about 350 µm, about 400 µm, about 450 µm, or about 500 µm thick, inclusive, including any thicknesses in between these numbers.

Polynucleotides, Promoters, and Vectors

Provided herein are isolated polynucleotides that encode stabilized step function opsin proteins that have at least one activity of a step function opsin protein. The disclosure provides isolated, synthetic, or recombinant polynucleotides comprising a nucleic acid sequence having at least about 70%, e.g., at least about 71%, 72%, 73%, 74%, 75%, 76%, 77%, 78%, 79%, 80%, 81%, 82%, 83%, 84%, 85%, 86%, 87%, 88%; 89%, 90%, 91%, 92%, 93%, 94%, 95%, 96%, 97%, 98%, or 99%, or complete (100%) sequence identity to the nucleic acid of SEQ ID NO:2 over a region of at least about 10, e.g., at least about 15, 20, 25, 30, 35, 40, 45, 50, 75, 100, 150, 200, 250, 300, 350, 400, 450, 500, 550, 600, 650, 700, 750, 800, 850, 900, 950, or 1000 nucleotides.

The disclosure specifically provides a polynucleotide comprising a nucleic acid sequence encoding a stabilized step function opsin protein and/or a mutant variant thereof. For example, the disclosure provides an isolated polynucleotide molecule, wherein the polynucleotide molecule encodes a protein comprising an amino acid sequence with at least 90%, 91%, 92%, 93%, 94%, 95%, 96%, 97%, 98%, 99% or 100% sequence identity to the amino acid sequence of SEQ ID NO: 1. The disclosure also provides an isolated polynucleotide molecule, wherein the polynucleotide molecule encodes a protein comprising an amino acid sequence with at least 90%, 91%, 92%, 93%, 94%, 95%, 96%, 97%, 98%, 99% or 100% sequence identity to the amino acid sequence of SEQ ID NO:2. The disclosure moreover provides an isolated polynucleotide molecule, wherein the polynucleotide molecule encodes a protein comprising an amino acid sequence with at least 90%, 91%, 92%, 93%, 94%, 95%, 96%, 97%, 98%, 99% or 100% sequence identity to the amino acid sequence of SEQ ID NO:3. The disclosure additionally provides an isolated polynucleotide molecule, wherein the polynucleotide molecule encodes a protein comprising an amino acid sequence with at least 90%, 91%, 92%, 93%, 94%, 95%, 96%, 97%, 98%, 99% or 100% sequence identity to the amino acid sequence of SEQ ID NO:4.

The disclosure also provides expression cassettes and/or vectors comprising the above-described nucleic acids. Suitably, the nucleic acid encoding a stabilized step function opsin protein of the disclosure is operably linked to a promoter. Promoters are well known in the art. Any promoter that functions in the host cell can be used for expression of SSFO and/or any variant thereof of the present disclosure. Initiation control regions or promoters, which are useful to drive expression of a SSFO protein or variant thereof in a specific animal cell are numerous and familiar to those skilled in the art. Virtually any promoter capable of driving these nucleic acids can be used.

Specifically, where recombinant expression of SSFO proteins, such as the proteins described herein, in an excitatory neural cell is desired, a human calmodulin-dependent protein kinase II alpha (CaMKIIα) promoter may be used. In other embodiments, an elongation factor 1a (EF-1a) promoter in conjunction with a Cre-inducible recombinant AAV vector can be used with parvalbumin-Cre transgenic mice to target expression SSFO proteins to inhibitory neurons.

Also provided herein are vectors comprising the polynucleotides disclosed herein encoding a stabilized step function opsin proteins or any variant thereof. The vectors that can be administered according to the present invention also include vectors comprising a polynucleotide which encodes an RNA (e.g., an mRNA) that when transcribed from the polynucleotides of the vector will result in the accumulation of light-activated stabilized step function opsin proteins on the plasma membranes of target animal cells. Vectors which may be used, include, without limitation, lentiviral, HSV, adenoviral, and andeno-associated viral (AAV) vectors. Lentiviruses include, but are not limited to HIV-1, HIV-2, SIV, FIV and EIAV. Lentiviruses may be pseudotyped with the envelope proteins of other viruses, including, but not limited to VSV, rabies, Mo-MLV, baculovirus and Ebola. Such vectors may be prepared using standard methods in the art.

In some embodiments, the vector is a recombinant AAV vector. AAV vectors are DNA viruses of relatively small size that can integrate, in a stable and sitespecific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

AAV vectors may be prepared using standard methods in the art. Adeno-associated viruses of any serotype are suitable (see, e.g., Blacklow, pp. 165-174 of "*Parvoviruses and Human Disease*" J. R. Pattison, ed. (1988); Rose, *Comprehensive Virology* 3:1, 1974; P. Tattersall "The Evolution of Parvovirus Taxonomy" in *Parvoviruses* (J R Kerr, S F Cotmore. M E Bloom, R M Linden, C R Parrish, Eds.) p5-14, Hudder Arnold, London, UK (2006); and D E Bowles, J E Rabinowitz, R J Samulski "*The Genus Dependovirus*" (J R Kerr, S F Cotmore. M E Bloom, R M Linden, C R Parrish, Eds.) p15-23, Hudder Arnold, London, UK (2006), the disclosures of which are hereby incorporated by reference herein in their entireties). Methods for purifying for vectors may be found in, for example, U.S. Pat. Nos. 6,566,118, 6,989,264, and 6995006 and International Patent Application Publication No.: WO/1999/011764 titled "Methods for Generating High Titer Helper-free Preparation of Recombinant AAV Vectors", the disclosures of which are herein incorporated by reference in their entirety. Preparation of hybrid vectors is described in, for example, PCT Application No. PCT/US2005/027091, the disclosure of which is herein incorporated by reference in its entirety. The use of vectors derived from the AAVs for transferring genes in vitro and in vivo has been described (See e.g., International Patent Application Publication Nos: WO 91/18088 and WO 93/09239; U.S. Pat. Nos. 4,797,368, 6,596,535, and 5,139,941; and European Patent No: 0488528, all of which are herein incorporated by reference in their entirety). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In some embodiments, the vector(s) for use in the methods of the invention are encapsidated into a virus particle (e.g. AAV virus particle including, but not limited to, AAV1, AAV2, AAV3, AAV4, AAV5, AAV6, AAV7, AAV8, AAV9, AAV10, AAV11, AAV12, AAV13, AAV14, AAV15, and AAV16). Accordingly, the invention includes a recombinant virus particle (recombinant because it contains a recombinant polynucleotide) comprising any of the vectors described herein. Methods of producing such particles are known in the art and are described in U.S. Pat. No. 6,596,535.

For the animal cells described herein, it is understood that one or more vectors may be administered to neural cells, heart cells, or stem cells. If more than one vector is used, it is understood that they may be administered at the same or at different times to the animal cells.

Methods of the Invention

Provided herein are methods for depolarizing excitatory or inhibitory neurons residing in a microcircuit by expressing in those neurons the light-activated stabilized step function opsin proteins described herein. In some aspects, there is a provided a method for using the stabilized step function opsin proteins described herein by activating proteins with light. The stabilized step function opsin proteins disclosed herein can be expressed in an excitatory neuron or in an inhibitory neuron. In other embodiments, method for using the stabilized step function opsin proteins disclosed herein can be in a living non-human animal or in a living brain slice from a non-human animal. In other aspects, there is provided a method for identifying a chemical compound that inhibits the depolarization of excitatory neurons in the prefrontal cortex of a non-human animal. In other aspects, there is provided a method for identifying a chemical compound that restores an innate social behavior and/or communication in a non-human animal.

Methods for Using SSFO Proteins

Provided herein are methods for using the stabilized step function opsin proteins disclosed herein comprising activating the proteins with light having a first wavelength. In some embodiments, the proteins can be activated with light having a first wavelength that can be blue light. In other embodiments, said light having a first wavelength can be about 445 nm.

In another aspect of the methods for using the compositions disclosed herein, the stabilized step function opsin proteins disclosed herein can be deactivated with light having a second wavelength. In some embodiments, said light having a second wavelength can be green light or yellow light. In other embodiments, said light having a second wavelength can be about 590 nm. In other embodiments, said light having a second wavelength can be between about 390-400 nm, inclusive, as well as every number within this range.

In some aspects of the methods provided herein, the stabilized step function opsin proteins can be activated by light pulses that can have a duration for any of about 1 millisecond (ms), about 2 ms, about 3, ms, about 4, ms, about 5 ms, about 6 ms, about 7 ms, about 8 ms, about 9 ms, about 10 ms, about 15 ms, about 20 ms, about 25 ms, about 30 ms, about 35 ms, about 40 ms, about 45 ms, about 50 ms, about 60 ms, about 70 ms, about 80 ms, about 90 ms, about 100 ms, about 200 ms, about 300 ms, about 400 ms, about 500 ms, about 600 ms, about 700 ms, about 800 ms, about 900 ms, about 1 sec, about 1.25 sec, about 1.5 sec, or about 2 sec, inclusive, including any times in between these numbers. In some embodiments of the methods provided herein, the stabilized step function opsin proteins can be activated by light pulses that can have a light power density of any of about 1 $\mu W\ mm^{-2}$, about 2 $\mu W\ mm^{-2}$, about 3 $\mu W\ mm^{-2}$, about 4 $\mu W\ mm^{-2}$, about 5 $\mu W\ mm^{-2}$, about 6 $\mu W\ mm^{-2}$, about 7 $\mu W\ mm^{-2}$, about 8 $\mu W\ mm^{-2}$, about 9 $\mu W\ mm^{-2}$, about 10 $\mu W\ mm^{-2}$, about 11 $\mu W\ mm^{-2}$, about 12 $\mu W\ mm^{-2}$, about 13 $\mu W\ mm^{-2}$, about 14 $\mu W\ mm^{-2}$, about 15 $\mu W\ mm^{-2}$, about 16 $\mu W\ mm^{-2}$, about 17 $\mu W\ mm^{-2}$, about 18 $W\ mm^{2}$, about 19 $\mu W\ mm^{-2}$, or about 20 $\mu W\ mm^{-2}$, inclusive, including any values between these numbers. In other embodiments, the light-activated stabilized step function opsin proteins can be activated by light pulses that can have a light power density of any of about 1 $mW\ mm^{-2}$ about 2 $mW\ mm^{-2}$, about 3 $mW\ mm^{-2}$, about 4 $mW\ mm^{-2}$, about 5 $mW\ mm^{-2}$, about 6 $mW\ mm^{-2}$, about 7 $mW\ mm^{-2}$, about 8 $mW\ mm^{-2}$, about 9 $mW\ mm^{-2}$, about 10 $mW\ mm^{-2}$, about 11 $mW\ mm^{-2}$, about 12 $mW\ mm^{-2}$, about 13 $mW\ mm^{-2}$, about 14 $mW\ mm^{-2}$, about 15 $mW\ mm^{-2}$, about 16 $mW\ mm^{-2}$, about 17 $mW\ mm^{-2}$, about 18 $mW\ mm^{-2}$, about 19 $mW\ mm^{-2}$, about 20 $mW\ mm^{-2}$, about 21 $mW\ mm^{-2}$, about 22 $mW\ mm^{-2}$, about 23 $mW\ mm^{-2}$, about 24 $mW\ mm^{-2}$, or about 25 $mW\ mm^{-2}$, inclusive, including any values between these numbers.

In some embodiments, the light-activated stabilized step function opsin proteins of the methods described herein can maintain a sustained photocurrent for about 10 minutes or longer. In other embodiments, the light-activated stabilized step function opsin proteins described herein can maintain a sustained photocurrent for any of about 10, 11, 12, 13, 14, 15, 16, 17, 18, 19, 20, 21, 22, 23, 24, 25, 26 27, 28, 29, or 30 minutes, inclusive, including for any times in between these numbers. In other embodiments, the methods provided herein comprise completely blocking the photocycle progression of any of the light-activated stabilized step function opsin proteins described herein after the protein is illuminated with a single pulse of light having a first wavelength.

In some aspects of the methods described herein, the animal cell can be a neuronal cell, a cardiac cell, or a stem cell. In some embodiments, the animal cell can be a neuronal cell. In other embodiments, the neuronal cell can be an excitatory neuron located in the pre-frontal cortex of a non-human animal. In other embodiments, the excitatory neuron can be a pyramidal neuron. In other embodiments, the animal cells comprise neurons that effect social behavior when depolarized. In some embodiments, the neuronal cell is a neuron that changes innate social behavior and/or conditioned behavior when depolarized. In other embodiments, the animal cells comprise neurons that give rise to the social and cognitive defects in autism and/or schizophrenia when depolarized. In some embodiments the neuronal cell can be an inhibitory neuron located in the pre-frontal cortex of a non-human animal. In still other embodiments, the inhibitory neuron can be a parvalbumin neuron. In some embodiments, the inhibitory and excitatory neurons can be in a living non-human animal. In other embodiments, the inhibitory and excitatory neurons can be in a brain slice from a non-human animal.

Methods for Identifying a Chemical Compound that Inhibits the Depolarization of Excitatory or Inhibitory Neurons in the Prefrontal Cortex Provided herein is a method for identifying a chemical compound that inhibits the depolarization of excitatory or inhibitory neurons in the prefrontal cortex of a non-human animal, the method comprising: (a) depolarizing an excitatory or inhibitory neuron in the prefrontal cortex of a non-human animal or a living tissue slice from a non-human animal comprising a light-activated protein cation channel expressed on the cell membrane capable of mediating a depolarizing current in the cell when the cell is illuminated with light, wherein the protein exhibits rapid step-like activation in response to a single pulse of light having a first wavelength and deactivation in response to a pulse of light having a second wavelength; wherein the depolarizing current in the cell is maintained for up to about twenty minutes; and wherein the protein comprises the amino acid sequence of ChR2, ChR1, VChR1, or VChR2 with amino acid substitutions at amino acid residues corresponding to C128 and D156 of the amino acid sequence of ChR2; (b) measuring an excitatory post synaptic potential (EPSP) or an inhibitory post synaptic current (IPSC) in response to selectively depolarizing the excitatory or inhibitory neuron comprising the light-activated protein; (c) contacting the excitatory neuron with a chemical compound; and (d) measuring the excitatory post synaptic potential (EPSP) or an inhibitory post synaptic current (IPSC) to determine if contacting the excitatory neuron with the chemical compound inhibits the depolarization of the neuron. In some embodiments, the proteins can be activated with light having a first wavelength that can be blue light. In other embodiments, said light having a first wavelength can be about 445 nm. In other embodiments, said light having a second wavelength can be green light or yellow light. In other embodiments, said light having a second wavelength can be about 590 nm. In still other embodiments, said light having a second wavelength can be between about 390-400 nm, inclusive, as well as every number within this range. In some embodiments, the chemical compound can be a member of a combinatorial chemical library.

In some aspects of the methods provided herein, the light-activated stabilized step function opsin proteins can be activated by light pulses that can have a duration for any of about 1 millisecond (ms), about 2 ms, about 3, ms, about 4, ms, about 5 ms, about 6 ms, about 7 ms, about 8 ms, about 9 ms, about 10 ms, about 15 ms, about 20 ms, about 25 ms, about 30 ms, about 35 ms, about 40 ms, about 45 ms, about 50 ms, about 60 ms, about 70 ms, about 80 ms, about 90 ms, about 100 ms, about 200 ms, about 300 ms, about 400 ms, about 500 ms, about 600 ms, about 700 ms, about 800 ms, about 900 ms, about 1 see, about 1.25 see, about 1.5 see, or about 2 see, inclusive, including any times in between these numbers. In some embodiments of the methods provided herein, the light-activated stabilized step function opsin proteins can be activated by light pulses that can have a light power density of any of about 1 µW mm$^{-2}$, about 2 µW mm$^{-2}$, about 3 µW mm$^{-2}$, about 4 µW mm$^{-2}$, about 5 µW mm$^{-2}$, about 6 µW mm$^{-2}$, about 7 µW mm$^{-2}$, about 8 µW mm$^{-2}$, about 9 µW mm$^{-2}$, about 10 µW mm$^{-2}$, about 11 µW mm$^{-2}$, about 12 µW mm$^{-2}$, about 13 µW mm$^{-2}$, about 14 µW mm$^{-2}$, about 15 µW mm$^{-2}$, about 16 µW mm$^{-2}$, about 17 µW mm$^{-2}$, about 18 µW mm$^{-2}$, about 19 µW mm$^{-2}$, or about 20 µW mm$^{-2}$, inclusive, including any values between these numbers. In other embodiments, the light-activated stabilized step function opsin proteins can be activated by light pulses that can have a light power density of any of about 1 mW mm$^{-2}$, about 2 mW mm$^{-2}$, about 3 mW mm$^{-2}$, about 4 mW mm$^{-2}$, about 5 mW mm$^{-2}$, about 6 mW mm$^{-2}$, about 7 mW mm$^{-2}$, about 8 mW mm$^{-2}$, about 9 mW mm$^{-2}$, about 10 mW mm$^{-2}$, about 11 mW mm$^{-2}$, about 12 mW mm$^{-2}$, about 13 mW mm$^{-2}$, about 14 mW mm$^{-2}$, about 15 mW mm$^{-2}$, about 16 mW mm$^{-2}$, about 17 mW mm$^2$, about 18 mW mm$^2$, about 19 mW mm$^2$, about 20 mW mm$^2$, about 21 mW mm$^2$, about 22 mW mm$^2$, about 23 mW mm$^{-2}$, about mW mm$^{-2}$, or about 25 mW mm$^{-2}$, inclusive, including any values between these numbers.

In some aspects of the methods described herein, the animal cell can be a neuronal cell, a cardiac cell, or a stem cell. In some embodiments, the animal cell can be a neuronal cell. In other embodiments, the neuronal cell can be an excitatory neuron located in the pre-frontal cortex of a non-human animal. In other embodiments, the excitatory neuron can be a pyramidal neuron. In some embodiments the neuronal cell can be an inhibitory neuron located in the pre-frontal cortex of a non-human animal. In still other embodiments, the inhibitory neuron can be a parvalbumin neuron. In some embodiments, the inhibitory and excitatory neurons can be in a living non-human animal. In other embodiments, the inhibitory and excitatory neurons can be in a brain slice from a non-human animal. In other embodiments, the brain slices comprise neurons that effect social behavior when depolarized. In some embodiments, the neuronal cell is a neuron that changes innate social behavior and/or conditioned behavior when depolarized.

In other embodiments, the brain slices comprise neurons that give rise to the social and cognitive defects in autism and/or schizophrenia when depolarized.

Methods for Identifying a Chemical Compound that Restores an Innate Social Behavior and/or Communication in a Non-Human Animal Provided herein are method for identifying a chemical compound that restores one or more social behaviors, communications, and/or conditioned behaviors in the non-human animal, the method comprising: (a) depolarizing an excitatory neuron in the prefrontal cortex of a non-human animal comprising a light-activated protein cation channel expressed on the cell membrane capable of mediating a depolarizing current in the cell when the cell is illuminated with light, wherein the protein exhibits rapid step-like activation in response to a single pulse of light having a first wavelength and deactivation in response to a pulse of light having a second wavelength; wherein the depolarizing current in the cell is maintained for up to about twenty minutes; and wherein the protein comprises the amino acid sequence of ChR2, ChR1, VChR1, or VChR2 with amino acid substitutions at amino acid residues corresponding to C128 and D156 of the amino acid sequence of ChR2, wherein depolarizing the excitatory neuron inhibits one or more one or more social behaviors, communications, and/or conditioned behaviors in the non-human animal; (b) administering a chemical compound to the non-human animal; and (c) determining if the administration of the chemical compound to the non-human animal restores said one or more social behaviors, communications, and/or conditioned behaviors in the non-human animal. In some aspects, the social behavior is an innate social behavior and is selected from the group consisting of: allogrooming, resident-intruder aggression, isolation-induced fighting, sexual behavior, parental behavior, social recognition, and auditory communication. Information pertaining to innate social behavioral tests for mice and other lab models can be found in Crawley, *Social Behavior Tests for Mice*, Laboratory of Behavioral Neuroscience, National Institute of Mental Health, (Bethesda, Md.; 2007), the disclosure of which is hereby incorporated herein by reference in its entirety. In other embodiments, the behavior is a conditioned behavior, such as, but not limited to, a conditioned fear response. In some embodiments, the non-human animal is not constrained by any hardware during steps (b) through (c). In some embodiments, the hardware is a light source attached to a fiber optic cable. In other embodiments, the non-human animal is separated from hardware immediately after the stabilized step function opsin protein is activated in response to said single pulse of light having a first wavelength. In some embodiments, the animal cell is located on the surface of a biological tissue. In some embodiments, the tissue is neural tissue or brain tissue. In some embodiments, the chemical compound can be a member of a combinatorial chemical library.

In some embodiments, the non-human animals of the methods provided herein comprise the protein corresponding to SEQ ID NO: 1. In other embodiments, the animals comprise the stabilized step function opsin proteins disclosed herein. In some embodiments, the animals comprising the stabilized step function opsin proteins disclosed herein are transgenically expressing said stabilized step function opsin proteins. In other embodiments, the animals comprising the stabilized step function opsin proteins described herein have been virally transfected with a vector carrying the stabilized step function opsin proteins such as, but not limited to, an adenoviral vector or an andeno-associated viral vector. In some embodiments, the animals comprising the stabilized step function opsin proteins disclosed herein exhibit changes in behavior when said stabilized step function opsin proteins are depolarized by activation with light. In other embodiments, the animals comprising the stabilized step function opsin proteins disclosed herein exhibit changes in innate and learned social behaviors when said stabilized step function opsin proteins are depolarized by activation with light. In other embodiments, the animals comprising the stabilized step function opsin proteins disclosed herein exhibit changes in conditioned behaviors when said stabilized step function opsin proteins are depolarized by activation with light.

EXEMPLARY EMBODIMENTS

The present disclosure is believed to be useful for optical control over nervous system disorders. Specific applications of the present invention relate to optogenetic systems or methods that correlate temporal, spatio, and/or cell-type control over a neural circuit with measurable metrics. As many aspects of the example embodiments disclosed herein relate to and significantly build on previous developments in this field, the following discussion summarizes such previous developments to provide a solid understanding of the foundation and underlying teachings from which implementation details and modifications might be drawn including those found in Yizhar et al., Nature, 2011, 477(7363):171-8, the disclosure of which in incorporated by reference herein in its entirety. It is in this context that the following discussion is provided and with the teachings in the references incorporated herein by reference. While the present invention is not necessarily limited to such applications, various aspects of the invention may be appreciated through a discussion of various examples using this context.

Various embodiments of the present disclosure relate to an optogenetic system or method that correlates temporal control over a neural circuit with measurable metrics. For instance, various metrics or symptoms might be associated with a neurological disorder exhibiting various symptoms of social dysfunction. The optogenetic system targets a neural circuit within a subject/patient for selective control thereof. The optogenetic system involves monitoring the subject/patient for the metrics or symptoms associated with the neurological disorder. In this manner, the optogenetic system can provide detailed information about the neural circuit, its function and/or the neurological disorder.

Figure 12:
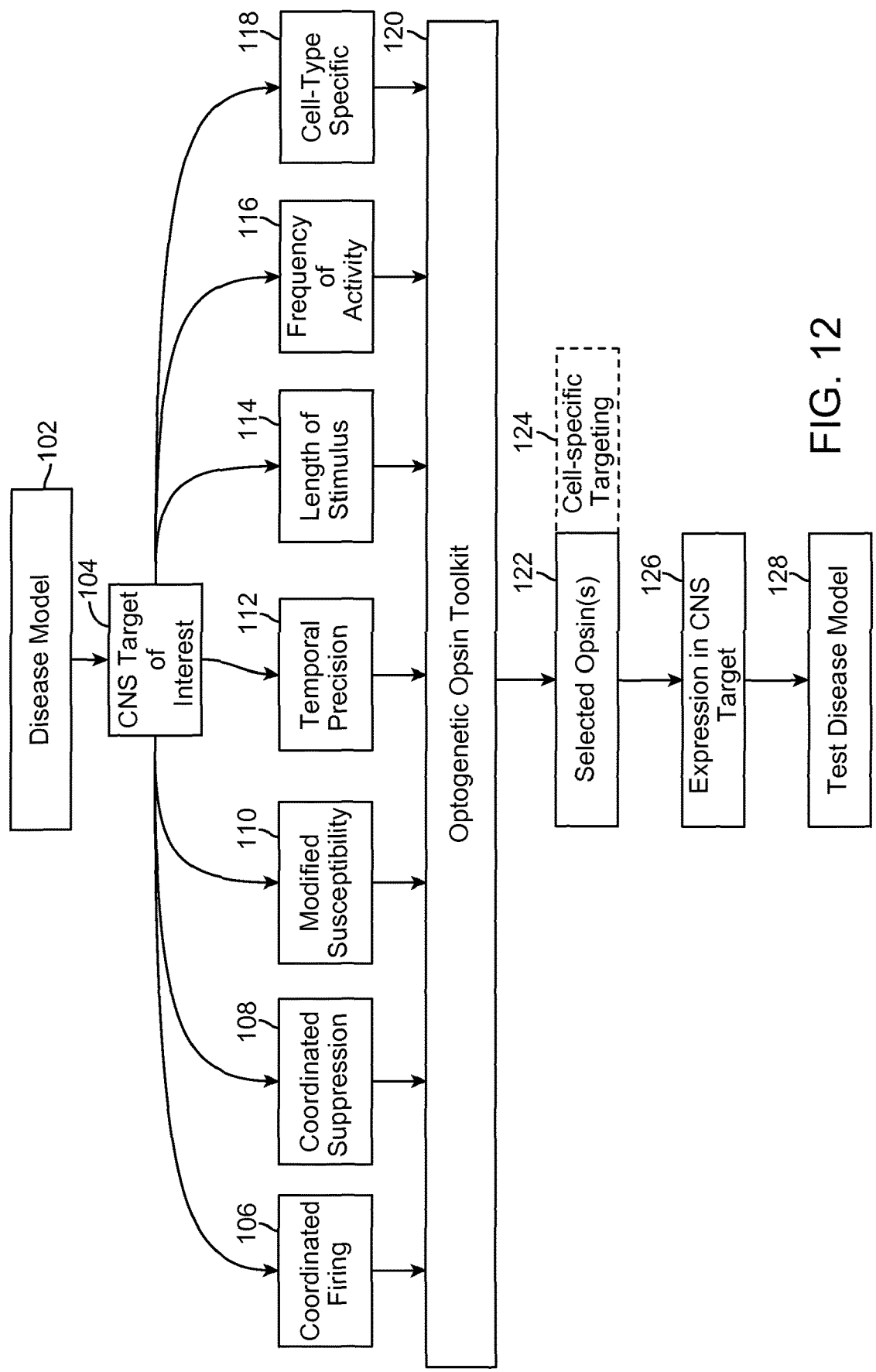
FIG. 12 depicts a flow diagram for testing of a disease model, consistent with various 10 embodiments of the present disclosure.

FIG. 12 depicts a flow diagram for testing of a disease model, consistent with various embodiments of the present disclosure. At 102, one or more disease models are identified or selected. The disease models can be for one or more central nervous system (CNS) disorders. The models can include various disorders, diseases or even general characteristics of patients (e.g., mood, memory, locomotion or social behavior). At 104, one or more CNS targets are identified. As used herein, the CNS targets include the properties of the stimulus to be provided as part of assessing, testing or otherwise related to the disease model. Non-limiting examples of targets can be spatial targets, cell type targets, temporal targets and combinations thereof.

The properties of the targets 106-118 can then be used to select a particular opsin from the optogenetic toolkit 120. The optogenetic toolkit 120 includes a variety of different opsins, which can be aligned with one or more of the properties 106-118. Various non-limiting examples of the opsins are discussed herein. The selected opsin(s) 122 can be those opsins that most closely match the CNS target(s) and/or stimulus properties. For example, a desired target may be the modification of excitation/inhibition (E/I) balance within a portion of the brain over an extended period of time. As discussed herein, the opsin C1V1 (discussed in more detail herein) and its variants could be selected. Thereafter, the selected opsin(s) are expressed in a target CNS location/cell-type 124. The disease module is then tested 126, e.g., through optical stimulus of the expressed opsin(s).

Embodiments of the present disclosure are directed toward control over the cellular excitation/inhibition (E/I) balance within neocortical microcircuitry. Such E/I balance control can be particularly useful for modeling and/or treatment of social and cognitive deficits (e.g., autism and schizophrenia) that are linked to elevations in excitation.

Embodiments of the present disclosure are directed toward the use of opsins for providing a mechanism for inducing an elevated cellular E/I balance with specific spatial and temporal control. This can include expression of light-sensitive opsins in excitatory neurons linked with one or more severe neuropsychiatric diseases.

Various embodiments relate to tools and methods for controlling the E/I balance in freely moving mammals, which can be particularly useful for exploring underlying circuit physiology mechanisms. Particular aspects of the present disclosure relate to increasing the excitability of excitatory neurons, relative to the excitability of inhibitory neurons with selective spatial control. This can be particularly useful for increasing the susceptibility of the excitatory neurons to intrinsic stimulus and thereby preserving natural firing patterns. In some implementations, this excitation is reversible.

Certain embodiments are directed toward the use of ion channels that are optically controllable. When expressed in a neuron, the ion channels are designed to increase the susceptibility of the neurons to intrinsic stimulus to maintain the increased susceptibility for extended periods of time. Embodiments of the present disclosure relate to SSFOs (stabilized step-function opsins) that are stable enough to produce constant photocurrent after a single light flash over many minutes, and the use thereof for complex behavioral testing. In particular implementations, the increased susceptibility can be maintained from many minutes after optical stimulus is applied.

Various embodiments are directed toward treatments, modeling and other aspects that relate to the discovery that impairments in specific social interaction and cognition behaviors in freely moving mice can be induced from targeted elevation in the E/I balance.

Other embodiments are directed towards treatments, modeling and other aspects that relate to the discovery that no such behavioral effects are seen when selectively providing the same excitability advantage to inhibitory neurons, irrespective of profound effects on local circuit activity.

Still other embodiments of the present disclosure are directed toward treatments, modeling and other aspects that relate to the discovery that the dominant circuit-level effect of the behaviorally significant E/I balance intervention is a specific elevation in baseline gamma-band (around 40-60 Hz) recurrent synaptic excitation, analogous to the elevated gamma rhythms seen at baseline in autism and schizophrenia, with concomitant quantitative impairment in microcircuit information transmission.

Embodiments of the present disclosure relate to the use of opsins to drive E/I elevations and monitor gamma oscillations in cortical slices. Particular embodiments are directed toward the use of C1V1 (discussed in more detail herein) and its variants, which can be particularly useful for driving E/I elevations and monitoring gamma oscillations in cortical slices, with 1) high potency to enable dose-response tests; 2) low desensitization to allow for step-like changes in E/I balance; and 3) red-shifted excitation to allow separable driving of different populations within the same preparation.

Embodiments of the present disclosure relate to control over elevated (or lowered) cellular E/I balance. This can be particularly useful for studying, testing and treatment relating to medication-unresponsive social and cognitive impairment in neurological disorders, such as autism and schizophrenia. Particular aspects relate to studying and distinguishing the long term effects on the development and maturation of the circuit relative to the immediate effects of E/I abnormalities with regard to the function of the neural circuits involved. Other aspects are directed toward the confirmation of elevated cellular E/I balance as a core component of cognitive defects observed in the various disease models and patients (human or otherwise). Particular embodiments provide timing and specificity sufficient for testing the elevated cellular E/I balance hypothesis in the mammalian brain (e.g., the prefrontal cortex), and identified circuit-physiology manifestations.

A particular aspect relates to the use of the double-mutant SSFO (discussed in more detail herein), which can be particularly useful for providing stable circuit modulation for time periods that are sufficient for temporally precise and complex behavioral experiments. For instance, the modulation and behavioral experiments circuit modulation can span several minutes in the absence of ongoing light activation, external fiber optic attachments and/or optical-hardware brain penetration (e.g., using a light delivery device entirely external to the brain). Particular implementations use a property of photon integration, which can facilitate activation of cells with low light intensity (e.g., in the low-gm/mm$^2$). This activation can occur with relatively deep penetration of light into brain tissue (e.g., 3 mm or more relative to the light source). SSFO activation in excitatory (but not inhibitory) neurons can be used to produce profound and reversible impairments in social and cognitive function. In certain implementations, the impairments can be produced with little, if any, motor abnormalities or altered fear/anxiety behaviors.

Embodiments of the present disclosure also relate to the use of SSFO for in vitro probing of changes in circuit properties. For instance, SSFO's can be used to elevate cellular E/I balance and to measure the transfer functions of pyramidal neurons. Experimental results suggest that such elevation saturates the transfer functions of pyramidal neurons at low excitatory post-synaptic current (EPSC) rates, impairing information transmission within cortical circuitry, in contrast to consequences of reduction in E/I balance.

These and other aspects can be particularly useful for addressing the symptomatic and treatment challenges in medication-unresponsive disorders like autism, e.g., relative to
elevations in E/I balance and situations in which the brain appears hyper-excitable and impaired in its ability to process information.

Consistent with an experimental embodiment, a comparison was performed between light-evoked activity in C1V1-E 162T-expressing (discussed in more detail herein) and non-expressing pyramidal cells (PYR cells). PYR cells expressing C1V1-E162T spiked in response to 2 ms 561 nm light pulses, while the same stimulation paradigm reliably evoked excitatory postsynaptic potentials (EPSPs) in non-expressing cells within the same slices.

Particular embodiments of the present disclosure are directed toward the use of SSFO gene product to selectively favor excitation of one neural population over another. The selective favoring of the targeted population can be configured to prevent the SSFOs from overriding intrinsic excitation inputs to the targeted population. In this manner, the targeted population would not be driven with coordinated spikes directly caused by the opsins. Rather, the targeted population would exhibit an increased sensitivity to native inputs, which can be sparse and asynchronous.

Embodiments of the present disclosure are directed toward the use of SFOs to address various the hardware challenges. For instance, the significant increase in light sensitivity (e.g., orders-of-magnitude greater) can facilitate the use alternative light delivery mechanisms, and hardware-free behavioral testing.

Aspects of certain embodiments of the present disclosure are directed toward identification and modification of specific portions of light-gated channels. These modifications involve identifying key portions of the channels. The channels can be identified using high resolution imaging of the tertiary structure of the channel. Alternatively, knowledge of the structure of similar channels can be used. The following description provides details of a specific experimental implementation and methodology. The present disclosure is not limited to any one implementation and can be implemented for a number of different molecular modifications at various locations consistent with the teachings herein.

Specific aspects of the present disclosure relate to microbial opsin genes adapted for neuroscience, allowing transduction of light pulse trains into millisecond-timescale membrane potential changes in specific cell types within the intact mammalian brain (e.g., channelrhodopsin (ChR2), Volvox channelrhodopsin (VChR1), and halorhodopsin (NpHR)). ChR2 is a rhodopsin derived from the unicellular green algae *Chlamydomonas reinhardtii*. The term "rhodopsin" as used herein is a protein that comprises at least two building blocks, an opsin protein, and a covalently bound cofactor, usually retinal (retinaldehyde). The rhodopsin ChR2 is derived from the opsin Channelopsin-2 (Chop2), originally named Chlamyopsin-4 (Cop4) in the *Chlamydomonas* genome. The temporal properties of one depolarizing channelrhodopsin, ChR2, include fast kinetics of activation and deactivation, affording generation of precisely timed action potential trains. For applications seeking long timescale activation, it has been discovered that the normally fast off-kinetics of the channelrhodopsins is slowed. For example, certain implementations of channelrhodopsins apply 1 mW/mm$^2$ light for virtually the entire time in which depolarization is desired, which can be less than desirable.

Much of the discussion herein is directed to ChR2. Unless otherwise stated, the disclosure includes a number of similar variants. Examples include, but are not limited to, Chop2, ChR2-310, Chop2-310, and Volvox channelrhodopsin (VChR1). For further details on VChR1, reference can be made to "Red-shifted optogenetic excitation: a tool for fast neural control derived from *Volvox carteri*," Nat Neurosci., June 2008, 11(6):631-3. Epub 2008 Apr. 23, which is fully incorporated herein by reference. In other implementations similar modifications can be made to other opsin molecules. For instance, modifications/mutations can be made to ChR2 or VChR1 variants. Moreover the modified variants can be used in combination with light-activated ion pumps.

Embodiments of the present disclosure include relatively minor amino acid variants of the naturally occurring sequences. In one instance, the variants are greater than about 75% homologous to the protein sequence of the naturally occurring sequences. In other variants, the homology is greater than about 80%. Yet other variants have homology greater than about 85%, greater than 90%, or even as high as about 93% to about 95% or about 98%. Homology in this context means sequence similarity or identity, with identity being preferred. This homology can be determined using standard techniques known in the sequence analysis. The compositions of embodiments of the present disclosure include the protein and nucleic acid sequences provided herein, including variants which are more than about 50% homologous to the provided sequence, more than about 55% homologous to the provided sequence, more than about 60% homologous to the provided sequence, more than about 65% homologous to the provided sequence, more than about 70% homologous to the provided sequence, more than about 75% homologous to the provided sequence, more than about 80% homologous to the provided sequence, more than about 85% homologous to the provided sequence, more than about 90% homologous to the provided sequence, or more than about 95% homologous to the provided sequence.

As used herein, stimulation of a target cell is generally used to describe modification of properties of the cell. For instance, the stimulus of a target cell may result in a change in the properties of the cell membrane that can lead to the depolarization or polarization of the target cell. In a particular instance, the target cell is a neuron and the stimulus affects the transmission of impulses by facilitating or inhibiting the generation of impulses (action potentials) by the neuron.

For further details on light-responsive opsins, reference can be made to PCT publication No. WO 2010/056970, entitled "Optically-Based Stimulation of Target Cells and Modifications Thereto," to Deisseroth et al., which is fully incorporated herein by reference.

Embodiments of the present disclosure are directed towards implementation of bistable changes in excitability of targeted populations. This includes, but is not necessarily limited to, the double-mutant ChR2-C128S/D156A. This double-mutant ChR2-C128S/D156A has been found to be well-tolerated in cultured hippocampal neurons and preserved the essential SFO properties of rapid step-like activation with single brief pulses of blue light, and deactivation with green or yellow light. In particular, the activation spectrum of ChR2-C128S/D156A peaks at 445 nm. A second deactivation peak was found at 390-400 nm, with faster but less complete deactivation by comparison with the 590 nm deactivation peak. Peak photocurrents in cells expressing ChR2-C128S/D156A were found to be robust, and comparable to those of ChR2-D156A (231.08±31.19 s.e.m; n=9 cells and 320.96±78.26 s.e.m; n=7 cells, respectively). Other embodiments are directed toward a similar mutation in VChR1. For instance, the mutation in VChR1 could be provided at C123S/D151A, to provide a red-shifted photocurrent with slow kinetics comparable to ChR2.

Individual transfected and patch-clamped neurons were next activated with 100 ms pulses of 470 nm light, and to ensure over very long recordings that current decay would not be attributable to cell rundown, each cell was deactivated with prolonged 590 nm light pulses at distinct intervals to determine the magnitude of remaining SFO current at each time point. Surprisingly, neurons expressing ChR2-C128S/D156A gave rise to sustained photocurrents that were more stable than those from cells expressing either single mutant alone. Fitting a mono-exponential decay curve to the ratio of Ideactivation/Iactivation over time revealed a spontaneous decay time constant of 29.3 min for ChR2-C128S/D156A, indicating that the C128 and D156 mutations act synergistically to delay the decay of the open state of ChR2.

Consistent with the required improvement for the anticipated application to complex mammalian behaviors, significant portions of the double-mutant SFO current were still present up to 20 minutes after the single photoactivation pulse. Based on these surprisingly slow decay kinetics, the double-mutant gene is referred to as SSFO (for stabilized step-function opsin) gene. SSFO is also used as shorthand for the active protein. Both residues likely are involved in ChR2 channel closure (gating), and both mutations likely stabilize the open state configuration of the channel.

Without being limited by theory, aspects of the present disclosure relate to the discovery that SSFO may be completely blocked in photocycle progression, and may therefore represent the maximal stability possible with photocycle engineering. For instance, in contrast to ChR2-C128X and ChR2-D156A, the SSFO photocycle does not appear to access additional inactive deprotonated side products which likely split off the photocycle at later photocycle stages not reached in this mutant, in turn making the SSFO even more reliable for repeated use in vivo than the parental single mutations.

Embodiments of the present disclosure are directed toward the sensitivity of the SSFO to light. For instance, channelrhodopsins with slow decay constants effectively act as photon integrators. This can be particularly useful for more-sensitive, less-invasive approaches to optogenetic circuit modulation, still with readily titratable action on the target neuronal population via modulation of light pulse length. It has been discovered that, even at extraordinarily low light intensities (as low as 8 $\mu W/mm^{-2}$), hundreds of picoamps of whole-cell photocurrents could be obtained from neurons expressing SSFO, which increased with monoexponential kinetics in response to 470 nm light during the entire time of illumination. Other aspects relate to the use of activation time constants that are linearly correlated with the activation light power on a log-log scale, which is indicative of a power-law relationship and suggesting that the SSFO is a pure integrator, with total photon exposure over time as the only determinant of photocurrent. For instance, it is believed that the number of photons per membrane area required for photocurrents to reach a given sub-maximal activation (time to T) is constant regardless of activation light power.

Example embodiments of the present disclosure relate to the use of a hybrid ChR1/VChR1 chimera that contains no ChR2 sequence at all, is derived from two opsins genes that do not express well individually, and is herein referred to as C1V1. Embodiments of the present disclosure also relate to improvements of the membrane targeting of VChR1 through the addition of a membrane trafficking signal derived from the $Ki_r2.1$ channel. Confocal images from cultured neurons expressing VChR1-EYFP revealed a large proportion of intracellular protein compared with ChR2; therefore, membrane trafficking signal derived from the $Ki_r2.1$ channel was used to improve the membrane targeting of VChR1. Membrane targeting of this VChR1-ts-EYFP was slightly enhanced compared with VChR1-EYFP; however, mean photocurrents recorded from cultured hippocampal neurons expressing VChR1ts-EYFP were only slightly larger than those of VChR1-EYFP.

Accordingly, embodiments of the present disclosure relate VChR1 modified by exchanging helices with corresponding helices from other ChR5. For example, robust improvement has been discovered in two chimeras where helices 1 and 2 were replaced with the homologous segments from ChR1. It was discovered that whether splice sites were in the intracellular loop between helices 2 and 3 (at ChR1 residue Ala145) or within helix 3 (at ChR1 residue Trp163), the resulting chimeras were both robustly expressed and showed similarly enhanced photocurrent and spectral properties. This result was unexpected as ChR1 is only weakly expressed and poorly integrated into membranes of most mammalian host cells. The resulting hybrid ChR11VChR1 chimera is herein referred to as C1V1.

Aspects of the present disclosure relate to the expression of C1V1 in cultured hippocampal neurons. Experimental tests have shown a number of surprising and useful results, which are discussed in more detail hereafter. C1V1-EYFP exhibits surprisingly improved average fluorescence compared with VChR1-EYFP. Whole cell photocurrents in neurons expressing C1V1 were much larger than those of VChR1-EYFP and VChR1-ts-EYFP, and ionic selectivity was similar to that of ChR2 and VChR1. The addition of the Kir2.1 trafficking signal between C1V1 and YFP further enhanced photocurrents by an additional 41% (C1V1-ts-EYFP mean photocurrents were extremely large, nearly tenfold greater than wild type (WT) VChR1). Mean fluorescence levels closely matched the measured photocurrents (mean fluorescence 9.3±1, 19.6±3.4, 19.8±2.8 and 36.3±3.8 for VChR1-EYFP, VChR1-ts-EYFP, C1V1-EYFP and C1V1-ts-EYFP, respectively), suggesting that the increase in photocurrent sizes resulted mainly from the improved expression of these channels in mammalian neurons. Total somatic fluorescence (measured as integrated pixel density) was linearly correlated with photocurrent size in individual recorded/imaged cells across the different constructs (VChR1, VChR1-ts-EYFP, C1V1, C1V1-ts-EYFP). This suggests (without being limited by theory) that the increased photocurrent of C1V1 results from functional expression changes in neurons.

Various embodiments of the present disclosure relate to opsins with fast decay constants. This property can be particularly useful for providing precise control over spiking, e.g., in order to interfere minimally with intrinsic conductance, trigger single spikes per light pulse and/or minimize plateau potentials during light pulse trains. Experimental results suggest that the light-evoked photocurrents recorded in C1V1-ts-EYFP decayed with a time constant similar to that of VChR1. Aspects of the present disclosure are therefore directed toward modifications in the chromophore region to improve photocycle kinetics, reduced inactivation and/or possible further red-shifted absorption.

One embodiment is directed toward a corresponding ChETA mutation E162T, which experiments suggest provides an accelerated photocycle (e.g., almost 3-fold); reference can be made to Gunaydin, et al., Ultrafast optogenetic control, Nat Neurosci, 2010, and which is fully incorporated herein by reference. Surprisingly, this mutation was shown to shift the action spectrum hypsochromic to 530 nm, whereas analogous mutations in ChR2 or other microbial rhodopsins have caused a red-shift. Another embodiment is directed toward a mutation of glutamate-122 to threonine (C1V1-E122T). Experimental tests showed that C1V1-E122T is inactivated only by 26% compared to 46% inactivation of ChR2; in addition, the spectrum was further red-shifted to 546 nm.

Another embodiment of the present disclosure is directed toward a double mutant of C1V1 including both E122T and E162T mutations. Experimental tests have shown that the inactivation of the current was even lower than in the E122T mutant and the photocycle was faster compared to E162T. This suggests that multiple useful properties of the individual mutations were conserved together in the double mutant.

Embodiments of the present disclosure include the expression of various light-responsive opsins in neurons. Experimental tests of C1V1 opsin genes in neurons were carried out by generating lentiviral vectors encoding C1V1-ts-EYFP and various point mutation combinations discussed herein. The opsins were then expressed in cultured hippocampal neurons and recorded whole-cell photocurrents under identical stimulation conditions (2 ms pulses, 542 nm light, 5.5 mW/mm$^2$). Photocurrents in cells expressing C1V1, C1V1-E162T and C1V1-E122T/E162T were all robust and trended larger than photocurrents of ChR2-H134R. The experiments also included a comparison of integrated somatic YFP fluorescence and photocurrents from cells expressing C1V1-E122T/E162T and from cells expressing ChR2-H134R. Surprisingly, C1V1-E122T/E162T cells showed stronger photocurrents than ChR2-H134R cells at equivalent fluorescence levels. This suggests that C1V1 could possess a higher unitary conductance compared with ChR2-H134R. The test results suggest that the kinetics of C1V1-E122T were slower than those of C1V1-E122T/E162T and that cells expressing C1V1-E122T responded more strongly to red light (630 nm) than cells expressing the double mutant. This can be particularly useful for generating optogenetic spiking in response to red-light.

Consistent with various embodiments of the present disclosure, inhibitory and/or excitatory neurons residing within the same microcircuit are be targeted with the introduction of various opsins. Experimental tests were performed by separately expressed C1V1-E122T/E162T and ChR2-H134R under the CaMKIIa promoter in cultured hippocampal neurons. Cells expressing C1V1-E 122T/E162T spiked in response to 2 ms green light pulses (560 nm) but not violet light pulses (405 nm). In contrast, cells expressing ChR2-H134R spiked in response to 2 ms 405 nm light pulses, but not in response to 2 ms 561 nm light pulses.

Various embodiments of the present disclosure relate to independent activation of two neuronal populations within living brain slices. Experimental tests were performed by CaMKIIa-C1V1-E122T/E 162Tts-eYFP and EFIa-DIO-ChR2-H134R-EYFP in mPFC of PV::Cre mice. In non-expressing PYR cells, 405 nm light pulses triggered robust and fast inhibitory postsynaptic currents due to direct activation of PV cells, while 561 nm light pulses triggered only the expected long-latency polysynaptic IPSCs arising from C1V1-expressing pyramidal cell drive of local inhibitory neurons.

Consistent with other embodiments of the present disclosure, excitation of independent cellular elements can be performed in vivo. Experimental tests were performed using optrode recordings. To examine the inhibitory effect of PV cell activity on pyramidal neuron spiking, an experimental protocol was used in which 5 Hz violet light pulses (to activate ChR2 in PV cells) preceded 5 Hz green light pulses (to activate C1V1 in excitatory pyramidal neurons) with varying inter-pulse intervals. The test results suggest that when violet and green light pulses were separated by 100 ms, responses to green light pulses were not affected by the violet pulses. However, as delays between violet and green pulses were reduced, green light-induced events became more readily inhibited until being effectively/completely abolished when light pulses were presented simultaneously.

As discussed herein, various embodiments of the present disclosure relate to an optogenetic system or method that correlates temporal, spatio and/or cell-type control over a neural circuit with measurable metrics. Consistent with the other embodiments discussed herein, particular embodiments relate to studying and probing disorders. A non-exhaustive list of example embodiments and experimental results consistent with such embodiments is provided in Yizhar et al., Nature, 2011, 477(7363):171-8, the disclosure of which in incorporated by reference herein in its entirety. The references listed therein may assist in providing general information regarding a variety of fields that may relate to one or more embodiments of the present disclosure, and further may provide specific information regarding the application of one or more such embodiments, to which one or more references as follows may be applicable. Accordingly, each of these references is fully incorporated herein by reference.

Various embodiments described above and shown in the figures may be implemented together and/or in other manners. One or more of the items depicted in the drawings/figures can also be implemented in a more separated or integrated manner, or removed and/or rendered as inoperable in certain cases, as is useful in accordance with particular applications. In view of the description herein, those skilled in the art will recognize that many changes may be made thereto without departing from the spirit and scope of the present disclosure.

The present disclosure is believed to be useful as it relates to control over nervous system disorders, such as disorders associated with social dysfunction, as described herein. Specific applications of the present invention relate to optogenetic systems or methods that correlate temporal, spatio and/or cell-type-specific control over a neural circuit with measurable metrics. As many aspects of the example embodiments disclosed herein relate to and significantly build on previous developments in this field, the following discussion summarizes such previous developments to provide a solid understanding of the foundation and underlying teachings from which implementation details and modifications might be drawn, including those found in the attached Appendix. It is in this context that the following discussion is provided and with the teachings in the references incorporated herein by reference. While the present invention is not necessarily limited to such applications, various aspects of the invention may be appreciated through a discussion of various examples using this context.

Figure 13:
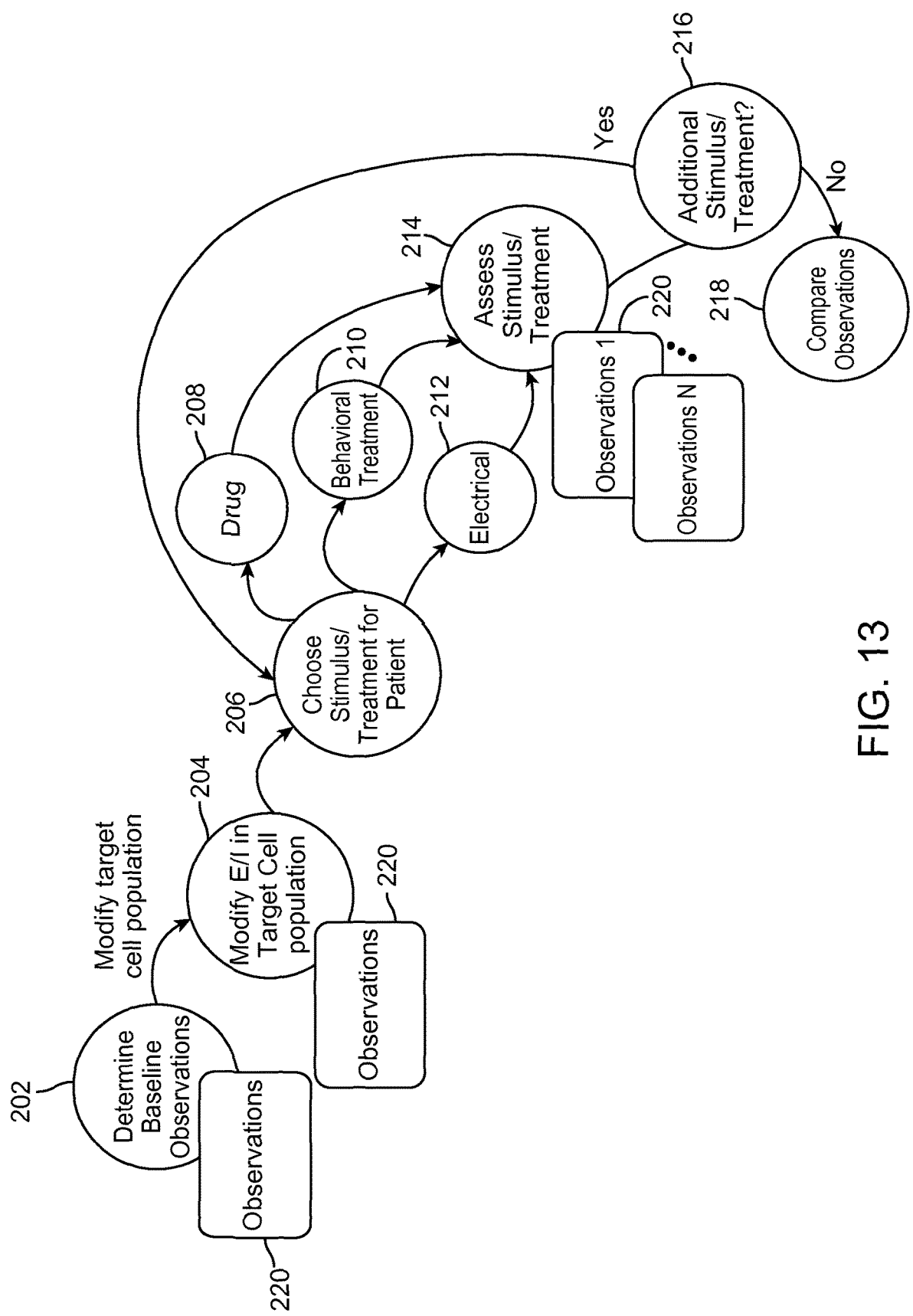
FIG. 13 depicts a model for assessing treatments of various nervous system disorders, consistent with an embodiment of the present disclosure.

FIG. 13 depicts a model for assessing stimuli and/or potential treatments for various nervous system disorders. Baseline observations 220 are taken 202 of behavior and/or cellular response for a subject/patient. A target cell population is chosen and modified to express a light-responsive molecule. In particular implementations, the target cell population is selected to provide control over the E/I balance in the prefrontal cortex of a subject's brain, as discussed in more detail herein. The excitation/inhibition (E/I) balance within the target cell population can then modified 204 (e.g., elevated or lowered) by exposing the modified target cell population to light. The light can be provided within a predetermined range based on absorption characteristics of the light-responsive molecule. Observations 220 of behavior and/or cellular response of the subject are again taken. These observations provide a reference point for how the subject acts under no stimuli or treatment.

To assess potential treatments, a stimulus and/or potential treatment is chosen 206 for the subject. Non-limiting examples of stimuli and treatments include pharmacological/drugs 208, behavioral 210 and/or electrical stimulus 212. The stimuli/treatments can then be assessed 214 by observing the subject's behavior in response to the treatment and/or the target cell population's behavior in response to the treatment. Based on the observations, a determination can be made regarding the need for additional stimulus or treatment 216, or the desire to test additional and/or different treatments. After the observations 220 have been collected, the observations 220 from various treatments can be compared 218 to each other as well as the baseline observation and the observations of behavior after E/I elevation. The comparison of the observations 220 can be used to assess the efficacy of various potential treatments.

In certain more specific embodiments, the elevation of the E/I balance results in social and cognitive deficits as compared to the behaviors during baseline observations. The purposeful and controlled elevation of the E/I balance allows for the testing of potential treatments in mammalian test subjects such as mice that do not otherwise exhibit symptoms of the disease being modeled.

Aspects of the present disclosure relate to assessing the effect of various stimuli on symptoms of neurological diseases. As discussed throughout this disclosure, modification of the E/I balance in the prefrontal cortex of a subject's brain results in the symptoms similar to those of various neurological disorders, such as autism and schizophrenia. In certain aspects of the present disclosure, the neural circuit identified as effecting E/I balance is manipulated using one or more techniques including pharmacological, electrical, magnetic, surgical and optogenetic methods. The effect of the manipulation of the symptoms displayed is monitored.

In certain more specific aspects, the manipulation of pyramidal neurons and parvalbumin-expressing inhibitory interneurons is used to model disease states, and to identify new treatments for known diseases. For example, the E/I balance in the prefrontal cortex is elevated (or lowered) and then a potential treatment is administered to the subject. The effect of the treatment on either the observed symptoms or on the neural circuit (or both) can be monitored. The information obtained from monitoring the symptoms and/or the neural circuit can be used to provide a better understanding of the neural pathways causing the observed symptoms. The information may also be used to determine the efficacy of the potential treatment. Based on the efficacy, or lack thereof, of the potential treatment, modifications can be made resulting in a new potential treatment to be tested.

In certain embodiments of the present disclosure, a stimulus is provided to a subject that exhibits symptoms of a neural disease such as schizophrenia or autism, for example. The stimulus can be pharmacological, electrical, magnetic, surgical, optogenetic or behavioral, for example.

Consistent with various embodiments of the present disclosure, control over the neural circuit can include inhibition or excitation, which can each include coordinated firing, and/or modified susceptibility to external circuit inputs. For instance, inhibition can be accomplished using a light-responsive opsin, such as an ion pump (e.g., NpHR and NpHR variants). Such ion pumps move the membrane potential of the neuron away from its threshold voltage to dissuade or inhibit action potentials. In another instance, excitation can be accomplished using a light-responsive opsin, such as an ion channel (e.g., ChR2 and ChR2 variants). Such ion channels can cause the membrane potential to move toward and/or past the threshold voltage, thereby exciting or encouraging action potentials. Consistent with various embodiments, a light-responsive opsin can be used to (temporarily) shift the resting potential of a neuron to increase or decrease its susceptibility to external circuit inputs. These various options can also be used in combination.

EXAMPLES

Example 1

Creation and Characterization of the Stabilized Step Function Opsin

Long-timescale (indeed bistable) optogenetic tools were initially developed that operate on timescales up to 4 orders of magnitude longer than that of wild type (wt) ChR2 (SFO or step function opsin gene products; -r-off=2.5-102 seconds); these mutations at the C128 position of ChR2 led to increased light sensitivity that scaled with the deactivation time constant. Subsequent work further developed the initial SFO concept, with mutation of the C128 proton networking partner D156 (FIG. 1A) for extension of the photocycle and lifetime of the open state. However, neither class of mutation gives rise to full stability on the mammalian-behavioral timescale-both showing substantial decay during the first 5-10 min- and extended illumination of SFO-expressing neurons in some cases can lead to channelrhodopsin inactivation caused by deprotonation of the chromophore and accumulation of a photocycle side product in a side reaction from a late photocycle intermediate. Therefore, the generation of a blue-light activated SFO suitably stable for combinatorial optogenetics in mammalian systems by mutating both C128 and D156 was attempted, hypothesizing that the combined mutant could potentially exhibit sufficient stabilization of the open state. Since the SFOs are activated with blue light but in fact can be deactivated with yellow light, if this additional property were maintained such a stable SFO would also deliver lateral-inhibition in the spectral domain that could further enhance combinatorial control.

Materials and Methods

ChR2(D156A) and SSFO were generated by introducing point mutations into the pLentiCaMKIIα-ChR2-EYFP-WPRE vector using site-directed mutagenesis (Quikchange II XL; Stratagene). The membrane trafficking signal was derived from the Kir2.1 channel. Mutations were confirmed by sequencing the coding sequence and splice sites. For AAV-mediated gene delivery, opsin-EYFP fusions along with the CaMKIIα promoter were subcloned into a modified version of the pAAV2-MCS vector. Cre dependent opsin expression was achieved by cloning the opsin-EYFP cassette in the reverse orientation between pairs of incompatible lox sites (loxP and lox2722) to generate a doublefloxed inverted open reading frame (D10) under the control of the elongation factor 1a (EF-1α) promoter. All constructs are available from the Deisseroth Lab (www.optogenetics.org).

For heterologous expression of ChRs in *Pichia pastoris* cells (strain 1168H, purchased from Invitrogen), human codon-optimized synthetic ChR-fragment encoding amino acids 1-315 (see accession no. AF461397) was cloned in the pPICZ vector (Invitrogen) via its EcoRI and NotI restriction sites. The C-terminal polyhistidine tag encoded on the vector was modified to a 12H is sequence. Mutants of ChR were generated by site-directed mutagenesis (QuickChange kit, Stratagene). Transformation, cell culture and protein purification were performed. After induction of protein expression for 24 h, cells were harvested and gently lysed using a high pressure homogenizer (Avastin). The membrane fraction was collected, homogenized and solubilized in 1% (w/v) dodecylmaltoside. After binding of ChR protein to a Ni-NTA resin (Qiagen) and washing of the column with 200 mM ChR imidazole, ChR was eluted with 500 mM imidazole. Fractions that contained the protein were pooled, desalted (Float-a-lyzer, Roth) and concentrated (Amicon Ultra, Millipore) to an optical density of 1 at 480 nm. Spectra were recorded in a Cary 50 Bio spectrophotometer (Varian Inc.).

Results

The ChR2 mutants C128S, D156A, and the double mutant 128S/156A were generated and purified from *Pichia pastoris* to first measure intrinsic open-state stability in the absence of potentially confounding cellular properties. Absorption spectra showed expected rapid changes in response to brief light delivery that largely recovered within 3 minutes for the single mutants C128S (FIG. 1B, F) and D156A (FIG. 1C, G). However, in contrast to both single mutants, the double mutant C128S/D156A showed remarkably complete stability of the activated state, with essentially no detectable return to the dark state even after 30 minutes (FIG. 1D, H). The characteristic two peaks of these absorption spectra can be ascribed to formation of the conducting state and a deprotonated species (P390; FIG. 1B, C) with some interesting differences among the variants. First, a reduced red shift of the conducting state relative to the dark state was noted for the double mutant compared with C128S (FIG. 1A, D), raising the concerning question of how effective the important property of inactivation with red-shifted light would be for the double mutant. On the potentially beneficial side, it was also noted that a reduced contribution from the nonconducting (P390) state relative to the conducting state existed in the double mutant compared with C128S (FIG. 1B, D), a useful property that may predict reduced accumulation of nonconducting channels and that suggests a late step of the photocycle that could deplete the conducting state (e.g. P520-* P480 desensitized state (Des480); FIG. 1E) may be almost completely blocked (FIG. 1E). The unique stability of the double mutant Cl 28S/D 156A is further illustrated by continuous monochromatic absorbance measurements of all three mutants over 35 minutes of recording (FIG. 1H).

Example 2

Validation of Activation in Neurons and In Vivo

The double mutant therefore appeared to have markedly distinct and near-optimal stability on the mammalian behavioral timescale, but with potentially reduced crucial capability for redshifted light deactivation; all of these issues required validation in neurons and in vivo.

Materials and Methods.

Whole Cell Patch-clamp Electrophysiology in Hippocampal and Cortical Neurons

Primary hippocampal cultures were isolated from P0 Sprague-Dawley rats, plated on Matrigel (Invitrogen)-coated glass coverslips and treated with FUDR to inhibit glia overgrowth. Endotoxin-free plasmid DNA was transfected in cultured neurons using a HEPES buffered Saline/CaPO$_4$ mix. Electrophysiological recordings from individual neurons identified by fluorescent protein expression were obtained in Tyrode media ([mM]150 NaCl, 4 KCl, 2 MgCl$_2$, 2 MgCl$_2$, 10 D-glucose, 10 HEPES, pH 7.35 with NaOH) using a standard internal solution ([mM] 130 KGluconate, 10 KCl, 10 HEPES, 10 EGTA, 2 MgCl$_2$, pH 7.3 with KOH) in 3-5 MΩ glass pipettes. For cortical slice physiology, acute 300 μm coronal slices from 8-9 week old wild-type C57BL/6J or PV::Cre mice previously injected with virus were obtained in ice-cold sucrose cutting solution ([mM] 11 D-glucose, 234 sucrose, 2.5 KCl, 1.25 NaH$_2$PO$_4$, 10 MgSO$_4$, 0.5 CaCl$_2$, 26 NaHCO$_3$) using a Vibratome (Leica). Slices were recovered in oxygenated Artificial Cerebrospinal Fluid (ACSF; [mM] 124 NaCl, 3 KCl, 1.3 MgCl$_2$, 2.4 CaCl$_2$, 1.25 NaH$_2$PO$_4$, 26 NaHCO$_3$, 10 D-glucose) at 32° C. for one hour. Individual neuron patches were obtained after identifying fluorescent protein expression from indicated prefrontal cortical layer under constant ACSF perfusion. Filtered light from a broad-wavelength xenon lamp source (Sutter Instruments DG-4) was coupled to the fluorescence port of the microscope (Leica DM-LFSA). Band pass filters (Semrock) had 20 nm bandwidth, and were adjusted with additional neutral density filters (ThorLabs) to equalize light power output across the spectrum. While handling cells or tissues expressing SSFO, care was taken to minimize light exposure to prevent activation by ambient light. Before each experiment, a 20 s pulse of 590 nm light was applied to convert all of the SSFO channels to the dark state and prevent run-down of photocurrents. For acquisition of SSFO activation and deactivation spectra, cultured neurons in voltage clamp mode were recorded. For recording activation spectra, a 1 s pulse of varying wavelength was applied, followed by a 10 s 590 nm pulse. Deactivation spectra were acquired by first applying a 1 s 470 nm pulse to activate SSFO, followed by a 10 s pulse of varying wavelength. Net activation or deactivation was calculated by dividing the photocurrent change after the first or second pulse, respectively, by the maximum photocurrent change induced by the peak wavelength for that cell. Negative values in deactivation spectra resulted from traces in which, for example, a 10 s 470 nm pulse led to a slight increase in photocurrent rather than deactivate the channels. This could be the result of the relatively wide (20 nm) band-pass filter width used for these recordings with the Sutter DG-4. Intermediate wavelengths (between 470 nm and 520 nm) are expected to have a mixed effect on the channel population for the same reasons.

Cultured cell images were acquired on the same microscope using a Retiga Exi CCD camera (Qimaging, Inc.) at 100 ms exposure with 30 gain. Illumination power density was 12 mW mm$^{-2}$ at 500 nm with a standard EYFP filter set. Quantification of fluorescence was performed with ImageJ software by marking a region containing the soma and proximal neurites and calculating for each cell the total integrated pixel intensity in that region, rather than average fluorescence, since photocurrents are likely to be related to the total number of membrane-bound channels rather than average channel expression per area. Photon flux calculations for SSFO integration properties were conducted by calculating the photon flux through the microscope objective at each light power, and then dividing to reach the photon flux across the cell surface, based on the diameter of the recorded cells and approximating cell shape as a spheroid.

Viral Gene Transfection

Both Lentiviral- and AAV-mediated gene delivery were used for heterologous expression of opsins in mice. Indicated opsins were driven by either Human calmodulin-dependent protein kinase II alpha (CaMKIIα) promoter to target cortical excitatory neurons or Elongation Factor 1a (EF-1a) in conjunction with a Cre-inducible cassette and followed by the Woodchuck hepatitis virus posttranscriptional regulatory element (WPRE). Cre-inducible recombinant AAV vector was produced by the University of North Carolina Vector Core (Chapel Hill, N.C., USA) and used in conjunction with parvalbumin::Cre transgenic mice to target parvalbumin positive interneurons. Briefly, SSFO-eYFP was inserted in the reverse orientation between pairs of incompatible lox sites (loxP and lox2722). AAV constructs were subcloned into a modified version of the pAAV2-MCS, serotyped with AAV5 coat proteins and packaged by the viral vector core at the University of North Carolina. The final viral concentration of AAV vectors was 1*10$^{12}$ genome copies (gc)/mL. Lentiviral constructs were generated as reported. All constructs are available from the Deisseroth Lab (www.optogenetics.org). Stereotactic viral injections were carried out under protocols approved by Stanford University. Juvenile (4-6 weeks) mice kept under isoflurane anesthesia were arranged in a stereotactic frame (Kopf Instruments) and leveled using bregma and lambda skull landmarks. Craniotomies were performed so as to cause minimal damage to cortical tissue. Infralimbic prefrontal cortex (IL; from bregma: 1.8 mm anterior, 0.35 mm lateral, −2.85 mm ventral) was targeted using a 1 OuL syringe and 35 g beveled needle (Word Precision Instruments). Virus was infused at a rate of 0.111 L/min. Subjects injected with virus for behavioral studies were additionally implanted with a chronic fiber optic coupling device to facilitate light delivery either with or without an attached penetrating cerebral fiber for local delivery to target cortical region as noted (Doric Lenses, Canada). Penetrating fibers were stereotactically inserted to a depth of −2.5 mm from the same anterior and lateral coordinates and affixed using adhesive luting cement (C&B MetaBond) prior to adhesive closure of the scalp (Vetbond, 3M). Animals were administered analgesic relief following recovery from surgery.

Results

As with wild-type ChR2, C128 mutants, and D156 mutants, it was found that the double-mutant ChR2-C128S/D156A expressed well in cultured hippocampal neurons and preserved the essential SFO properties of rapid step-like activation with single brief pulses of blue light, and deactivation with green or yellow light. Indeed, despite the reduced redshift in the double-mutant open-state absorbance, complete deactivation could be still achieved with redshifted light (in this case with yellow light, optimally at 590 nm), essential for potential combinatorial control purposes. Deactivation was also possible with 390 nm light, at a faster rate than yellow light due to the substantial presence of the P390 species, but was also incomplete due to the residual absorption of the dark state at this wavelength (FIG. 1A). Moreover, following deactivation with 390 nm light, reactivation with 470 nm was less effective than following 590 nm deactivation, pointing to a likely photochemical inactivation with UV light due to trapping in a deprotonated/desensitized isoform that is not reached after redshifted-light deactivation (illustrated in FIG. 1E), and again supporting the use of yellow light deactivation to potentially enhance spectral separation.

Peak photocurrents in cells expressing ChR2-C128S/D156A were comparable to those of ChR2-D156A (231.08±31.19; n=9 cells and 320.96+78.26; n=7 cells, respectively p=0.26, unpaired t-test). Consistent with the spectroscopic data, neurons expressing ChR2-C128S/D156A gave rise to sustained photocurrents that were far more stable than those from cells expressing either single mutant alone (FIG. 2B). Fitting a monoexponential decay curve to the ratio of deactivation/activation as a function of time revealed an apparent spontaneous decay time constant of 29.3 min for ChR2-C128S/D156A ($r^2$=0.9139) that was 4.2-fold longer than for D156A (6.9 min, $r^2$=0.8357; FIG. 2B) in side-by-side comparison. Indeed, given the fact that spectroscopy revealed essentially no reversion to the dark state on this timescale, remaining decay might be attributable in part to cell-dictated properties such as protein turnover. Consistent with the required improvement for the anticipated application to complex mammalian behaviors, FIG. 2C shows a typical long whole-cell recording with both blue light activation and yellow light deactivation in the setting of incoming asynchronous synaptic activity. Based on these surprisingly prolonged temporal properties, the double-mutant gene is referred to as SSFO (for stabilized step-function opsin) gene, and for simplicity use SSFO as shorthand for the protein as well.

Channelrhodopsins with such slow decay constants could enable the transduced cell to act as a photon integrator, with effective light sensitivity (i.e. photocurrent amplitude per photon absorbed by the cell) scaling with $T_{off}$. SSFO could therefore enable more-sensitive, less-invasive approaches to optogenetic circuit modulation, but still with temporally precise onset and offset of action and with readily titratable effects on the targeted neuronal population via modulation of light pulse length. Indeed, it was found that with extraordinarily low light intensities (as low as 8 µW mm$^{-2}$), hundreds of picoamps of whole-cell photocurrent could be obtained from neurons expressing SSFO (FIG. 2D). Photocurrents increased with monoexponential kinetics in response to 470 nm light during the entire time of illumination (FIG. 2D, left), and activation time constants were linearly dependent on activation light power on a log-log scale until the channel-intrinsic millisecond-scale was approached, suggesting that the SSFO achieves the status of a pure integrator, with total photon exposure over time as the only determinant of cellular photocurrent (FIG. 2D, middle; n=27 recordings from 5 cells). However, this also means that the opsin expressing tissue must be kept in complete darkness before experiments are initiated (trivial for mammalian in vivo experiments but requiring more attention for in vitro work). When data were represented as the total number of photons (delivered to a single neuronal soma and integrated over time) required for photocurrents to reach a fixed fraction of Imax for the recorded cell, this characteristic number of photons was constant regardless of activation light power FIG. 2D, right; $9.1 \times 10^8 \pm 1.6 \times 10^8$ photons; n=27 recordings from 5 cells), again demonstrating the pure photon integration property of the SSFO.

Figure 2:
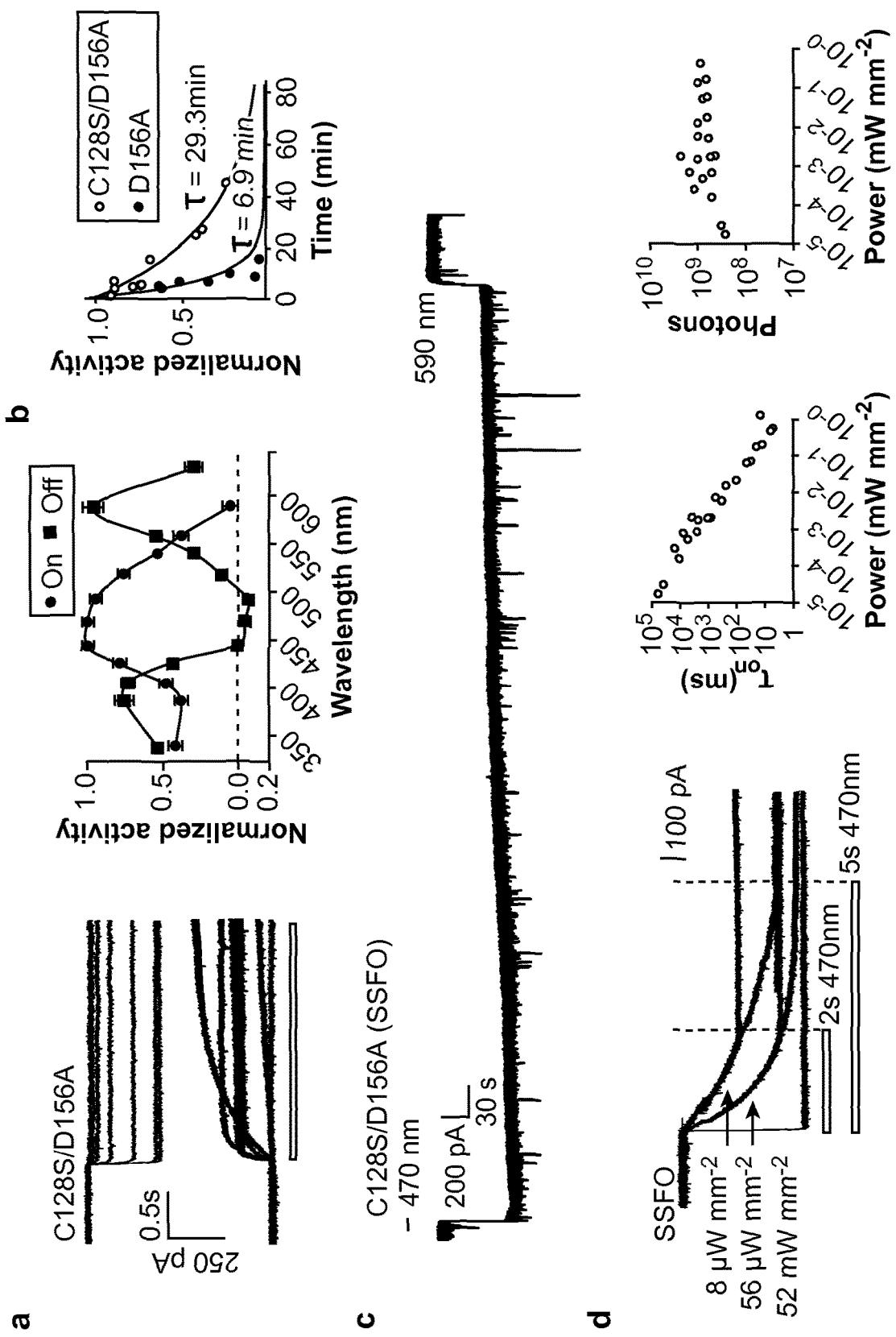
FIG. 2 depicts Stable step-modulation of neural activity in multiple cell types in vitro and in vivo. (a) Activation (top left) and deactivation (bottom left) spectra recorded from cultured neurons expressing ChR2 (C128S/D156A). Gray horizontal bars indicate light pulses and trace colors indicate wavelength of light used in each light pulse; summary spectra (right) for measurements of activation and deactivation of ChR2(C128S/D156A) are shown. (b) Monoexponential fits of photocurrent decay in cells expressing ChR2(C 128S/D 156A) (black; −t=29.3 min) or ChR2 (D156A) (gray; −t=6.9 min). (c) Representative whole-cell patch clamp recording of photocurrent in cultured hippocampal neuron expressing ChR2(C128S/D156A; "SSFO"). Bars indicate activation and deactivation light pulses; recording carried out in the naturalistic setting of incoming synaptic excitatory postsynaptic currents (epscs). (d) Whole-cell photocurrent responses of a cultured neuron expressing SSFO to 470 nm light pulses of indicated power (left). Pulse lengths were 2 s (gray horizontal bar traces) or 5 s (black horizontal bar traces). Dashed lines mark light pulse termination. Time constants for activation (T) are displayed on a log-log plot versus light power (n=27 recordings from 5 cells; middle). Regardless of light power, the calculated number of incident photons arriving at each cell for photocurrents to reach the exponential curve constant (63% of Imax) for that cell was constant (right). Each point represents a photon number from a single recording at a given light power (Methods). (e) Optrode recording configuration. 470 nm and 561 nm lasers were coupled to an optical fiber through a fiber coupler. A tungsten electrode was attached to the optical fiber with a 400 μm 1 lm projection past the fiber tip and advanced into the brain. (f) Activation of excitatory neurons using CaMKIIα-SSFO in anaesthetized animals stably elevates neuronal activity within the injected loci. Starred example trace is plotted below the instantaneous spike-rate heat maps calculated with 2 s moving average. Each heat-map line represents one sweep at indicated depth (3 sweeps at each site); 470 nm activation pulse and 561 nm deactivation pulses are indicated by blue and green bars, respectively. (g) Activation of PV-positive interneurons with PV::Cre/DIO-SSFO inhibits local network activity within the injected loci. Starred example trace is plotted below the instantaneous spike rate heat maps. (h) Average spike rates of traces showing significant differences in activity pre- and post-stimulation before activation, after activation, and after deactivation in CK-SSFO (squares) and PV::Cre/DIO-SSFO (circles) animals (n=2 mice, >5 recording sites per animal). (i) Representative 10-min long recording demonstrating sustained activity of SSFO. Instantaneous spike-rate heat maps are shown for activity of isolated single units indicated as Neuron 1 and Neuron 2; waveforms of indicated units are plotted next to corresponding traces.
Figure 2:
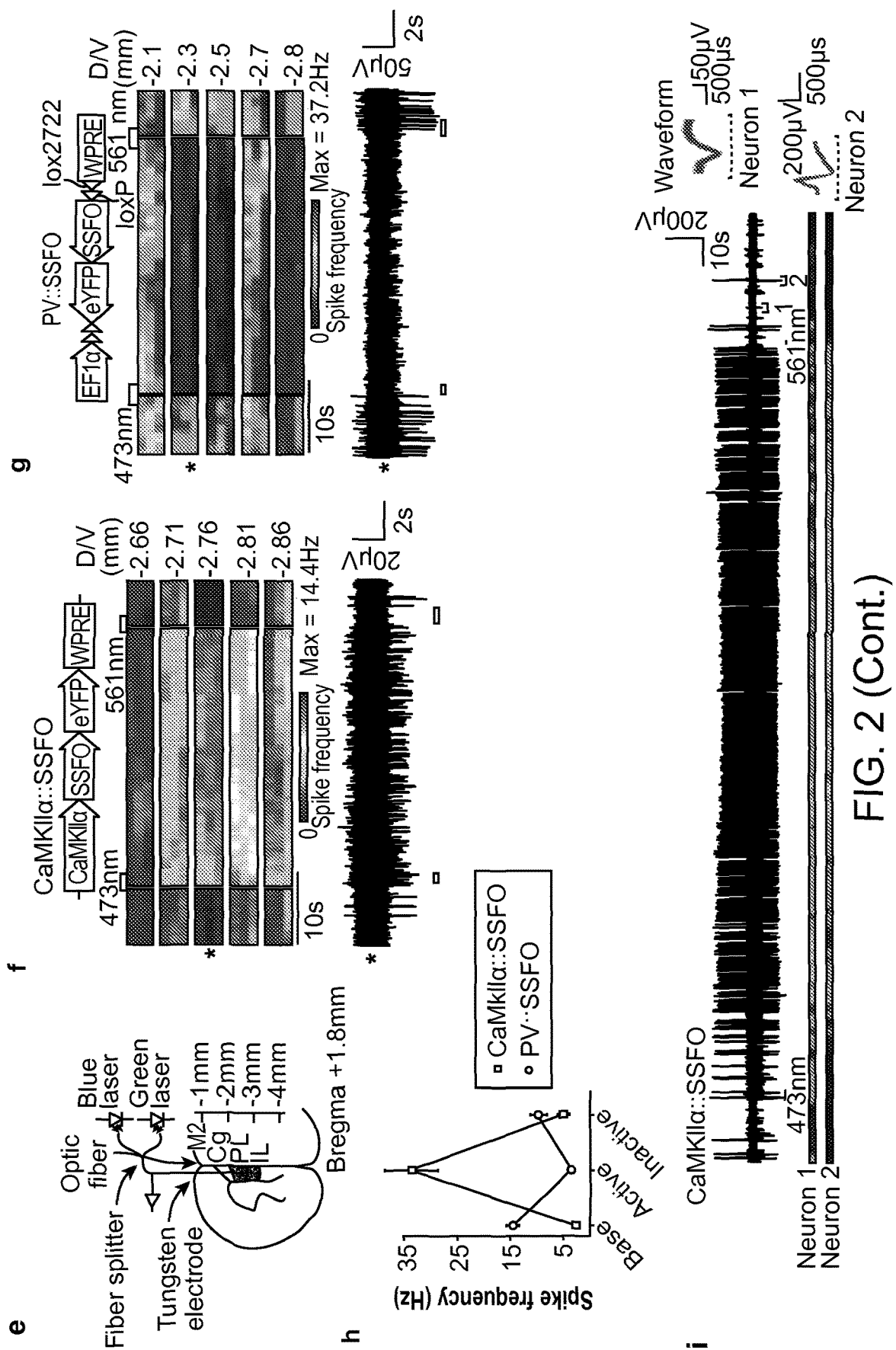

To validate this new optogenetic tool in vivo, the capability of the SSFO to achieve stable cell-type specific modulation in vivo in mammals was explored, using the regulation of cortical excitation and inhibition as an experimental system. As readout, optrode recordings in anesthetized mice expressing SSFO in the prelimbic (PL) and infralimbic (IL) subregions of the medial prefrontal cortex (mPFC; FIG. 2E) were performed. To modulate excitation, SSFO-eYFP in pyramidal neurons under the control of the excitatory neuron-specific CaMKIIa promoter was first expressed. Second, to modulate inhibition, SSFO-eYFP in PV::Cre transgenic mice was expressed using a double-floxed inverted open reading frame (DIO) virus; in these mice, SSFO was only expressed in the GABAergic Cre-positive parvalbumin neurons. To map optical modulation, recordings were made at progressively more ventral sites in mice injected with AAV5-CaMKIIα::SSFO-EYFP in medial prefrontal cortex (mPFC), using an advancing two-laser optrode (FIG. 2E) and a blue/green activation/deactivation laser protocol (FIG. 2F-G). Multiunit activity in mPFC of these mice was significantly and stably increased only in the transduced region, in response to a 1 s pulse of 473 nm light (95 mW mm$^{-2}$, corresponding to 10 mW mm$^{-2}$ at the electrode tip). This increased activity was effectively terminated with a 2 s 561 nm light pulse (112 mW mm$^{-2}$; FIG. 2F). Significant increases in multiunit spike rate (Hz) were restricted to mPFC (FIG. 2) and no significant reductions in spike rate were observed in any of the recording sites following blue light stimulation. In mPFC recording sites (but not in sites dorsal to mPFC) the average multiunit spike rates were light-modulated as expected; in traces that showed significant modulation of activity, before activation, after activation, and after deactivation spike rates were 2.60±0.39 Hz, 33.82±4.83 Hz and 5.04±1.23 Hz, respectively (FIG. 2H; n=46 recordings in 2 mice; p=3e-8 after activation and p=0.048 after deactivation, both compared with pre-activation baseline; Student's paired t-test).

Conversely, in PV::Cre mice injected with AAV5-EF1a-DIO-::SSFO-eYFP in mPFC, multiunit activity was decreased after an identical 1 s pulse of 470 nm light and returned to baseline levels following the 2 s 561 nm pulse (FIG. 2G). In these mice, decreases in multiunit spike rate were also highly restricted to mPFC (n=5 out of 54 recording sites along the full dorsoventral track) and no significant increase in spike rate was observed in any of the recording sites following blue light stimulation. In traces that showed significant modulation of activity, the average multiunit spike rates before activation, after activation, and after deactivation were 14.82±1.26 Hz, 3.66±0.58 Hz and 9.69±1.77 Hz, respectively (FIG. 2H; p=0.002 after activation and p=0.088 after deactivation, both compared with pre-activation baseline; Student's paired t-test). Again befitting the predicted high stability of the SSFO photocurrent, it was found that modulation of firing rates in vivo was stably sustained after the brief pulse for many minutes (FIG. 2I).

Example 3

Effects of SSFO on Behavior and Circuit Dynamics in Freely Moving Mice

Figure 3:
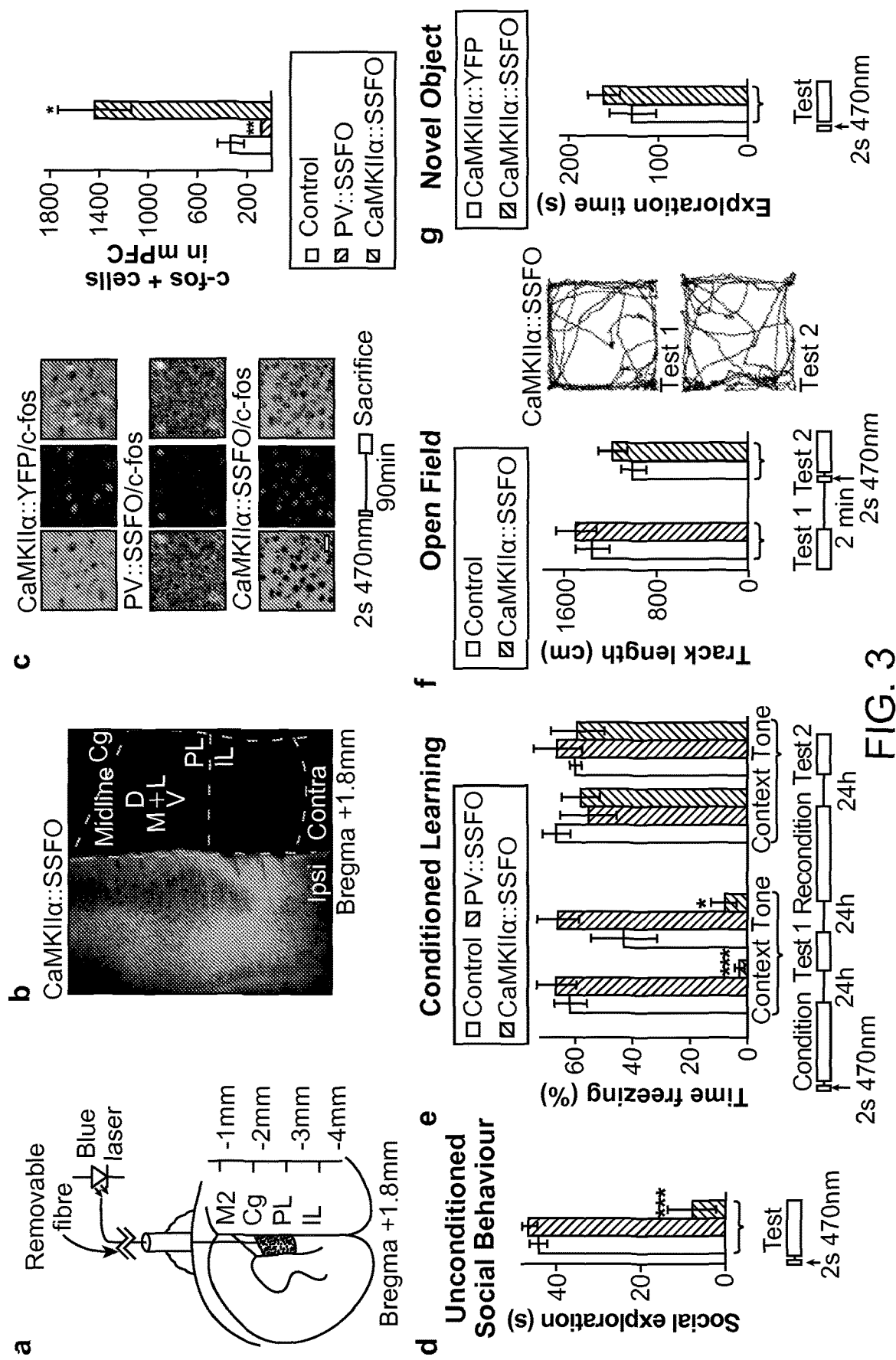
FIG. 3 depicts elevated, but not reduced, prefrontal E/I balance leads to behavioral impairment. (a) Wild-type or PV::Cre transgenic mice injected with control CaMKIIα-eYFP, CaMKIIα-SSFO, or DIO-SSFO virus in mPFC and chronically implanted with fiber optic connector were subjected to fear conditioning and social exploration tests. (b) Confocal image from a mouse injected with CaMKIIα-SSFO-eYFP virus shows expression in prelimbic (PL) and infralimbic (IL) cortex. (c) Representative images of prefrontal slices from PV::Cre/DIO-SSFO and CaMKIIα-SSFO mice stained for c-fos 90 min following a 2 s 470 nm light pulse; Bar=25 um. Graph shows average c-fos positive cell counts in mPFC of CaMKIIα-SSFO, and PV::Cre/DIO-SSFO animals. (d) Summary data for social exploration in control, CaMKIIα-SSFO, and PV::Cre/DIO-SSFO mice of a juvenile intruder in the home cage. CaMKIIα-SSFO mice showed a significant reduction in social exploration. (e) Mice administered one 2 s 470 nm pulse of light prior to fear conditioning were tested the next day for freezing in response to the conditioned context or to a conditioned auditory cue; CaMKIIα-SSFO mice were significantly impaired in freezing response to both conditioned stimuli. On the following day, mice were reconditioned without optical stimulation and freezing was evaluated 24 h later. All mice showed similar freezing behavior in the absence of light. (f) Open-field exploration is indistinguishable in CaMKIIα-SSFO (blue) and CaMKIIα-EYFP (gray) control mice, before (Test 1) and after (Test light activation. Example track from animal expressing CaMKIIα-SSFO for Test 1 (top) and Test two (bottom) are shown. (g) Exploration of a novel object over a 10-minute period is similar in mice expressing CaMKIIα-SSFO (black) and CaMKIIα-EYFP (gray). (h) Fluorescence images of coronal sections from wild-type mice injected with CaMKIIα-SSFO in PFC (top) or V1 (bottom). (i) Social behavior in the 3-chamber test is impaired following a 2 s 470 nm light pulse in mice expressing CaMKIIα-SSFO in PFC (n=6), but not in control mice (n=8) or mice expressing CaMKIIα-SSFO in V1 (n=8). All bar graphs depict mean±s.e.m. (* $p<0.05$,  $p<0.005$, * $p<0.0005$). (j) High magnification confocal images of a 40 μm coronal brain slice from a PV::Cre mouse bilaterally injected with Cre-dependent AAV5-EF1 a-DIO-SSFO-EYFP virus and stained with anti-parvalbumin antibody. Arrows indicate double-labeled PV neurons identified by membrane-bound EYFP labeling; arrowhead shows PV-positive neuron that did not express detectable levels of SSFO-EYFP. (k) Low-power confocal image of the same slice shown in (j), demonstrating spatially restricted expression of the DIO-SSFO virus in mPFC. (l) Percent double-labeled cells out of the entire PV+ cell population, and out of the entire YFP+ cell population as counted from high-magnification confocal z-stacks (n=7 slices from 4 mice; total of 617 PV+ cells counted, 191 YFP+ cells, 169 double-labeled cells). This number is consistent with ~40% PV neurons expressing Cre recombinase in this line and approximately 50% transduction efficiency of the virus. Since expression of PV is not uniform across cells, some PV+ neurons might express undetectable levels of PV but still contain sufficient levels of Cre for activating DIO-SSFO expression. (m) Quantification of c-fos immunofluorescence in cortical and subcortical regions from animals injected unilaterally with CaMKIIα::SSFO-EYFP virus (gray; n=2 mice) and controls injected unilaterally with CaMKIIα::EYFP virus (light gray; n=2 mice). Shown are data from the ipsilateral (injected) and contralateral (uninjected) hemispheres. Error bars indicate mean±s.e.m p=0.044). (n) Two representative traces showing open-field exploration in a control mouse expressing CaMKIIα::EYFP in mPFC, pre-activation and post-activation with a 2 s 473 nm light pulse. Neither locomotion velocity nor time spent exploring the center of the open field was altered in CaMKIIα::SSFO and CaMKII α::EYFP animals after a 2 s 473 nm light pulse (bottom; p>0.1, for both compared to pre-activation; paired t-test), indicating that SSFO activation is not anxiogenic.

Having established that SSFO can be used to bi-directionally modulate prefrontal excitability on behaviorally-relevant time scales SSFO was used to examine the effects of elevated cellular E/I balance on behavior and circuit dynamics in freely moving mice (FIG. 3). SSFO was expressed either in prefrontal cortical excitatory neurons using the excitatory neuron-specific CaMKIIα promoter, or in inhibitory parvalbumin (PV)-expressing neurons using a double-floxed, inverted open-reading-frame (DIO) virus in conjunction with PV::Cre transgenic mice (FIG. 3J-L). Virus was injected in mPFC as described above, followed by a chronic fiber-optic implant that projected past the skull immediately dorsal to mPFC for light delivery (FIG. 3A, B).

Materials and Methods
Mutual Information Calculations

To study the effects of SSFO on sEPSC-spike rate information, whole-cell patch recordings were conducted from visually identified pyramidal cells in layer V of mPFC. Using current clamp, a single pyramidal cell was stimulated with a train of simulated EPSC waveforms. Individual sEPSC events had peak current magnitudes of 200 pA and decayed with a time constant of 2 ms. Each experiment was divided into 10 sweeps, each 10 seconds long and separated by 5 seconds to minimize rundown. Each sweep was divided into 500 ms segments. The total number of sEPSCs in each 500 ms segment was randomly chosen from a uniform distribution between 0 and 250. Then, the times of the sEPSCs within the 500 ms segment were randomly selected from a uniform distribution extending across the entire segment, simulating excitatory input from a population of unsynchronized neurons. Empirically, these stimulation parameters reliably drove pyramidal neurons at firing rates from 0-30 Hz. In conditions marked as baseline, a 10 sec pulse of 590 nm light was delivered to completely inactivate the opsin before running the sEPSC protocol. In conditions where the opsin was activated, a 1 sec pulse of 470 nm light preceded the sEPSC protocol.

To understand the net effect of altered E/I balance on information processing, the mutual information between each neuron's input sEPSC rate and output spike rate was computed, which captures relevant changes in the shape of the IO curve and in the response variability. First, the joint distribution of sEPSC rate and spike rate was estimated by binning in time, sEPSC rate, and spike rate and building a joint histogram. Time bins were 125 ms wide, and sEPSC rate was divided into 10 equally spaced bins from 0 to 500 Hz, although the mutual information results were consistent across a wide range of binning parameters. Spike rate was binned using the smallest meaningful bin width given the time bin width (e.g. 8 Hz bin width for 125 ms time bins). From this joint histogram, mutual information was computed equaling the difference between response entropy and noise entropy. Response entropy quantifies the total amount of uncertainty in the output spike rate of the neuron. Noise entropy quantifies the uncertainty that remains in the output spike rate given the input rate. Note that the maximum information that neural responses can transmit about the input stimulus is the entropy of the stimulus set. For 10 equally spaced input sEPSC rate bins and a uniform distribution of input rate over these bins, the entropy of the input rate is $\log_2(10)=3.322$ bits. Mutual information calculated from undersampled probability distributions can be biased upwards. Consequently, all reported values of mutual information, response entropy and noise entropy were corrected for bias due to undersampling. This correction is done by computing values from smaller fractions (from one-half to one-eighth) of the full data and extrapolating to the limit of infinite data. Using 125 ms time windows, the correction factors were always less than 0.07 bits.

Also estimated was the input-output transfer function for each neuron by averaging the output spike rate across time bins with similar input sEPSC rates. The shape of the input-output function was quantified by computing the dynamic range and saturation point of each neuron, treating the baseline and opsin-activated conditions separately. Dynamic range was defined as the difference between maximal and minimal output spiking rate across the range of input sEPSC rates. Saturation point was defined as the lowest input sEPSC rate which drove the neuron at 90% of its maximal output spike rate within that condition. A reduced saturation point cannot result from a multiplicative reduction in gain or dynamic range, but instead indicates that the input-output function becomes flatter at higher input sEPSC rates.

Behavioral Testing

All animals undergoing behavioral experiments were acclimated to a 12-hour reverse light/dark cycle. Prior to behavioral testing, animals were allowed to acclimate to the room in which experiments were to be conducted for at least 1 hour before the experiments started.

The fear conditioning apparatus consisted of a square conditioning cage (18×18×30 cm) with a grid floor wired to a shock generator and a scrambler, surrounded by an acoustic chamber (Coulburn instruments, PA, USA). The apparatus was modified to enable light delivery during training and/or testing. To induce fear-conditioning mice were placed in the cage for 120 seconds, and then a pure tone (2.9 kHz) was played for 20 sec, followed by a 2 sec foot-shock (0.5 mA). This procedure was then repeated, and immediate freezing behavior was monitored for an additional 30 sec after the delivery of the second shock before the mice were returned to their home cage. Fear conditioning was assessed 24 hours later by a continuous measurement of freezing (complete immobility), the dominant behavioral fear response. To test contextual fear conditioning mice were placed in the original conditioning cage and freezing was measured for 5 min. To test auditory-cued fear conditioning mice were placed in a different context—a pyramid-shaped cage with a smooth floor. As a control for the influence of the novel environment, freezing was measured for 2.5 min in this new cage, and then a 2.9 kHz tone was played for 2.5 min, during which conditioned freezing was measured. Light stimulation through the fiberoptic connector was administered by delivering light through a custom patch-cord connected to a 473 nm laser. The light pulse was delivered for 2 seconds at a power of 98 mW mm$^{-2}$ at the fiber tip. The results of the contextual- and cued-conditioning tests were analyzed by a Student's t-test.

Social interaction in the home cage was analyzed. Briefly, a single mouse in the homecage was allowed to freely roam in the absence of the cage top for one minute. A novel juvenile (3-4 week old) male intruder was introduced to the opposite corner as the resident male subject and allowed to roam freely for two minutes. Total physical interaction between the two mice was quantified visually, scoring social interaction as the time during which the resident mouse actively explored the intruder. Stimulation trials were conducted with the addition of a two second pulse of 473 nm light delivered via a fiber optic cable (Doric Lenses) coupled to a chronically implanted fiber optic cable or chronically implanted non-invasive skull fiber coupling device as indicated. Fiber was decoupled prior to experimentation and one-minute acclimation period.

The three-chamber social test was conducted. The test mice were introduced into the center chamber of the three-chambered apparatus and allowed to acclimate for 10 minutes with the doors to the two side chambers closed. Light pulses were applied at the beginning and end of the 10 minute acclimation period. At the end of the acclimation period a novel conspecific male mouse was introduced to the "social" chamber, inside a wire mesh cup (Galaxy Pencil/ Utility cup, Spectrum Diversified Designs). In the other (non-social) chamber, an identical empty cup was placed. The designations of the social and non-social chambers were randomly chosen in each test to prevent chamber bias. Between tests, the chambers were cleaned with 20% ethanol and allowed to dry completely before initiating the next test. The time spent in the non-social, center, and social chambers was quantified using automated tracking software Viewer II (BiObserve, Fort Lee, N.J.). Mice not exhibiting social exploration preference at baseline were excluded from analysis.

The novel object exploration experiment was performed in the same three-chamber apparatus used for the social behavior tests, and using the same general method. Mice were placed in the center chamber with the doors to both side chambers closed. Light pulses were delivered during the 10 minute acclimation period, after which the doors were opened and the mice were allowed to explore the entire apparatus. In place of the wire mesh cups, novel objects were presented at random in either of the two end-chambers. Exploration of the novel objects was scored over a period of 10 minutes for each mouse as the time in which the mouse spent actively exploring the object. Objects used were either plastic balls, cubes or porcelain figurines, all of approximately similar size. Objects were thoroughly cleaned between tests to prevent odor traces.

The open-field chamber (50×50 cm) was divided into a central field (center, 23×23 cm) and an outer field (periphery). Individual mice were placed in the periphery of the field and the paths of the animals were recorded by a video camera. The total distance traveled was analyzed using the Viewer2 software (BiObserve, Fort Lee, N.J.). The open field test for each mouse consisted of a 5-min session divided into two 2.5 minute segments, with a 2 s 473 nm light pulse delivered between the two segments. Track length, velocity and % time in the center were scored for each mouse and averaged across mice for each condition The elevated plus maze was made of plastic and consisted of two light gray open arms (30×5 cm), two black enclosed arms (30×5×30 cm) extending from a central platform (5×5×5 cm) 31 at 90 degrees in the form of a plus. The maze was placed 30 cm above the floor. For each mouse, a 2 s 473 nm light pulse was delivered when the mouse was in the home cage. 5 minutes later, the fiberoptic connector was detached and the mice were individually placed in the center of the maze for a test duration of 15 minutes. Video tracking software (ViewerII, BiObserve, Fort Lee, N.J.) was used to track mouse location. All measurements displayed were relative to the entire mouse body.

Chronic Electrophysiological Recordings in Awake Mice

To simultaneously record from sites both within the virally-transduced tissue and outside of the transduced region, a novel chronic multisite optrode (CMO) was designed for awake animal recordings in combination with light delivery. Arrays of four 25 µm tungsten wires were used (California Fine Wire Company, Grover Beach, Calif.), wound together and cut at approximately 500 gm increments, and coupled these 4-wire bundles to an implantable fiberoptic lightguide (IFL; Doric Lenses, Quebec, Canada) that consisted of a 2.5 mm diameter metal ferrule from which a 200 µm-core fiberoptic cable extended. The four-wire bundle was back-fed into a 250 gm-diameter guide tube into which the fiberoptic cable was inserted. The wires were connected using gold pins to a Mill-Max connector, to which a stainless steel ground wire was also connected. The device was implanted stereotactically following virus injection (see above) such that the fiber tip only extended past the skull but not into brain tissue. The ground wire was inserted through a small craniotomy above cerebellum. Mice were allowed to recover for two weeks before experiments began.

To record neural activity during behavior, the mice were first acclimated over several days to the attachment of the headstage and the fiberoptic cable. The mice were allowed to explore the home cage with the headstage attached for 1-2 hours each day. Recordings were carried out 2-4 weeks after surgery. Signals were multiplexed at the head-stage into a 3-wire cable that was passed through an electrical commutator (PlasticsOne), demultiplexed using a demultiplexing board (Triangle BioSystems, Inc.) and digitized using Neuralynx Digital Cheetah. The fiberoptic and electrical commutators were suspended from a weighted arm (Harvard Apparatus) to allow the mouse to freely explore a large region (such as in the open field test). This configuration also prevented both the recorded mouse and juvenile intruders (during the social interaction test) access to any excess wire or optical fiber and minimized damage to the hardware. Videos were recorded using Neuralynx Cheetah software and analyzed offline with Viewer II (BiObserve, Fort Lee, N.J.) to quantify open-field behavior. Social interactions and novel object exploration were manually scored, as in other behavioral experiments. LFPs were filtered at 1 to 500 Hz and sampled at a frequency of 6.5 kHz. Multiunit activity was recorded at 32 kHz and individual events were collected with a threshold of 40 µV on all channels.

Wavelet power spectrograms of LFP recordings were analyzed as described above by sampling the power spectrum every 2 s for the duration of the recording. Power was calculated between 2 Hz and 120 Hz with a bin width of 2 Hz. In all mice, the effects of SSFO activation were recorded using a protocol of 2 minutes baseline recording, followed by a 1 s 473 nm pulse at an irradiance of 56 mW mm$^{-2}$ at the fiber tip. Following the blue pulse, activity was recorded for 2 minutes, followed by a 30 s deactivating light pulse at a wavelength of 594 nm light with similar intensity. Activity was then recorded for 2 additional minutes. For each mouse this protocol was repeated at least 4 times, and power spectra for each of the three periods (pre-activation, post-activation and post-deactivation) were averaged across the 4 repetitions.

Social behavior experiments with the electrode-implanted mice were performed using the home-cage paradigm, as described above. No-light and light trials were separated by at least 24 hours, using novel juvenile mice in each test. The test consisted of 2 minutes of baseline recording, then 1 minute of recording after the 1 s activation light pulse, after which the juvenile intruder was introduced. Social behavior was scored for 2 minutes, followed by removal of the juvenile and a 30 s 594 nm light pulse to deactivate SSFO. Recordings were acquired during the entire time and analyzed in the same way as described for the home-cage recordings above. Power spectra for the 2 min social interaction period were averaged across mice for both the no-light and light trials. The novel object experiment in these mice was conducted in an identical manner, replacing the novel juvenile mouse with an inanimate object.

Data Analysis

Statistical significance was calculated using paired or unpaired two-tailed t-tests, as applicable. Data were analyzed using Matlab Statistics toolbox or Microsoft Excel.

Immunohistochemistry

Animals that had undergone behavioral analysis were anesthetized with ketamine/xylazine and perfused transcardially with ice-cold PBS followed by 4% paraformaldehyde in PBS (4% PFA). Isolated brains were post-fixed in 4% PFA overnight at 4 C and subsequently immersed in a sterile cryoprotectant consisting of 30% sucrose in PBS until settling (2 to 3 days at 4° C.). 40 µm coronal slices were collected using a freezing microtome (Leica), washed in PBS, permeabilized in 0.3% Triton X-100 (PBST) and blocked in 3% normal donkey serum dissolved in PBS for one hour at room temperature. Nuclear localization of c-fos was determined using rabbit anti-c-fos (Calbiochem) on animals that had undergone 1 s 473 nm light stimulation 90 minutes prior to perfusion; parvalbumin targeting was confirmed using colocalization of mouse anti-parvalbumin (Sigma Aldrich) and fluorescent protein. Stained slices were visualized on a Leica SP5 confocal microscope. To calculate average fluorescence in different anatomical sub-regions, histology images were analyzed using ImageJ. Individual subregion images were thresholded at a fixed threshold level. Mean fluorescence above threshold was calculated and averaged per region between mice. c-fos counts were performed using standardized landmarks to identify regions and were anonymized prior to counting. Counting was done on z-stacks of the entire slice volume. Data were only compared across experimental conditions in experiments where c-fos induction was performed on the same day and in the same physical conditions, and where tissue preparation, staining and imaging were done under standardized conditions.

Results

First, to evaluate the effects of SSFO-induced activity in neuronal populations on a cellular level, the expression of the immediate-early gene product c-fos 90 minutes after a 2 s pulse of 470 nm light stimulation were examined in vivo (FIG. 3C). The number of c-fos positive neurons in the entire prelimbic/infralimbic subfield (delimited in FIG. 3B) was quantified in the virally-transduced and optically-stimulated hemisphere. In animals injected with the (control) CaMKIIα-YFP virus, 335±107 mPFC cells expressed detectable c-fos at baseline. By comparison, mice expressing SSFO in PV neurons (PV::SSFO mice) displayed significantly fewer c-fos expressing cells relative to controls in mPFC (81±7 cells, n=5 mice; p<0.005, two-sided t-test). Remarkably, a large fraction of these cells were in fact YFP-positive (61±8% out of the total c-fos positive population; FIG. 3C), indicating that even most of these active cells are in fact PV-positive neurons directly activated by the virally-delivered SSFO. In contrast, mice expressing SSFO in excitatory cells (CaMKIIα::SSFO mice) showed significant increases in c-fos positive nuclei in both the virally-transduced hemisphere (1455±305 cells; n=3 mice; p<0.05, two-sided t-test; FIG. 2C), and the contralateral hemisphere (617±97 cells; n=3 mice; p<0.05), but not beyond to other areas of the brain (FIG. 3M), indicating that activation propagated chiefly locally and to the contralateral hemisphere. These findings validate the expected targeting, efficacy, and directionality of SSFO in the awake mouse.

Three groups of animals to behavioral testing FIG. 3D-G) CaMKIIα::SSFO mice, PV::SSFO mice, and control mice (either injected with AAV5-CaMKIIα-eYFP virus or not injected with virus). Two to four weeks after surgery, conditioned learning and unconditioned social behavior was tested, as well as exploration of novel objects and locomotor functioning (FIG. 3D-G); all animals received a single 1 s pulse of 470 nm light through the implanted fiberoptic connector, followed by removal of the fiberoptic cable 1 minute before introduction into the behavioral chamber, capitalizing on the stability of the SSFO.

Striking deficits were observed in both social behavior and conditioning, selectively in the mice with elevated cellular E/I balance (FIG. 3D-G). First unconditioned social exploration of same-sex juvenile mice that had been introduced into the home cage of the experimental animal was explored[49]. Exploration of the novel mouse was virtually abolished in the elevated E/I (CaMKIIα::SSFO) group following a 1 s 470 nm light pulse, compared with controls (n=8.CaMKIIα::SSFO mice and n=6 controls; p<0.0005, unpaired t-test), while PV::SSFO mice showed no effect in this behavior (FIG. 3D and 2; n=6 PV::SSFO mice; p>0.1; unpaired t-test). The same mice were next subjected to a conditioning protocol performed immediately following delivery of a 1 s 470 nm light pulse. Twenty-four hours later, responses to the conditioned tone and context were assessed in order to evaluate the extent to which the mice learned to associate the conditioned and unconditioned stimuli while under the altered E/I states. The elevated E/I (CaMKIIα::SSFO) animals showed no conditioned responses (to either context: p<0.0005 or tone: p<0.05, compared with controls; two-sided t-test). Moreover, the deficit was fully reversible; the same animals could be reconditioned 24 hr later in the absence of SSFO activation, showing fear conditioning that was indistinguishable from that of the control group when tested the following day (FIG. 3E; p>0.1 cue and context; unpaired t-test). In contrast, the PV::SSFO group, in which E/I balance was reduced, showed no significant impairment in freezing behavior compared with controls in response to both tone and context (FIG. 3E; p=0.09 and p=0.56, respectively; two-sided t-test), just as in the social behavior. The behavioral deficits associated with elevated E/I balance were not attributable to changes in motor function since in the same mice, open field behavior was normal (n=8 CaMKIIα::SSFO mice and n=6 CaMKIIα::YFP mice; FIG. 3F and FIG. 3N).

Example 4

Elevation but not Reduction of Cellular E/I Leads to Quantitative Reduction in Information Processing Next, neurophysiological underpinnings of the behavioral impairments resulting from prefrontal E/I balance alterations was investigated. In autism, a finding of 30% co-morbidity with debilitating seizures has led to the suggestion that hyperexcitation is involved, and altered cortical excitation or inhibition have been proposed to underlie some of the core behavioral deficits in both autism and schizophrenia.

Materials and Methods

Acute 300 pm coronal slices isolated from 8-9 week old wild-type C57BL/6J or PV::Cre mice previously injected with virus were obtained in ice-cold sucrose cutting solution ([mM] 11 D-glucose, 234 sucrose, 2.5 KCl, 1.25 $NaH_2PO_4$, 10 $MgSO_4$, 0.5 $CaCl_2$, 26 $NaHCO_3$) using a Vibratome (Leica). Slices were recovered in oxygenated Artificial Cerebrospinal Fluid (ACSF; [mM] 124 NaCl, 3 KCl, 1.3 $MgCl_2$, 2.4 $CaCl_2$, 1.25 $NaH_2PO_4$, 26 $NaHCO_3$, 10 D-glucose) at 32° C. for one hour. Individual neuron patches were obtained after identifying fluorescent protein expression from indicated prefrontal cortical layer under constant ACSF perfusion. Filtered light from a broad-wavelength xenon lamp source (Sutter Instruments DG-4) was coupled to the fluorescence port of the microscope (Leica DM-LFSA). Before each experiment, a 20 s pulse of 590 nm light was applied to convert all of the SSFO channels to the dark state and prevent run-down of photocurrents. Cultured cell images were acquired on the same microscope using a Retiga Exi CCD camera (Qimaging inc.) at 100 ms exposure with the 30 gain. Illumination power density was 12 mW $mm^{-2}$ at 500 nm with a standard EYFP filter set. Quantification of fluorescence was done with ImageJ software by marking a region containing the soma and proximal neuritis and calculating for each cell the total integrated pixel intensity in that region, rather than average fluorescence, since photocurrents are likely to be related to the total number of membrane-bound channels rather than average channel expression per area. Photon flux calculations for SSFO integration properties were done by calculating the photon flux through the microscope objective at each light power, and then dividing to reach the photon flux across the cell membrane, based on the capacitance of individual patched cells.

For live animal studies, simultaneous optical stimulation and electrical recording in the prefrontal cortex of wildtype adult C57/BL6 male mice previously transduced with indicated viral constructs as described above. Briefly, animals were deeply anesthetized with isoflurane prior to craniotomy. After aligning mouse stereotactically and surgically removing skull dorsal to prefrontal cortex (centered at 1.8 mm anterior, 0.35 mm lateral), a MO 0.005 inch extracellular tungsten electrode (A-M systems) with its tip coupled approximately 400 μm below the blunt end of a 0.2 N.A. 200 μm core diameter fiber optic cable (ThorLabs; "optrode") was stereotactically inserted into the virally-transduced brain region. Recorded signals were bandpass filtered between 300 Hz and 20 kHz, AC amplified 10000× (A-M Systems 1800), digitized (Molecular Devices Digidata 1322A) and recorded using Clampex software (Molecular Devices). Clampex software was used for both recording field signals and controlling 47 3 nm (OEM Laser Systems) and 561 nm (CrystalLaser)—10 mW solid state laser diode sources coupled to the optrode. Electrophysiological recordings were initiated at the Cg/PL boundary (1.8 mm anterior, 0.35 mm lateral, −2.0 mm ventral) after lowering isoflurane anesthesia to a constant level of 1%. Optrode was lowered ventrally in −0.1 mm steps. Events were isolated using a custom algorithm in Matlab (MathWorks) with the threshold set above baseline noise (25 to 40 μV). Heatmap images were generated in Matlab from an unweighted moving average of 2 s with 200 ms steps. Moving average value was reset at the onset of external manipulations (beginning of sweep, initiation of light pulses).

Results

Figure 4:
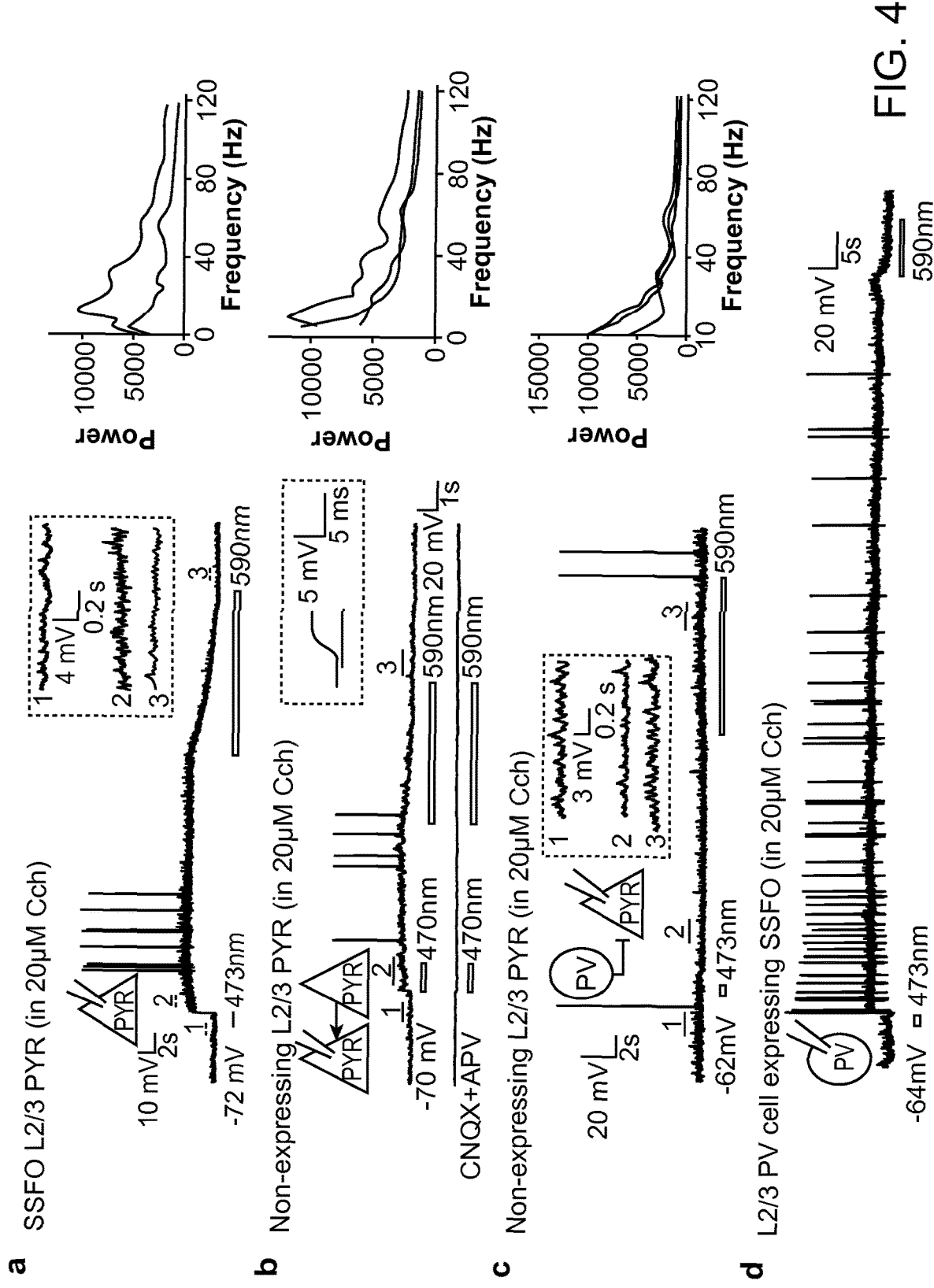
FIG. 4 depicts SSFO activation in pyramidal cells increases network activity and impairs information transmission through principal neurons. (a) Whole cell recording from a layer 2/3 pyramidal neuron expressing SSFO in a prefrontal cortical slice from a mouse injected with AAV5-CaMKIIα-SSFO-EYFP. Activation with 470 nm light triggered depolarization of the recorded cell. Inset compares expanded 2 s periods pre-activation (1), post-activation (2) and post-deactivation (3). (b) Whole cell recording in a non-expressing pyramidal neuron from a slice expressing CaMKIIα::SSFO-EYFP shows increased synaptic activity (top) following a 1 s 470 nm light pulse, which is eliminated by excitatory synaptic blockers CNQX (10 μM) and APV (25 μM; bottom). Inset compares activity pre-activation (1), post-activation (2), and post-deactivation (3). (c) Sample trace showing response of a representative pyramidal neuron in a PV::SSFO slice (expressing DIO-SSFO-EYFP) at baseline and during 5510 activation in PV cells in the slice (between blue and yellow light pulses). Inset compares three 5 s periods before activation (1), after activation (2), and after deactivation (3). (d) Activity of PV cells after activation with SSFO.

To probe circuit physiology manifestations of the E/I balance alterations within the prefrontal microcircuit that lead to the behavioral impairments, acute prefrontal cortical slices from CaMKIIα::SSFO mice were prepared. Whole-cell recordings were conducted in the presence of ongoing asynchronous synaptic activity induced by the cholinergic agonist carbachol at 20 μM52-54; spiking was never observed with SSFO activation alone. Circuit-wide SSFO activation with a single blue light pulse had the effect of depolarizing the recorded SSFO-expressing neurons by 9.8±1.4 mV (n=7 cells; FIG. 4A), in part by triggering an increase in incoming synaptic activity (FIG. 4A, inset); both effects were terminated with yellow light. Spectral analysis of responses to SSFO in both expressing and non-expressing cells revealed that this increased activity displayed a broad spectral range with a peak above 20 Hz (FIG. 4A-B). In contrast, pyramidal cells in slices expressing SSFO in PV cells showed a robust reduction in synaptic activity and a reduction in power at low frequencies (FIG. 4C), consistent with the increased activity of PV cells after activation with SSFO (FIG. 4D).

Together, these data and the c-fos data in FIG. 3 revealed that interventions to either elevate or reduce cellular E:I balance in mPFC robustly influenced neocortical neuronal activity, but since only elevating cellular E:I balance in mPFC induced behavioral deficits, it was decided to make an attempt to understand at a deeper level how information processing in mPFC was altered in either case. To examine the effects of altered E/I balance on information transmission in the prefrontal microcircuit, whole-cell recordings in acute slices from CaMKIIα::SSFO mice were performed in which opsin-expressing pyramidal neurons were identified by morphology and fluorescence. Neurons in whole-cell patch clamp were stimulated with trains of simulated EPSCs designed to span a wide range of sEPSC rates over time (FIG. 5A) cells expressing SSFO, blue light activation indeed enhanced excitability at low sEPSC rates but led to a saturation of the input-output (IO) curve at higher sEPSC rates (FIG. 5B), thereby causing a significant reduction in mutual information between the rate of input EPSCs and the rate of resulting spikes (−0.40±0.09 bits; p=0.011, paired Student's t-test; FIG. 5C), and demonstrating that increased cellular E/I balance quantitatively impairs information processing in neocortical principal cells. Next, to examine the effects of reduced cellular E/I balance on information processing in neocortical principal cells, acute slices from PV::SSFO mice and stimulated non-expressing pyramidal cells with sEPSC trains were recorded as before (FIG. 5D). Activation of SSFO in PV cells caused a substantial decrease in the IO curve gain in the recorded pyramidal cells (FIG. 5E) as expected via synaptic inhibition, but in this case preserved the overall shape of the IO curve without saturation and strikingly had no significant effect on mutual information between the rate of input sEPSCs and the resulting spike rate in pyramidal cells (FIG. 5F).

Figure 5:
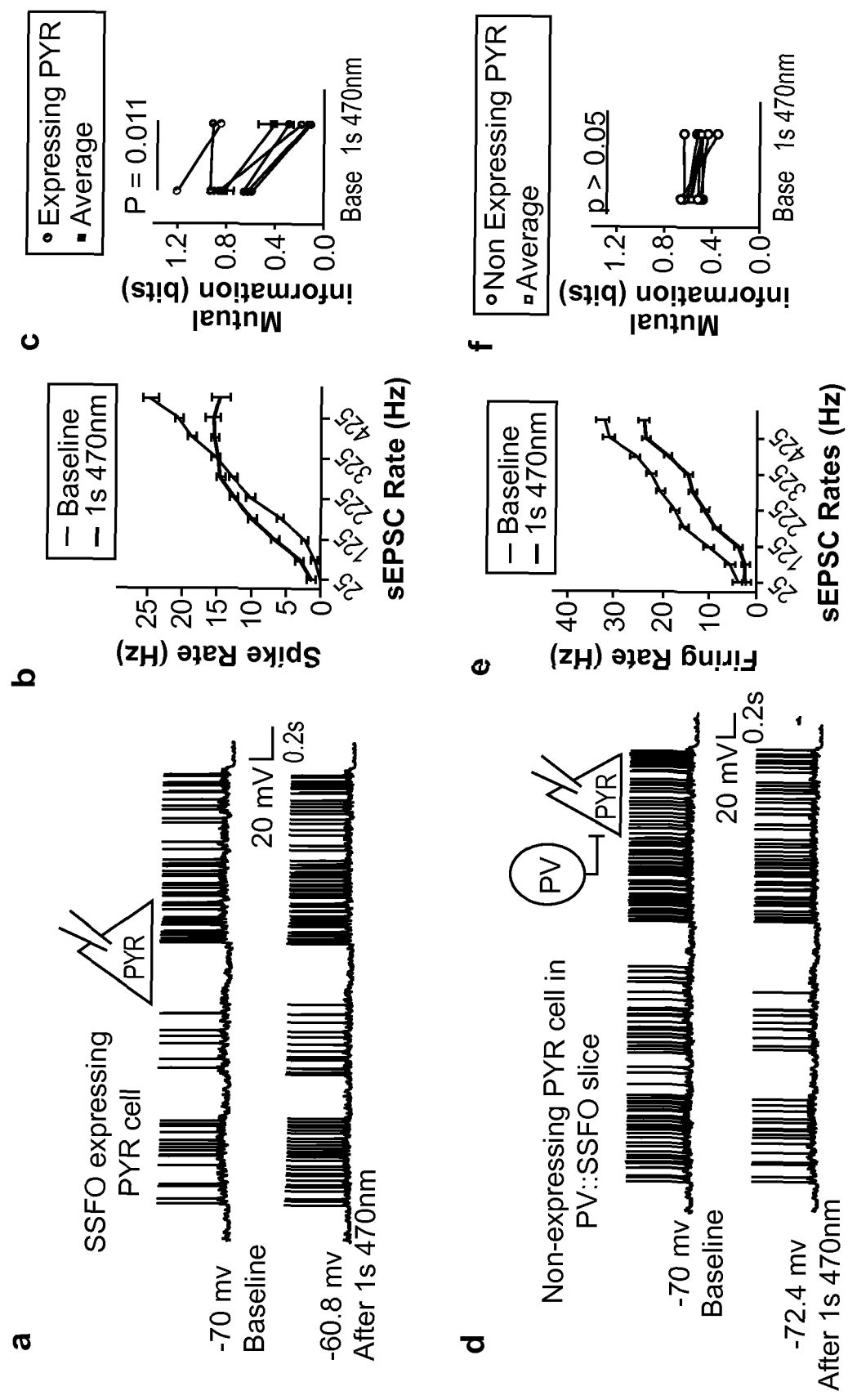
FIG. 5 depicts impaired cellular information processing in elevated but not reduced cellular E/I balance. (a) Representative traces showing response of a representative CaMKIIα::SSFO-eYFP expressing cell to injection of an identical defined pattern of sEPSCs before (top) and after (bottom) blue light activation. Resting membrane potential for each trace is indicated. (b) Input-output curve for a pyramidal neuron expressing SSFO, showing reduced response to higher sEPSC rates after SSFO activation (pre-stimulation: black; post-stimulation: gray; error bars show s.e.m). (c) Cell-by-cell reduction in transmitted mutual (EPSC-spike) information in 6 individual pyramidal cells expressing SSFO following the is 470 nm pulse. Average MI is shown in black (mean±s.e.m; p=0.0063, Student's t-test; reduction in mutation information between spike rate and injected sEPSC rate obtained within 125 ms windows). (d) Representative traces showing responses of a pyramidal neuron from a slice expressing DIO-SSFO-eYFP to an identical injection of sEPSCs as in a before (top) and after (bottom) blue light activation. Resting membrane potential for each trace is indicated. (e) Input-output curve for a pyramidal neuron in a PV::SSFO slice, showing linear reduction in gain after SSFO activation in PV neurons (pre-stimulation: black; post-stimulation: blue; error bars show s.e.m). (f) Cell-by-cell summary data showing no significant reduction in pyramidal cell transmitted information, despite spike suppression, after a 1 s 470 nm pulse that triggered activation of DIO-SSFO in PV neurons. Mean MI is shown in black. (g) Mean mutual information across cells in baseline vs. SSFO-activated conditions across a range of time bin widths used for calculating mutual information. For these comparisons, the bin width of input sEPSC rate was kept constant at 50 Hz. Asterisks indicate the significance of the change in mutual information in SSFO-activated conditions (h) Comparison of mean change in mutual information (SSFO-activation minus baseline) in cells recorded from slices expressing CaMKIIα::SSFO or PV::SSFO. Asterisks indicate the significance of the difference in magnitude of the change in mutual information for CaMKIIα::SSFO vs. PV::SSFO. (i) Same as in (g), but with varying input sEPSC rate bins. Here the time bin width was kept constant at 125 ms. (j) Same as in (h), but with varying input sEPSC rate bins. All bar graphs depict mean±s.e.m. (* p<0.05; ** p<0.01).
Figure 5:
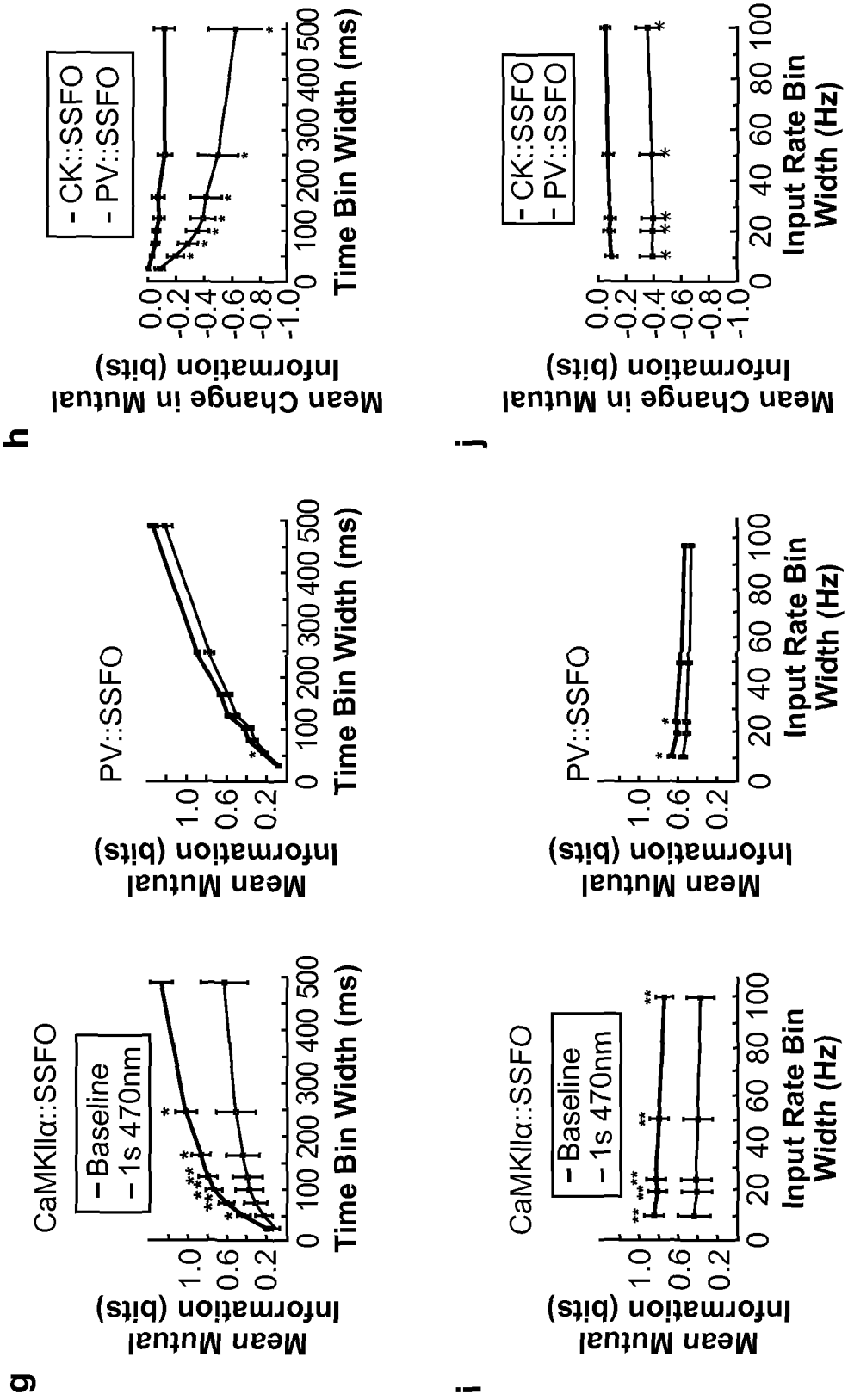

The decrease in information throughput for principal mPFC cells was significantly larger (4.8-fold, p=0.0144, unpaired t-test) following light activation in CaMKIIα::SSFO mice versus PV::SSFO mice across a broad range of both time bin width (FIG. 5G-H) and input rate bin width (FIG. 5 I-J) used to calculate mutual information, despite the fact that there was (if anything) a greater impact on spike rate with the PV::SSFO activation (FIG. 5B, E). Together these behavioral and informational data illustrate that, despite the natural intuitive supposition that favoring inhibition would be more disruptive to information processing, it is in fact elevations in E/I balance that are detrimental for mPFC circuit and behavioral performance, consistent with the clinical association of disorders such as autism with increased-excitability phenotypes. If the cellular E/I balance-induced social dysfunction demonstrated here were related to the circuit processes and social dysfunction seen in severe human neuropsychiatric disease states such as autism and schizophrenia, an important prediction would be that characteristic electrophysiological markers of these human disease states would also be seen in this animal model. Since a common clinical electrophysiological marker of both autism and schizophrenia is elevated baseline (non-evoked) gamma power (30-80 Hz), this physiological-marker hypothesis was therefore tested by measuring this consistent clinical marker in awake, freely-moving mice with specifically elevated cellular E/I balance.

Testing for this possibility with the requisite sensitivity required the additional insertion of multi-site recording electrodes into mPFC. While the additional presence of such a device in combination with a penetrating fiberoptic for light delivery might be too acutely disruptive and spatially invasive for the small mouse mPFC circuitry, a strategy with two important features to enable this experiment was developed and implemented. First, the recording device was designed for chronic implantation, so that recordings could be carried out in animals habituated to the recording electrodes. Second, the photon integration properties of SSFO were capitalized upon to enable not only behavioral testing without optical hardware, but also (even for deep structures like IL and PL) without any optical hardware penetration of the brain itself, at any time. To verify that it is indeed possible to modulate SSFO-expressing cells in deep cortical structures, CaMKIIα::SSFO or CaMKIIα::EYFP virus were injected and implanted fiberoptic connectors extending only past the skull (FIG. 6A), without entering the cortical surface (FIG. 6B). The directionality of E/I balance elevation in this minimally-invasive configuration was validated by c-fos analysis in these animals (n=3 CaMKIIα::SSFO and n=4 CaMKIIα::EYFP control mice; p 0.034, two-sided t-test; FIG. 6C). Elevated cellular E/I balance during conditioning showed no effect on freezing responses to foot-shock (indicating intact sensory perception of the aversive unconditioned stimulus; FIG. 6D), but showed a marked and fully reversible effect on contextual (p<0.005; unpaired t-test with unequal variance) and auditory conditioning (p<0.005; unpaired t-test with unequal variance; FIG. 6D). Crucially, social behavior was also impaired in mice receiving noninvasive light stimulation prior to testing (p<0.005; unpaired t-test; FIG. 6E), demonstrating the opportunity afforded by the extreme light sensitivity of the SSFO.

Figure 6:
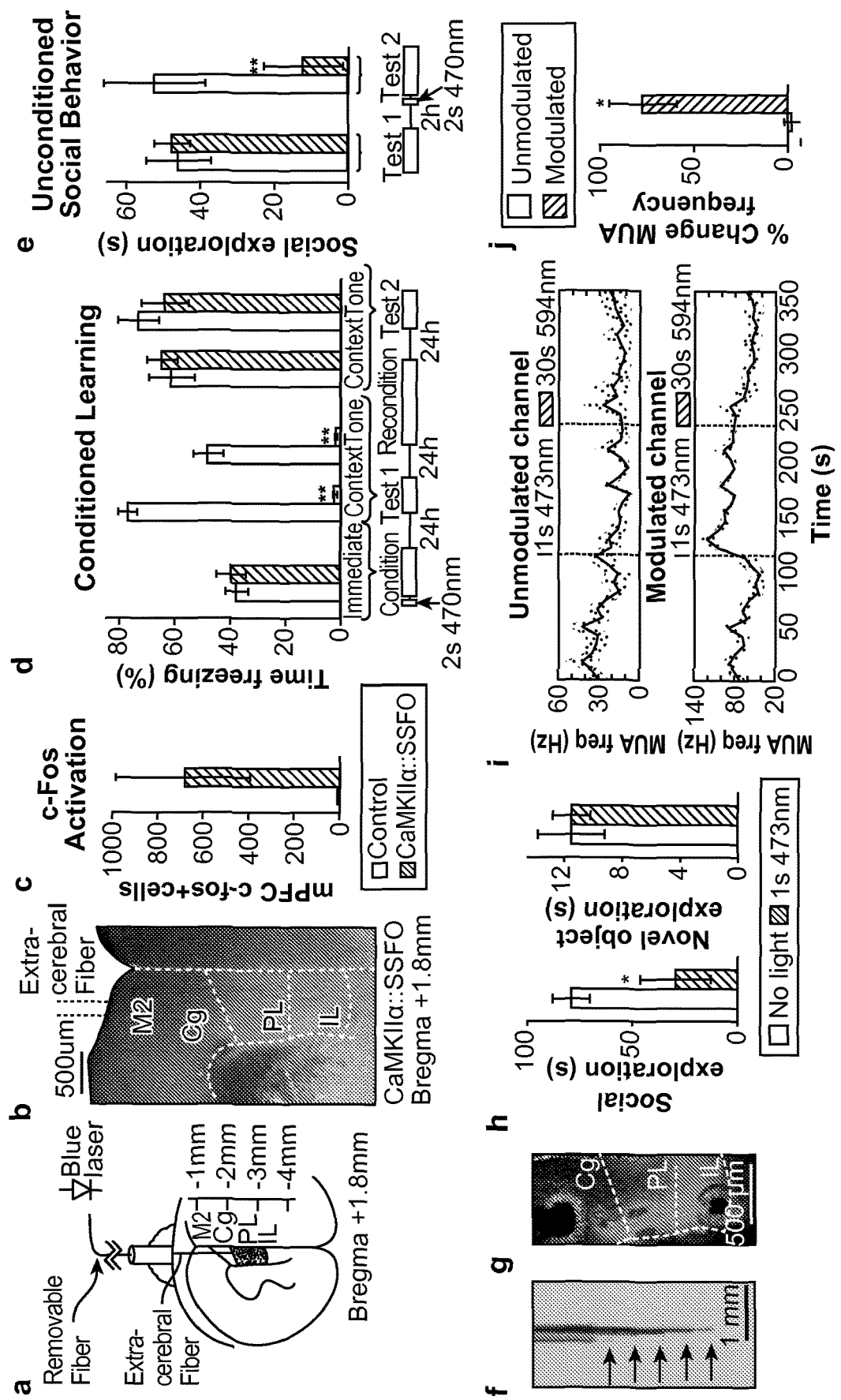
FIG. 6 depicts elevated cellular E/I balance in mPFC drives baseline gamma rhythmicity in freely-moving, socially impaired mice. (a) Wild-type mice injected with CaMKIIα::SSFO or CaMKIIα::EYFP were implanted with a non-brain-penetrating fiberoptic connector via a small craniotomy at the time of virus injection. (b) Representative image of viral expression of SSFO-eYFP in PL cortex in a mouse implanted with non-brain-penetrating fiberoptic connector. (c) c-fos positive cell counts in PFC of control (CaMKIIα::EYFP) mice or CaMKIIα::SSFO mice, 90 min after activation with a 2 s 470 nm light pulse. (d) Freezing behavior assessed in non-brain-penetrating implanted mice that received a 2 s 470 nm light pulse immediately prior to the conditioning session. Freezing was measured immediately following the conditioning session (Immediate), 24 h later (Test 1), and then 24 h following a second fear conditioning session in which no light was delivered (Test 2). (e) Social exploration was measured either with no light activation (Test 1) or following a 2 s 470 nm light pulse (Test 2). (f) Implantable chronic multisite optrode (CMO) for awake, behaving recordings in mouse M2 and PFC. Arrowheads indicate wire termination sites; arrow shows cleaved end of fiberoptic connector. (g) Electrolytic lesions mark the sites from which recordings were taken in a mouse expressing CaMKIIα::SSFO. (h) Social exploration (left) and novel object exploration (right) before (gray left vertical bar) and after (blue right vertical bar) activation with 470 nm light in the three mice in which CMO recordings were conducted (n=3 mice). (i) Multiunit activity from two channels simultaneously recorded during an activation/deactivation protocol. Blue light and yellow light were delivered as indicated. Channels with significant multiunit modulation (bottom) were selected for spectral analysis. (j) Average increase in MUA rate on channels within the expressing region (blue right vertical bar; n=4 channels in 3 mice), compared with channels that were outside the expressing region (gray left vertical bar; n=4 channels in 3 mice). (k) LFP wavelet spectrogram from an un-modulated channel. Example traces are shown for the baseline, activation and deactivation periods. Average wavelet spectra for the three indicated periods (n=5 trials in 1 mouse) and population data of power change in 3 frequency ranges (inset; n=3 mice) are shown. (l) LFP wavelet spectrogram from a modulated channel. Example traces are shown for the baseline, activation and deactivation periods. Average wavelet spectra for the three indicated periods (n=5 trials in 1 mouse) and population data (inset; n=3 mice) are shown, demonstrating a specific increase in gamma rhythmicity after SSFO activation in PFC pyramidal neurons. All bar graphs depict mean±s.e.m. Power spectra in (k), (l) are averaged from 5 trials, shaded areas indicate standard deviation across recordings. (* $p<0.05$; ** $p<0.005$).
Figure 6:
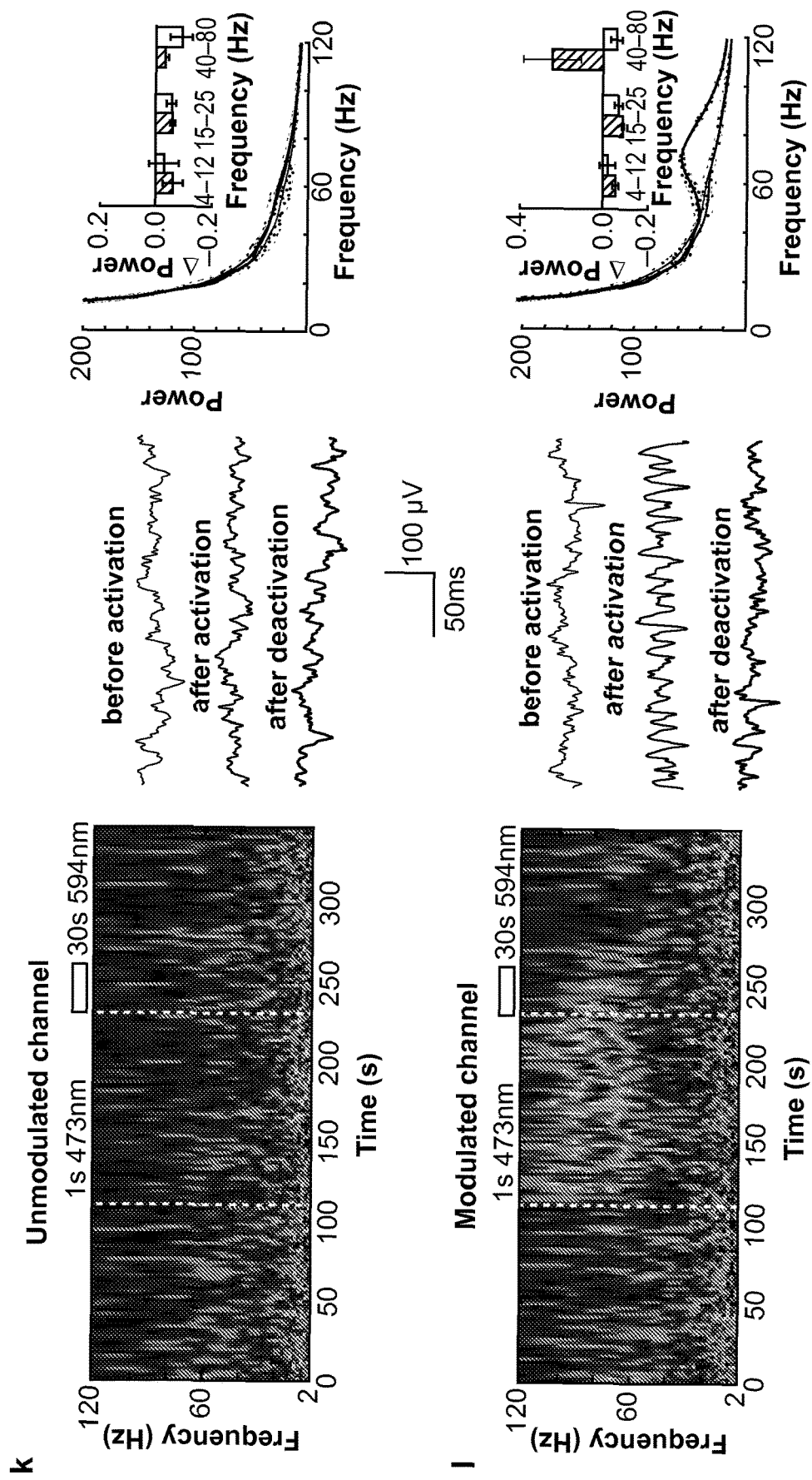
Figure 7:
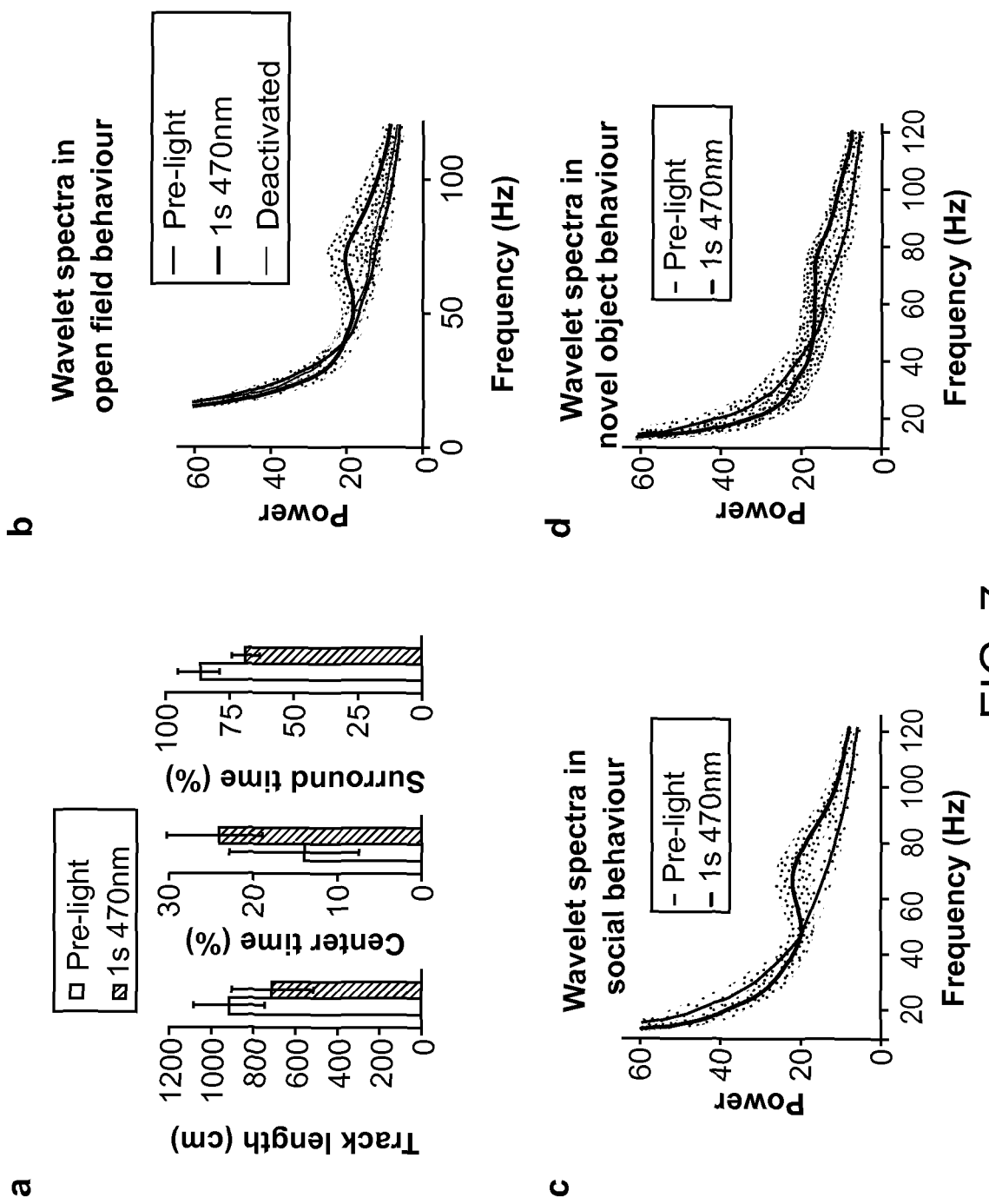
FIG. 7 depicts locomoter behavior in a novel open field behavioral test. (a) Open-field behavior of mice expressing CaMKIIα::SSFO in mPFC pre-activation (dark gray bars; 2.5 min) and post-activation (light gray bars; 2.5 min) with 1 s 473 nm light. Track length, % time in center, and % time in the periphery are shown (n=3 mice). A yellow light pulse was applied after the second 2.5 min period to deactivate SSFO. (b) Average power spectra, measured pre-activation (black), post-activation (dark gray) and post-deactivation (light gray) from channels determined to arise from electrodes placed in the virus-expressing mPFC region (n=3 mice, shaded areas indicate s.e.m across mice). (c) Average power spectra measured from channels in i during the social behavior test in trials without light activation of SSFO (gray) and with activation (light gray). (d) As in (b), for novel-object exploration experiments (n=3 mice, shaded areas indicate s.e.m across mice). Note that unmodulated channels did not show significant changes in power spectrum following light activation.

To obtain direct electrophysiological readouts from these mice, a novel chronic multisite optrode (CMO) was designed in which the fiberoptic connector is coupled through a guide tube with 4 25-μm tungsten wires, cut at 0.5 mm distance increments from the tip of the fiber, to simultaneously sample neural activity at various depths within the illuminated tissue (FIG. 6F). At the end of the experiments, electrode positions were marked using electrolytic lesions (FIG. 6G), which allowed us to identify the anatomical locations from which individual recordings were taken; no fiberoptic penetration of the tissue was allowed to occur. In three mice that were injected with CaMKIIα::SSFO virus and implanted with the depth-sampling optrode, it was first confirmed that social behavior was normal at baseline, and impaired following a 1 s 470 nm pulse (FIG. 6H; p=0.044, paired Student's t-test). The same animals showed no effect of light on exploration of a novel object, however, consistent with our previous findings (FIG. 6H; p=0.82, paired Student's t-test). Additionally, locomotor behavior in the familiar home-cage (not shown) and in a novel open field were not significantly altered after the 1 s activation pulse (FIG. 7A) although a trend toward reduced anxiety was apparent (increased % time in center; FIG. 7A). During these experiments to validate the behavioral phenotypes in the setting of CMO implantation, activity was recorded simultaneously on all channels and the changes resulting from SSFO activation was analyzed.

Recordings in the animals' home cage were first analyzed using a protocol that consisted of 2 minutes pre-activation baseline, a 1 s 470 nm light pulse, 2 minutes of continuous recording and then a 30 s pulse of 590 nm light to fully deactivate SSFO. This protocol was repeated 4 times in each mouse and unit activity traces were averaged across trials (FIG. 6I). In multiunit recordings from channels within the SSFO-expressing regions, significant increases in spiking in response to the blue light pulse (FIG. 6 I-J; 77±18% on modulated channels was observed, compared with −3.4±4.4% on the unmodulated channels; n=4 modulated and 4 unmodulated channels in 3 mice recorded; p=0.02; two-sided t-test).

Also observed were pronounced changes in the local field potential (LFP) recordings from the modulated channels. Wavelet spectral analysis was used to generate time-resolved spectrograms (FIG. 6 K-L; left) of the LFP activity on each channel and quantified the average change between the pre-activation baseline and the post-activation period. In unmodulated channels there was no apparent effect of the activation pulse on the LFP (FIG. 6K, left), with only a small average decrease in power across all frequencies in the post-activation and post-deactivation periods compared with the baseline period (FIG. 6K, right). In contrast, modulated channels located within virally-transduced regions showed a marked increase in gamma-band activity (FIG. 6L) after activation with SSFO, which was sharply temporally delimited to the activation period and was terminated by the 590 nm deactivation pulse (FIG. 6L, right). The increase in gamma-band activity was associated with a reduction in lower-frequency power within the same channels that showed increased gamma activity (FIG. 6L, right; inset). A similar analysis of the recordings performed during the behavioral experiments done with these animals showed consistently increased gamma-band activity in the experiments where a 1 s 470 nm light pulse was delivered during behavioral testing in the open field experiment (FIG. 7B), the social exploration test (FIG. 7C) and the novel object exploration test (FIG. 7D). Together these data reveal that the physiological biomarker (elevated baseline gamma-band activity) seen in autism and schizophrenia is conserved with selectively elevated cellular E/I balance in freely-behaving mammals with social deficits.

Finally whether the neocortical circuitry that both induced and expressed the elevated E/I balance-induced gamma in vivo (FIG. 6) could also give rise to this physiological phenomenon in itself, in the absence of other brain regions was tested. While acute slices are more refractory to induction of sharp oscillation patterns than in vivo preparations, even in this reduced preparation an 20-80 Hz band power elevations in current-clamp membrane potential was noted under conditions of moderate CaMKII::SSFO activation (FIG. 4A-B) and 30-80 Hz gamma elevations in current-clamp membrane potential using the most potent channelrhodopsin available (CaMKII::C1V1-E162T).

Figure 8:
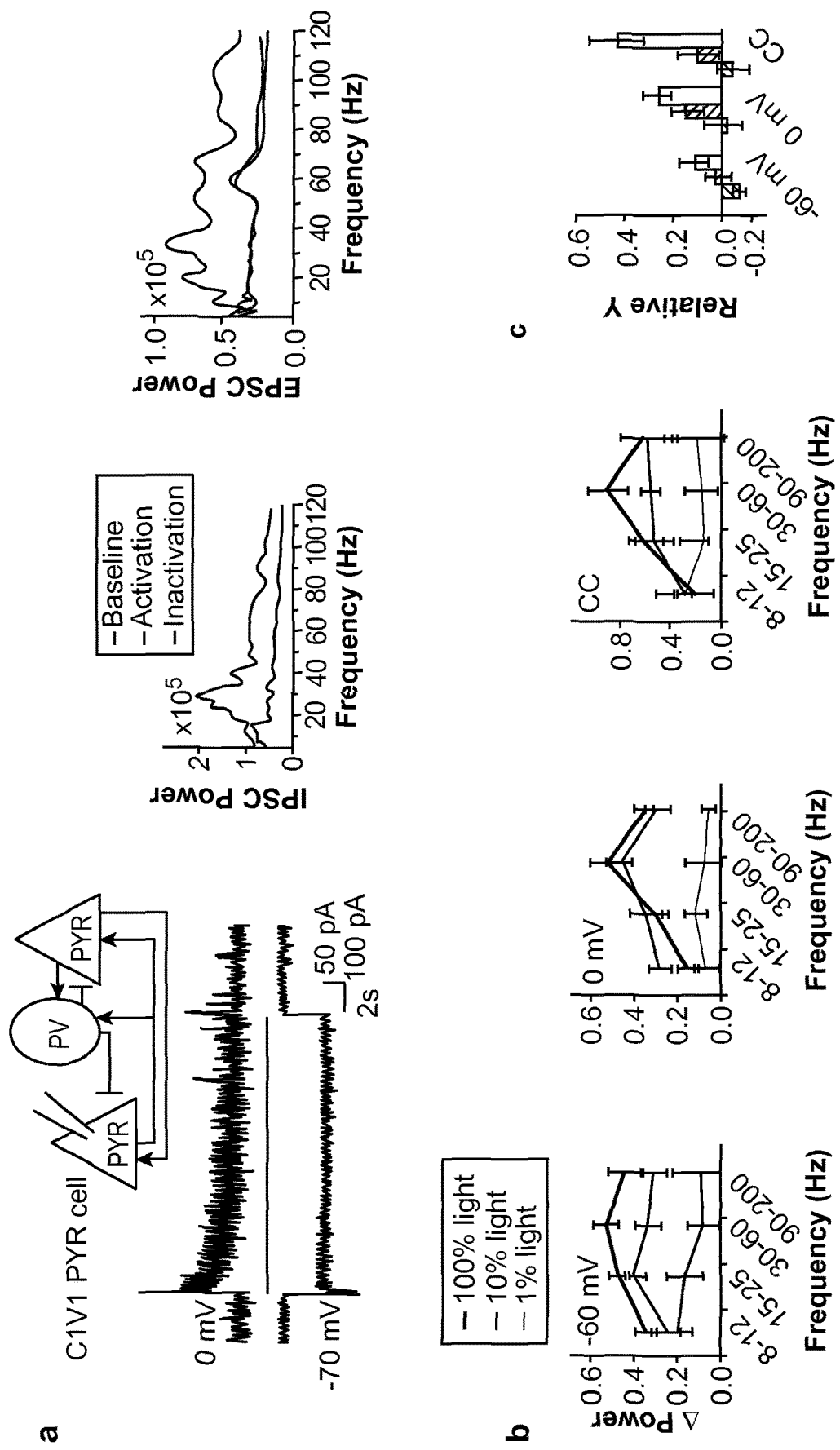
FIG. 8 depicts increase in power at gamma frequency under high light density. (a) voltage clamp experiment with corresponding spectra for IPSCs recorded at 0 mV and for EPSCs at −60 mV (b) Change in power of synaptic activity within the indicated frequency bins recorded in mPFC pyramidal neurons during a 20 s pulse of 560 nm light at the indicated light power densities. Power differences are shown between baseline (pre-light) period to light-on period when voltage clamping the cells to −60 mV or 0 mV, or in current clamp (CC) mode. Strongest gamma-modulation is evident at the highest light power density, and is strongest in 0 mV and CC recordings. (c) Relative gamma power for the three light powers in the three recording configurations from (b).

At high light power density (12 mW mm-2), the largest increase in power at gamma frequency (30-80 Hz; FIG. 8B) was observed. At lower light powers (4.3 mW mm$^{-2}$ and 0.6 mW mm-2), monotonically reduced gamma power along with relatively increased power at lower frequencies was observed (theta, 8-12 Hz and beta, 15-25 Hz; FIG. 8 B-C). Under voltage clamp conditions, corresponding spectra both for IPSCs recorded at 0 mV and for EPSCs at −60 mV were resolved (FIG. 8A). Together these results are consistent with a monotonic relationship between stable E/I balance elevation and the physiological biomarker of intrinsically-generated gamma oscillations in prefrontal cortex.

Figure 9:
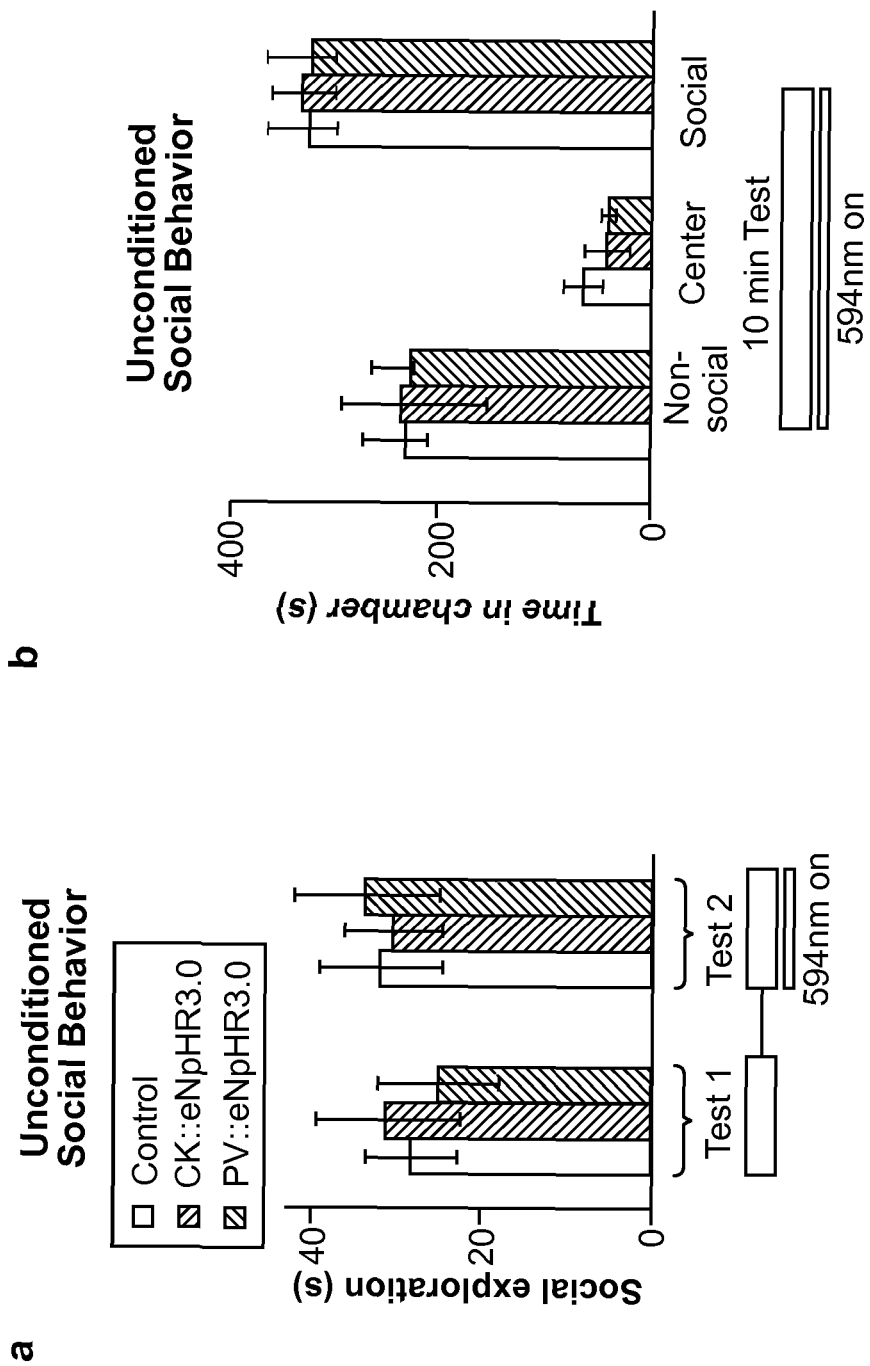
FIG. 9 depicts inhibition of PFC excitatory or inhibitory cells. (a) Wild-type mice bilaterally injected with CaMKIIα::eNpHR3.0, PV::Cre mice bilaterally injected with EF1α::DIO-eNpHR3.0, and control mice bilaterally injected with CaMKIIα-EYFP were tested in social exploration in the home cage (a; n=6 for all conditions) and the three-chamber social test (b; n=3, 5, and 6, respectively). Social behavior in the home cage was not affected under these conditions (a; $p>0.5$ for both NpHR3.0 groups compared with controls, unpaired t-test) and all three groups showed similar social preference in the three chamber social test (b; $p>0.5$ for both NpHR3.0 groups compared with controls, unpaired t-test) and significantly preferred the social chamber (b; $p<0.05$, paired t-test). Due to expression penetrance, the inhibition of PV cells in these experiments is expected to leave activity in the vast majority of inhibitory neurons (and even PV neurons) unchanged.

The data presented here point to specific impairments in social behavior as a result of elevated E/I ratio in mPFC. In principle an elevated E/I ratio could also be achieved by inhibiting inhibitory cells, although this loss-of-function approach would be expected to show effects only in the unlikely event that there were high stable baseline activity patterns of the inhibitory cells. Indeed, when AAV5-EF1α-DIO-eNpHR3.0-EYFP virus was injected into mPFC in both hemispheres of PV::Cre mice (generating PV::eNpHR3.0 mice) and implanted bilateral fiberoptic connectors for the home-cage or three-chamber social exploration paradigm, no behavioral impairment was found associated with activation of eNpHR3.0 under these conditions (FIG. 9), as may have been expected. However, a more important question central to the elevated cellular E/I ratio hypothesis is the prediction that increased inhibition could act in the direction of rescuing the behavioral deficits associated with elevated E/I balance caused by SSFO activation in excitatory cells (FIG. 3).

Figure 10:
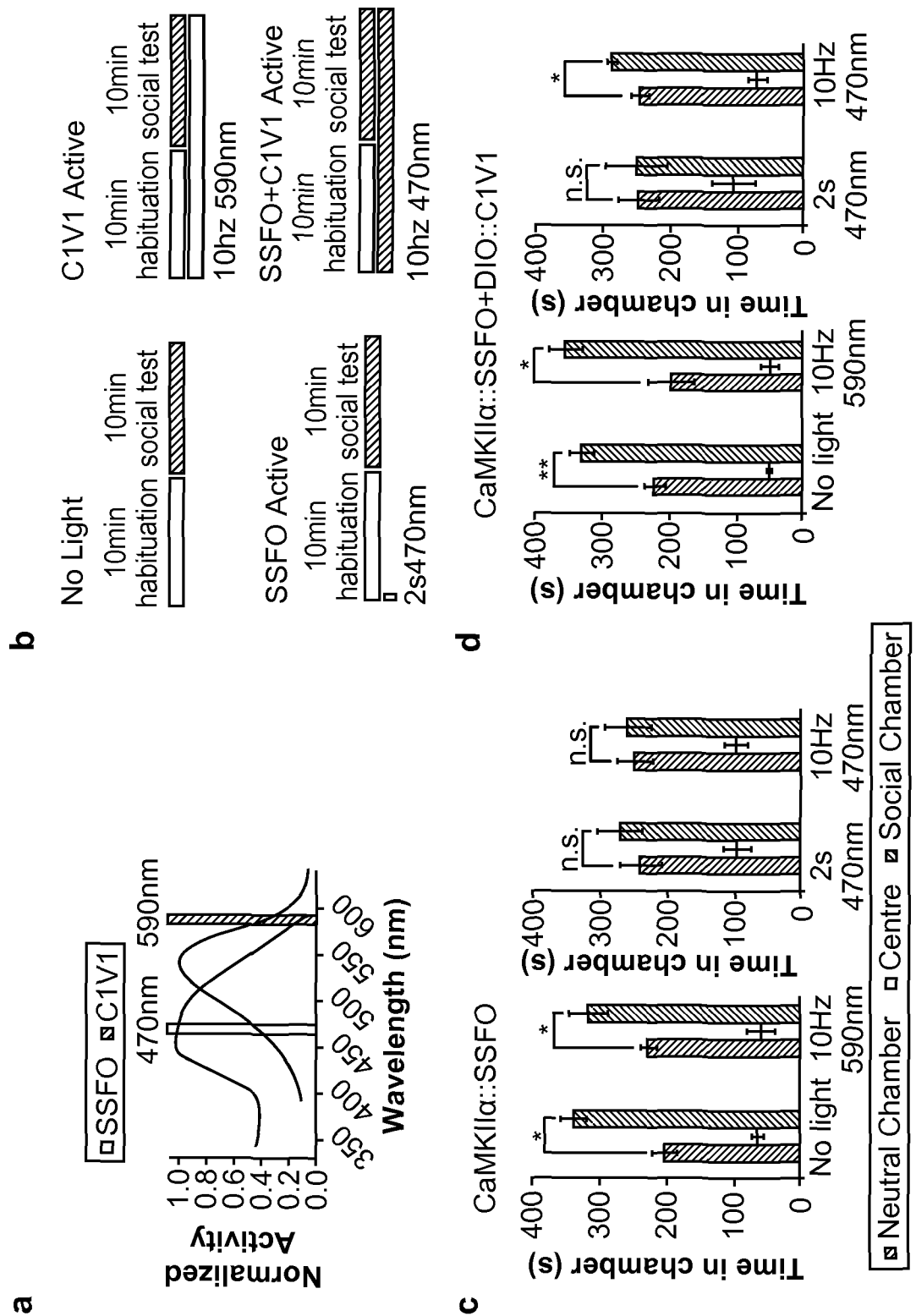
FIG. 10 depicts combinatorial optogenetics in behaving mammals: rescue of elevated E/I-balance social behavior. (a) Action spectra of SSFO and C1V1-E122T/E162T (C1V1). Vertical lines indicate stimulation wavelengths used in the experiments. (b) Experiment design and pulse patterns; no-light control was used for baseline behavior; 2 s 470 nm light was used to activate SSFO, transiently activating CIV1 only during the light pulse; 10 Hz 470 nm was used to co-activate SSFO and C1V1; 10 Hz 590 nm activated only C1V1. (c) Mice expressing CaMKIIα::SSFO showed significant social preference at baseline, but exhibited social dysfunction after either 2 s 470 nm activation or during 10 Hz 470 nm activation. (d) Mice expressing both CaMKIIα::SSFO and (DIO) PV::C1V1 showed impaired social behavior after a 2 s 470 nm pulse, but displayed restored social behavior during the 10 Hz 470 nm light stimulation. Activation of C1V1 alone with 10 Hz 590 nm pulses did not impair social behavior.

C1V1 is a chimeric light-sensitive protein derived from the VChR1 cation channel from *Volvox carteri* and the ChR1 cation channel from *Chlamydomonas Reinhardti* C1V1 and its variants, permits the experimental manipulation of cortical E/I elevations and the monitoring of gamma oscillations in cortical slices with high potency (thus allowing enable dose-response tests), low desensitization (thus permitting inducement of step-like changes in E/I balance), and red-shifted excitation (to permit separable drive of different populations within the same neural circuit). For this example, C1V1 variant with the highest potency to enable the most reliable dose-response was selected. To test the above prediction, a combinatorial optogenetic experiment for freely moving mice was designed, leveraging the unique spectral and temporal properties of C1V1 and SSFO to drive pyramidal cells with SSFO and co-activate (or not) PV cells using C1V1-E122T/E162T for maximal spectral separation. PV::Cre mice were injected with a combination of AAV5-CaMKIIα-SSFO and AAV5-EF1α-DIO-C1V1-E122T/E162T into mPFC to express SSFO in pyramidal neurons and C1V1 in PV cells (referred to here as SSFO/C1V1 mice; n=7). A second group of mice was injected with only CaMKIIα-SSFO virus (CaMKIIα::SSFO, n=9) and control mice were injected with CaMKIIα-EYFP (n=10). Two to four weeks later, the mice were tested in the three-chamber social test under 4 different illumination paradigms, utilizing the spectrotemporal strategy for separation between C1V1-E122T/E162T (driven with 590 nm light) and SSFO (driven for potent currents at the 470 nm peak; FIG. 10A). Initial characterizations were conducted with no light delivered, to acquire a baseline social preference (FIG. 10B). In this test, all mice showed significant preference for the social chamber (FIG. 10B, FIG. 11; CaMKIIα-SSFO mice p=0.002; SSFO/C1V1 mice p=0.0003; CaMKIIα-EYFP mice p=0.032).

Figure 11:
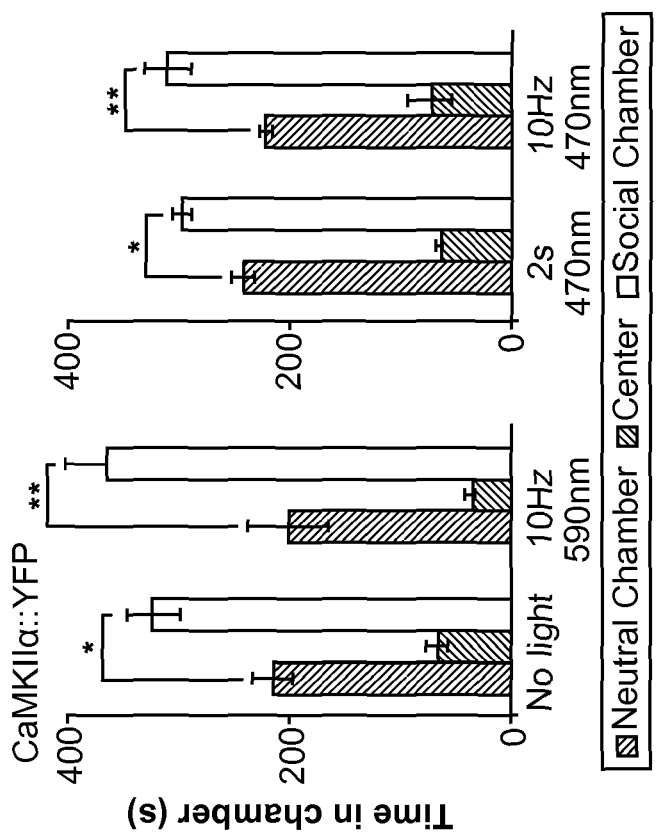
FIG. 11 depicts combinatorial optical control of mPFC cellular E/I balance: control experiments. Diagrams illustrate the light-stimulation protocols used in 4 different experiments using CaMKIIα::YFP mice. In all four experiments, light stimulation had no effect on the significant preference of these control mice to spend time in the chamber in which the novel conspecific mouse was located (n=8 mice).
Figure 11:
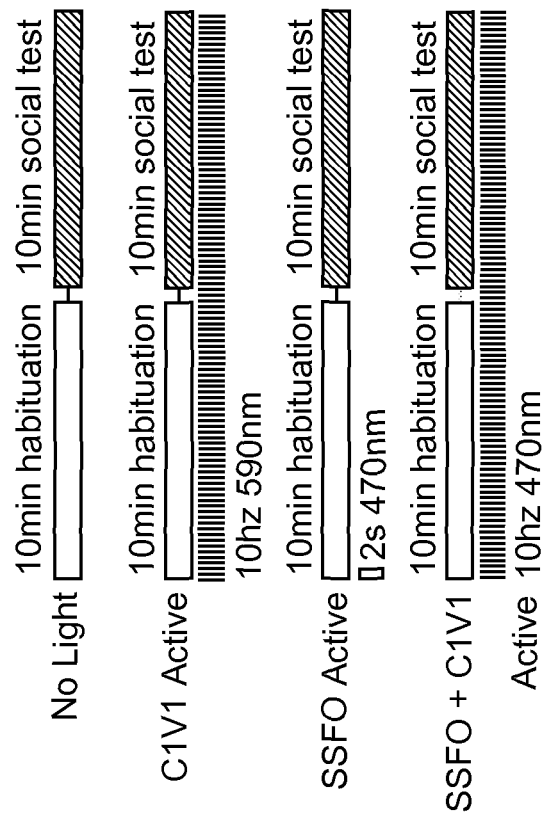

Next mice in the same paradigm were tested with novel juvenile mice, while delivering pulsed laser light at 590 nm to activate only CIV1-E122T/E162T in the PV cells in the SSFO/C1V1 mice (FIG. 10B). In this test, again, all mice showed normal preference for the novel juvenile mouse (FIG. 10C and FIG. 11; CaMKIIα-SSFO mice p=0.008;

SSFO/C1V1 mice p=0.005; CaMKIIα-EYFP mice p=0.014), consistent with the earlier PV::SSFO experiments. In a third test, SSFO was activated with a 2 s 470 nm light pulse during the pre-test habituation period (FIG. 10B). In this test, both the CaMKIIα::SSFO group and the SSFO/C1V1 group showed no preference for the social chamber (FIG. 10C-D; p=0.21 and p=0.87, respectively), a profound social behavior deficit consistent with our previous observations in CaMKIIα::SSFO mice (FIG. 31). Note the importance of spectrotemporal separation here: while the use of 470 nm light for maximal drive of SSFO will certainly involve drive of C1V1-E122T/E162T as well, the contrasting transience of C1V1-E122T/E162T and the stability of SSFO ensures that the behavioral testing carried out after the 2 s 470 nm light pulse is in the presence only of SSFO activity. Lastly, it was sought to rescue the behavioral deficit by compensating cellular E/I balance, adding to the activation of SSFO in excitatory cells an additional activation of C1V1-E122T/E162T in inhibitory cells by delivering pulses of 470 nm light at 10 Hz throughout the behavioral testing period (FIG. 10A-B). Under these illumination conditions, CaMKIIα::SSFO mice (with no C1V1-E122T/E162T to be activated, experiencing a pure elevation in cellular E/I balance) showed severe social behavior impairment with no significant preference to the social chamber (FIG. 10C; p=0.59) but in contrast, in the SSFO/C1V1 mice, preference to the social chamber was restored (FIG. 10D; p=0.005) by this compensatory increased activity of inhibitory neurons. As expected, control CaMKIIα-EYFP mice showed significant preference to the social chamber under both the 2 s 470 nm and the 10 Hz 470 nm stimulation paradigms (FIG. 11).

Discussion

Several lines of evidence have suggested the involvement of elevated cellular excitation-inhibition (E/I) balance in the etiology of medication-unresponsive social and information-processing impairments in autism and schizophrenia. But it has been difficult to formally test this hypothesis without 1) selective control over individual cell types; and 2) separating long-term effects of such control on the development and maturation of the circuit from immediate effects of E/I abnormalities with regard to the operation of the neural circuits involved. The tight interplay and pharmacological complexity of excitation and inhibition within cortical microcircuitry have precluded the confirmation of elevated cellular E/I balance as a core component of behavioral defects observed in the various disease models and human patients. Here, using two novel optogenetic tools, direct support for the elevated cellular E/I balance hypothesis was obtained, and circuit-physiology manifestations of the resulting social dysfunction were identified.

To more fully understand the elevated E/I state, the underlying circuit physiology manifestations were probed both in vitro and in vivo, which will undoubtedly be complex given the broad range of circuit phenomena that a cellular E/I balance elevation could initiate. Cellular E/I balance elevation was found to alter the transfer functions of principal neurons in a way that quantitatively impaired information transmission within cortical circuitry. In marked contrast, reduction in E/I balance (which did not affect social function despite dramatic effects on principal cell spike rates) did not impair information transmission and preserved the overall shape of principal neuron transfer functions. Also identified was correspondence between a clinical marker of disease states linked to social dysfunction (elevated baseline gamma power) and electrophysiological findings during free behavior in the elevated cellular E/I state. Using a novel chronic multisite optrode (CMO) device for combined recording and optical modulation in awake, behaving mice, it was found that the elevated E/I state is associated with robust, stable gamma oscillations that are generated by and manifested within the regions directly experiencing elevated cellular E/I balance. In these mice a specific impairment in social behavior but no gross changes in locomotor behavior or exploration of inanimate objects under the elevated E/I-gamma state was observed.

The effects of elevated E/I balance on social behavior showed evidence of specificity for PFC, since increasing the E/I ratio elsewhere, in primary visual cortex, did not impair social behavior. The PFC network, with its extensive subcortical connectivity, might therefore be particularly susceptible to eliciting psychiatric-related symptoms in the setting of subtle changes in E/I balance, a notion that is supported by observed of alterations in PFC inhibitory markers associated with psychiatric disease and the altered PFC rhythmicity observed in autistic individuals. Behavioral impairment under conditions in which PV-positive neurons were inhibited were not observed; notably, the ability to fully inhibit PV-positive neurons is limited by the penetrance of expression (DIO::SSFO expressed in ~25% of PV-positive cells), and the fact that impact will depend on baseline activity level of the targeted cells.

Finally, to attempt to restore the impairment resulting from elevated E/I balance, a family of novel extensively-engineered red light-activated channelrhodopsins, collectively termed C1V1 variants were utilized, to independently modulate both excitatory neurons (using SSFO) and inhibitory PV neurons (using a C1V1 variant). Using a novel form of integrated spectrotemporal separation of the activity of two optogenetic tools, it was found that increased cellular inhibition ameliorated social behavior deficits in mice that had been subjected to elevation of cellular E/I balance.

The examples, which are intended to be purely exemplary of the invention and should therefore not be considered to limit the invention in any way, also describe and detail aspects and embodiments of the invention discussed above. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

REFERENCES

1 Pardo, C. A. & Eberhart, C. G. The neurobiology of autism. *Brain Pathol* 17, 434-447 (2007).
2 O'Donovan, M. C., Craddock, N. J. & Owen, M. J. Genetics of psychosis; insights from views across the genome. *Hum Genet* 126, 3-12 (2009).
3 Sudhof, T. C. Neuroligins and neurexins link synaptic function to cognitive disease. *Nature* 455, 903-911 (2008).

4 Patterson, P. H. Modeling autistic features in animals. *Pediatr Res* 69, 34R-40R, doi:10.1203/PDR.0b013e318212b80f (2011).

5 Folstein, S. E. & Rosen-Sheidley, B. Genetics of autism: complex aetiology for a heterogeneous disorder. *Nat Rev Genet* 2, 943-955 (2001).

6 Walsh, T. et al. Rare structural variants disrupt multiple genes in neurodevelopmental pathways in schizophrenia. *Science* 320, 539-543 (2008).

7 Markram, K. & Markram, H. The intense world theory—a unifying theory of the neurobiology of autism. *Front Hum Neurosci* 4, 224 (2010).

8 Vattikuti, S. & Chow, C. C. A computational model for cerebral cortical dysfunction in autism spectrum disorders. *Biol Psychiatry* 67, 672-678 (2010).

9 Kehrer, C., Maziashvili, N., Dugladze, T. & Gloveli, T. Altered Excitatory-Inhibitory Balance in the NMDA-Hypofunction Model of Schizophrenia. *Front Mol Neurosci* 1, 6 (2008).

Rubenstein, J. L. Three hypotheses for developmental defects that may underlie some forms of autism spectrum disorder. *Curr Opin Neurol* 23, 118-123 (2010).

11 Rubenstein, J. L. & Merzenich, M. M. Model of autism: increased ratio of excitation/inhibition in key neural systems. *Genes Brain Behav* 2, 255-267 (2003).

12 Gogolla, N. et al. Common circuit defect of excitatory-inhibitory balance in mouse models of autism. *J Neurodev Disord* 1, 172-181 (2009).

13 Hashimoto, T. et al. Conserved regional patterns of GABA-related transcript expression in the neocortex of subjects with schizophrenia. *Am J Psychiatry* 165, 479-489 (2008).

14 Hashimoto, T. et al. Gene expression deficits in a subclass of GABA neurons in the prefrontal cortex of subjects with schizophrenia. *J Neurosci* 23, 6315-6326 (2003).

Lewis, D. A., Hashimoto, T. & Volk, D. W. Cortical inhibitory neurons and schizophrenia. *Nat Rev Neurosci* 6, 312-324 (2005).

16 Lewis, D. A., Volk, D. W. & Hashimoto, T. Selective alterations in prefrontal cortical GABA neurotransmission in schizophrenia: a novel target for the treatment of working memory dysfunction. *Psychopharmacology (Berl)* 174, 143-150 (2004).

17 Lisman, J. E. et al. Circuit-based framework for understanding neurotransmitter and risk gene interactions in schizophrenia. *Trends Neurosci* 31, 234-242 (2008).

18 Belforte, J. E. et al. Postnatal NMDA receptor ablation in corticolimbic interneurons confers schizophrenia-like phenotypes. *Nat Neurosci* 13, 76-83 (2010).

19 Blatt, G. J. et al. Density and distribution of hippocampal neurotransmitter receptors in autism: an autoradiographic study. *J Autism Dev Disord* 31, 537-543 (2001).

20 Bourgeron, T. A synaptic trek to autism. *Curr Opin Neurobiol* 19, 231-234 (2009).

21 Belmonte, M. K., Gomot, M. & Baron-Cohen, S. Visual attention in autism families: 'unaffected' sibs share atypical frontal activation. *J Child Psychol Psychiatry* 51, 259-276 (2010).

22 Gomot, M., Belmonte, M. K., Bullmore, E. T., Bernard, F. A. & Baron-Cohen, S. Brain hyper-reactivity to auditory novel targets in children with high-functioning autism. *Brain* 131, 2479-2488 (2008).

23 Dichter, G. S., Felder, J. N. & Bodfish, J. W. Autism is characterized by dorsal anterior cingulated hyperactivation during social target detection. *Soc Cogn Affect Neurosci* 4, 215-226 (2009).

24 Orekhova, E. V. et al. Excess of high frequency electroencephalogram oscillations in boys with autism. *Biol Psychiatry* 62, 1022-1029 (2007).

25 Rojas, D. C., Maharajh, K., Teale, P. & Rogers, S. J. Reduced neural synchronization of gamma-band MEG oscillations in first-degree relatives of children with autism. *BMC Psychiatry* 8, 66 (2008).

26 Gillberg, C. & Billstedt, E. Autism and Asperger syndrome: coexistence with other clinical disorders. *Acta Psychiatr Scand* 102, 321-330 (2000).

27 Canitano, R. Epilepsy in autism spectrum disorders. *Eur Child Adolesc Psychiatry* 16, 61-66 (2007).

28 Rippon, G., Brock, J., Brown, C. & Boucher, J. Disordered connectivity in the autistic brain: challenges for the "new psychophysiology". *Intl J Psychophysiol* 63, 164-172 (2007).

29 Dani, V. S. et al. Reduced cortical activity due to a shift in the balance between excitation and inhibition in a mouse model of Rett syndrome. *Proc Natl Acad Sci USA* 102, 12560-12565 (2005).

30 Etherton, M. R., Blaiss, C. A., Powell, C. M. & Sudhof, T. C. Mouse neurexin-1alpha deletion causes correlated electrophysiological and behavioral changes consistent with cognitive impairments. *Proc Natl Acad Sci USA* 106, 17998-18003 (2009).

31 Tabuchi, K. et al. A neuroligin-3 mutation implicated in autism increases inhibitory synaptic transmission in mice. *Science* 318, 71-76 (2007).

32 Chao, H. T. et al. Dysfunction in GABA signalling mediates autism-like stereotypies and Rett syndrome phenotypes. *Nature* 468, 263-269 (2010).

33 Moretti, P. et al. Learning and memory and synaptic plasticity are impaired in a mouse model of Rett syndrome. *J Neurosci* 26, 319-327 (2006).

34 Rinaldi, T., Perrodin, C. & Markram, H. Hyper-connectivity and hyper-plasticity in the medial prefrontal cortex in the valproic Acid animal model of autism. *Front Neural Circuits* 2, 4 (2008).

35 Rinaldi, T., Silberberg, G. & Markram, H. Hyperconnectivity of local neocortical microcircuitry induced by prenatal exposure to valproic acid. *Cereb Cortex* 18, 763-770 (2008).

36 Adamantidis, A. R., Zhang, F., Aravanis, A. M., Deisseroth, K. & de Lecea, L. Neural substrates of awakening probed with optogenetic control of hypocretin neurons. *Nature* 450, 420-424 (2007).

37 Huber, D. et al. Sparse optical microstimulation in barrel cortex drives learned behaviour in freely moving mice. *Nature* 451, 61-64 (2008).

38 Sohal, V. S., Zhang, F., Yizhar, O. & Deisseroth, K. Parvalbumin neurons and gamma rhythms enhance cortical circuit performance. *Nature* 459, 698-702 (2009).

39 Tsai, H. C. et al. Phasic firing in dopaminergic neurons is sufficient for behavioral conditioning. *Science* 324, 1080-1084 (2009).

Hira, R. et al. Transcranial optogenetic stimulation for functional mapping of the motor cortex. *J Neurosci Methods* 179, 258-263 (2009).

41 Covington, H. E., 3rd et al. Antidepressant effect of optogenetic stimulation of the medial prefrontal cortex. *J Neurosci* 30, 16082-16090 (2010).

42 Cruikshank, S. J., Urabe, H., Nurmikko, A. V. & Connors, B. W. Pathway-specific feedforward circuits between thalamus and neocortex revealed by selective optical stimulation of axons. *Neuron* 65, 230-245 (2010).

43 Haubensak, W. et al. Genetic dissection of an amygdala microcircuit that gates conditioned fear. *Nature* 468, 270-276 (2010).

44 Kravitz, A. V. & Kreitzer, A. C. Optogenetic manipulation of neural circuitry in vivo. *Curr Opin Neurobiol* (2011).

Berndt, A., Yizhar, O., Gunaydin, L. A., Hegemann, P. & Deisseroth, K. Bi-stable neural state switches. *Nat Neurosci* 12, 229-234 (2009).

46 Diester, I. et al. An optogenetic toolbox designed for primates. *Nat Neurosci* 14, 387-397 (2011).

47 Bamann, C., Gueta, R., Kleinlogel, S., Nagel, G. & Bamberg, E. Structural guidance of the photocycle of channelrhodopsin-2 by an interhelical hydrogen bond. *Biochemistry* 49, 267-278 (2010).

48 Dittgen, T. et al. Lentivirus-based genetic manipulations of cortical neurons and their optical and electrophysiological monitoring in vivo. *Proc Natl Acad Sci USA* 101, 18206-18211 (2004).

49 Winslow, J. T. Mouse social recognition and preference. *Curr Protoc Neurosci* Chapter 8, Unit 8 16 (2003).

50 Ni, A. M. & Maunsell, J. H. Microstimulation reveals limits in detecting different signals from a local cortical region. *Curr Biol* 20, 824-828 (2010).

51 May, S. S. et al. Sociability and preference for social novelty in five inbred strains: an approach to assess autistic-like behavior in mice. *Genes Brain Behav* 3, 287-302 (2004).

52 Ben-Ari, Y., Krnjevic, K., Reinhardt, W. & Ropert, N. Intracellular observations on the disinhibitory action of acetylcholine in the hippocampus. *Neuroscience* 6, 2475-2484 (1981).

53 Buhl, E. H., Tamas, G. & Fisahn, A. Cholinergic activation and tonic excitation induce persistent gamma oscillations in mouse somatosensory cortex in vitro. *J Physiol* 513 (Pt 1), 117-126 (1998).

54 van Aerde, K. I. et al. Flexible spike timing of layer 5 neurons during dynamic beta oscillation shifts in rat prefrontal cortex. *J Physiol* 587, 5177-5196 (2009).

55 Wilson, T. W., Rojas, D. C., Reite, M. L., Teale, P. D. & Rogers, S. J. Children and adolescents with autism exhibit reduced MEG steady-state gamma responses. *Biol Psychiatry* 62, 192-197 (2007).

---

What is claimed is:

1. A method for identifying a chemical compound that restores a social behavior, communication, and/or conditioned behavior in a non-human mammal, the method comprising:
   (a) depolarizing excitatory neurons in the prefrontal cortex of the non-human mammal, wherein the excitatory neurons of the prefrontal cortex are genetically modified to express a light-activated cation channel protein on the cell membrane of the excitatory neurons, wherein depolarization comprises activating the light-activated cation channel protein with light, and wherein the non-human mammal is a mouse or a rat,
   wherein the light-activated cation channel protein comprises an amino acid sequence at least 85% identical to the amino acid sequence depicted in one of SEQ ID NOs:1-4, and comprises amino acid substitutions at amino acid residues corresponding to C128, D156, or both C128 and D156 of the amino acid sequence of SEQ ID NO:1, wherein depolarizing the excitatory neuron inhibits one or more social behaviors, communications, and/or conditioned behaviors in the non-human mammal;
   (b) administering a chemical compound to the non-human mammal; and
   (c) determining if the administration of the chemical compound to the non-human animal restores said one or more social behaviors, communications, and/or conditioned behaviors in the non-human mammal.

2. The method of claim 1, wherein the social behavior is selected from the group consisting of: allogrooming, resident-intruder aggression, isolation-induced fighting, sexual behavior, parental behavior, social recognition, and auditory communication.

3. The method of claim 1, wherein the residue corresponding to C128 of the amino acid sequence of SEQ ID NO:1 is substituted with serine.

4. The method of claim 1, wherein the residue corresponding to D156 of the amino acid sequence of SEQ ID NO:1 is substituted to alanine.

5. The method of claim 1, wherein the light-activated cation channel protein comprises an amino acid sequence at least 90% identical to the amino acid sequence depicted in one of SEQ ID NOs:1-4.

6. The method of claim 1, wherein the light-activated cation channel protein comprises an amino acid sequence at least 95% identical to the amino acid sequence depicted in one of SEQ ID NOs:1-4.

7. The method of claim 1, wherein the light-activated cation channel protein comprises an amino acid sequence at least 95% identical to the sequence shown in SEQ ID NO:1, and wherein C128 is substituted with serine and D156 is substituted with alanine.

8. The method of claim 1, wherein the non-human mammal is a mouse.

9. The method of claim 1, wherein the non-human mammal is a rat.

10. The method of claim 1, wherein the neurons are in the infralimbic or prelimbic subregions of the medial prefrontal cortex.

* * * * *

UNITED STATES PATENT AND TRADEMARK OFFICE
CERTIFICATE OF CORRECTION

| | | |
|---|---|---|
| PATENT NO. | : 10,568,307 B2 | Page 1 of 1 |
| APPLICATION NO. | : 13/882666 | |
| DATED | : February 25, 2020 | |
| INVENTOR(S) | : Deisseroth et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 901 days.

Signed and Sealed this
Twentieth Day of December, 2022

Katherine Kelly Vidal
*Director of the United States Patent and Trademark Office*

SEQUENCE LISTING

```
<160> NUMBER OF SEQ ID NOS: 8

<210> SEQ ID NO 1
<211> LENGTH: 310
<212> TYPE: PRT
<213> ORGANISM: Chlamydomonas reinhardtii

<400> SEQUENCE: 1

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220
```

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
            245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 2
<211> LENGTH: 344
<212> TYPE: PRT
<213> ORGANISM: Chlamydomonas reinhardtii

<400> SEQUENCE: 2

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Ile Leu Ile His Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Ile Cys Arg Asp Leu Val Arg Tyr Leu Ala Trp
                245                 250                 255

Leu Tyr Phe Cys Ser Trp Ala Met Phe Pro Val Leu Phe Leu Leu Gly
            260                 265                 270

Pro Glu Gly Phe Gly His Ile Asn Gln Phe Asn Ser Ala Ile Ala His
        275                 280                 285

Ala Ile Leu Asp Leu Ala Ser Lys Asn Ala Trp Ser Met Met Gly His
290                 295                 300

Phe Leu Arg Val Lys Ile His Glu His Ile Leu Leu Tyr Gly Asp Ile
305                 310                 315                 320

Arg Lys Lys Gln Lys Val Asn Val Ala Gly Gln Glu Met Glu Val Glu
                325                 330                 335

Thr Met Val His Glu Glu Asp Asp
                340

<210> SEQ ID NO 3
<211> LENGTH: 300
<212> TYPE: PRT
<213> ORGANISM: Volvox carteri

<400> SEQUENCE: 3

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
            20                  25                  30

Gly Trp Leu Arg Ser Arg Gly Thr Ser Ile Glu Lys Thr Ile Ala Ile
        35                  40                  45

Thr Leu Gln Trp Val Val Phe Ala Leu Ser Val Ala Cys Leu Gly Trp
50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Ser Gly Asn Gly Val Val
            100                 105                 110

Trp Met Arg Tyr Gly Glu Trp Leu Leu Thr Cys Pro Val Leu Leu Ile
        115                 120                 125

His Leu Ser Asn Leu Thr Gly Leu Lys Asp Asp Tyr Ser Lys Arg Thr
130                 135                 140

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
            180                 185                 190

Glu Ala Phe His Thr Val Pro Lys Gly Ile Cys Arg Glu Leu Val Arg
        195                 200                 205

Val Met Ala Trp Thr Phe Phe Val Ala Trp Gly Met Phe Pro Val Leu
210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
            260                 265                 270

Tyr Gly Asp Ile Arg Lys Lys Gln Lys Ile Thr Ile Ala Gly Gln Glu
        275                 280                 285

Met Glu Val Glu Thr Leu Val Ala Glu Glu Asp
290                 295                 300

```
<210> SEQ ID NO 4
<211> LENGTH: 747
<212> TYPE: PRT
<213> ORGANISM: Volvox carteri

<400> SEQUENCE: 4

Met Asp His Pro Val Ala Arg Ser Leu Ile Gly Ser Ser Tyr Thr Asn
1               5                   10                  15

Leu Asn Asn Gly Ser Ile Val Ile Pro Ser Asp Ala Cys Phe Cys Met
            20                  25                  30

Lys Trp Leu Lys Ser Lys Gly Ser Pro Val Ala Leu Lys Met Ala Asn
        35                  40                  45

Ala Leu Gln Trp Ala Ala Phe Ala Leu Ser Val Ile Ile Leu Ile Tyr
    50                  55                  60

Tyr Ala Tyr Ala Thr Trp Arg Thr Thr Cys Gly Trp Glu Glu Val Tyr
65                  70                  75                  80

Val Cys Cys Val Glu Leu Thr Lys Val Val Ile Glu Phe Phe His Glu
                85                  90                  95

Phe Asp Glu Pro Gly Met Leu Tyr Leu Ala Asn Gly Asn Arg Val Leu
            100                 105                 110

Trp Leu Arg Tyr Gly Glu Trp Leu Leu Thr Cys Pro Val Ile Leu Ile
        115                 120                 125

His Leu Ser Asn Leu Thr Gly Leu Lys Asp Asp Tyr Asn Lys Arg Thr
    130                 135                 140

Met Arg Leu Leu Val Ser Asp Val Gly Thr Ile Val Trp Gly Ala Thr
145                 150                 155                 160

Ala Ala Met Ser Thr Gly Tyr Ile Lys Val Ile Phe Phe Leu Leu Gly
                165                 170                 175

Cys Met Tyr Gly Ala Asn Thr Phe Phe His Ala Ala Lys Val Tyr Ile
            180                 185                 190

Glu Ser Tyr His Thr Val Pro Lys Gly Leu Cys Arg Gln Leu Val Arg
        195                 200                 205

Ala Met Ala Trp Leu Phe Phe Val Ser Trp Gly Met Phe Pro Val Leu
    210                 215                 220

Phe Leu Leu Gly Pro Glu Gly Phe Gly His Leu Ser Val Tyr Gly Ser
225                 230                 235                 240

Thr Ile Gly His Thr Ile Ile Asp Leu Leu Ser Lys Asn Cys Trp Gly
                245                 250                 255

Leu Leu Gly His Phe Leu Arg Leu Lys Ile His Glu His Ile Leu Leu
            260                 265                 270

Tyr Gly Asp Ile Arg Lys Val Gln Lys Ile Arg Val Ala Gly Glu Glu
        275                 280                 285

Leu Glu Val Glu Thr Leu Met Thr Glu Glu Ala Pro Asp Thr Val Lys
    290                 295                 300

Lys Ser Thr Ala Gln Tyr Ala Asn Arg Glu Ser Phe Leu Thr Met Arg
305                 310                 315                 320

Asp Lys Leu Lys Glu Lys Gly Phe Glu Val Arg Ala Ser Leu Asp Asn
                325                 330                 335

Ser Gly Ile Asp Ala Val Ile Asn His Asn Asn Tyr Asn Asn Ala
            340                 345                 350

Leu Ala Asn Ala Ala Ala Val Gly Lys Pro Gly Met Glu Leu Ser
        355                 360                 365

Lys Leu Asp His Val Ala Ala Asn Ala Ala Gly Met Gly Gly Ile Ala
    370                 375                 380
```

-continued

```
Asp His Val Ala Thr Thr Ser Gly Ala Ile Ser Pro Gly Arg Val Ile
385                 390                 395                 400

Leu Ala Val Pro Asp Ile Ser Met Val Asp Tyr Phe Arg Glu Gln Phe
            405                 410                 415

Ala Gln Leu Pro Val Gln Tyr Glu Val Val Pro Ala Leu Gly Ala Asp
            420                 425                 430

Asn Ala Val Gln Leu Val Val Gln Ala Ala Gly Leu Gly Gly Cys Asp
            435                 440                 445

Phe Val Leu Leu His Pro Glu Phe Leu Arg Asp Lys Ser Ser Thr Ser
450                 455                 460

Leu Pro Ala Arg Leu Arg Ser Ile Gly Gln Arg Val Ala Ala Phe Gly
465                 470                 475                 480

Trp Ser Pro Val Gly Pro Val Arg Asp Leu Ile Glu Ser Ala Gly Leu
            485                 490                 495

Asp Gly Trp Leu Glu Gly Pro Ser Phe Gly Leu Gly Ile Ser Leu Pro
            500                 505                 510

Asn Leu Ala Ser Leu Val Leu Arg Met Gln His Ala Arg Lys Met Ala
            515                 520                 525

Ala Met Leu Gly Gly Met Gly Gly Met Leu Gly Ser Asn Leu Met Ser
530                 535                 540

Gly Ser Gly Gly Val Gly Leu Met Gly Ala Gly Ser Pro Gly Gly Gly
545                 550                 555                 560

Gly Gly Ala Met Gly Val Gly Met Thr Gly Met Gly Met Val Gly Thr
            565                 570                 575

Asn Ala Met Gly Arg Gly Ala Val Gly Asn Ser Val Ala Asn Ala Ser
            580                 585                 590

Met Gly Gly Gly Ser Ala Gly Met Gly Met Gly Met Met Gly Met Val
            595                 600                 605

Gly Ala Gly Val Gly Gly Gln Gln Gln Met Gly Ala Asn Gly Met Gly
610                 615                 620

Pro Thr Ser Phe Gln Leu Gly Ser Asn Pro Leu Tyr Asn Thr Ala Pro
625                 630                 635                 640

Ser Pro Leu Ser Ser Gln Pro Gly Gly Asp Ala Ser Ala Ala Ala Ala
            645                 650                 655

Ala Ala Ala Ala Ala Ala Ala Thr Gly Ala Ala Ser Asn Ser Met Asn
            660                 665                 670

Ala Met Gln Ala Gly Gly Ser Val Arg Asn Ser Gly Ile Leu Ala Gly
            675                 680                 685

Gly Leu Gly Ser Met Met Gly Pro Pro Gly Ala Pro Ala Ala Pro Thr
690                 695                 700

Ala Ala Ala Thr Ala Ala Pro Ala Val Thr Met Gly Ala Pro Gly Gly
705                 710                 715                 720

Gly Gly Ala Ala Ala Ser Glu Ala Glu Met Leu Gln Gln Leu Met Ala
            725                 730                 735

Glu Ile Asn Arg Leu Lys Ser Glu Leu Gly Glu
            740                 745
```

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide

```
<400> SEQUENCE: 5

Lys Ser Arg Ile Thr Ser Glu Gly Glu Tyr Ile Pro Leu Asp Gln Ile
1               5                   10                  15

Asp Ile Asn Val
            20

<210> SEQ ID NO 6
<211> LENGTH: 47
<212> TYPE: PRT
<213> ORGANISM: Artificial Sequence
<220> FEATURE:
<223> OTHER INFORMATION: Synthetic peptide

<400> SEQUENCE: 6

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
            20                  25                  30

Gln Cys Tyr Cys Ala Gly Trp Ile Glu Ser Arg Gly Thr Asn Gly
        35                  40                  45

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (2)...(2)
<223> OTHER INFORMATION: xaa = any amino acid

<400> SEQUENCE: 7

Phe Xaa Tyr Glu Asn Glu
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide

<400> SEQUENCE: 8

Phe Cys Tyr Glu Asn Glu Val
1               5
```